United States Patent [19]

Hanagan

[11] Patent Number: 4,764,204

[45] Date of Patent: Aug. 16, 1988

[54] HERBICIDAL SULFONAMIDES

[75] Inventor: Mary A. Hanagan, Blue Bell, Pa.

[73] Assignee: E. I. Du Pont de Nemours and Company, Wilmington, Del.

[21] Appl. No.: 78,154

[22] Filed: Jul. 27, 1987

Related U.S. Application Data

[60] Division of Ser. No. 841,109, Mar. 18, 1986, Pat. No. 4,705,556, which is a division of Ser. No. 628,259, Aug. 12, 1984, Pat. No. 4,604,131, which is a continuation-in-part of Ser. No. 520,801, Aug. 5, 1983, abandoned.

[51] Int. Cl.$^4$ ............... C07D 251/20; C07D 251/22; C07D 401/12; A01N 43/66
[52] U.S. Cl. ................................ 71/93; 544/219
[58] Field of Search ........................ 544/219; 71/93

[56] References Cited

U.S. PATENT DOCUMENTS

| | | | |
|---|---|---|---|
| 4,310,346 | 1/1982 | Levitt et al. | 71/92 |
| 4,369,058 | 1/1983 | Levitt | 71/92 |
| 4,378,991 | 4/1983 | Levitt | 71/93 |
| 4,383,113 | 5/1983 | Levitt | 544/211 |
| 4,394,506 | 7/1983 | Levitt | 544/321 |
| 4,417,917 | 11/1983 | Levitt et al. | 71/93 |
| 4,421,550 | 12/1983 | Selby et al. | 71/92 |
| 4,425,154 | 1/1984 | Meyer et al. | 71/92 |
| 4,460,401 | 7/1984 | Sauers | 71/92 |
| 4,465,505 | 8/1984 | Wolf | 71/92 |
| 4,496,392 | 1/1985 | Levitt | 71/93 |
| 4,511,392 | 4/1985 | Rorer | 71/90 |
| 4,518,776 | 5/1985 | Meyer et al. | 544/206 |
| 4,521,597 | 6/1985 | Kristinsson et al. | 544/3 |
| 4,536,576 | 8/1985 | Levitt | 544/321 |
| 4,545,808 | 10/1985 | Levitt | 71/92 |
| 4,564,384 | 1/1986 | Levitt | 71/92 |
| 4,591,378 | 5/1986 | Levitt | 71/93 |
| 4,592,978 | 6/1986 | Levitt | 544/321 |
| 4,618,363 | 10/1986 | Gass et al. | 71/90 |
| 4,627,873 | 12/1986 | Levitt | 71/93 |
| 4,647,303 | 3/1987 | Levitt | 71/90 |
| 4,687,507 | 8/1987 | Levitt | 71/92 |
| 4,689,072 | 8/1987 | Levitt | 71/93 |

FOREIGN PATENT DOCUMENTS

| | | |
|---|---|---|
| 0030433 | 6/1981 | European Pat. Off. . |
| 0035893 | 9/1981 | European Pat. Off. . |
| 0044209 | 1/1982 | European Pat. Off. . |
| 0044212 | 1/1982 | European Pat. Off. . |

*Primary Examiner*—John M. Ford

[57] ABSTRACT

This invention relates to novel herbicidally active sulfonylurea compounds substituted in the positions ortho to the sulfonylurea bridge, agriculturally suitable compositions thereof and methods of their use as preemergent or postemergent herbicides or plant growth regulants.

18 Claims, No Drawings

HERBICIDAL SULFONAMIDES

RELATED APPLICATION

This application is a divisional of Ser. No. 841,109, filed Mar. 18, 1986, U.S. Pat. No. 4,705,556, which is a divisional of Ser. No. 628,259, filed July 12, 1984, U.S. Pat. No. 4,604,131, which is a continuation-in-part of Ser. No. 520,801, filed Aug. 5, 1983, abandoned.

BACKGROUND OF THE INVENTION

This invention relates to novel herbicidal sulfonamide compounds with substituents in both positions ortho to the sulfonylurea bridge, suitable agricultural compositions thereof and a method for their use as preemergent or postemergent herbicides or plant growth regulants.

Herbicidal sulfonamides of the type described herein are generally referred to in the art as "sulfonylurea" herbicides.

The "sulfonylurea" herbicides are an extremely potent class of herbicides discovered within the last few years. This class of herbicides, generally consists of a sulfonylurea bridge, —$SO_2NHCONH$—, linking two aromatic or heteroaromatic rings. See, for example, the compounds disclosed in U.S. Pat. Nos. 4,169,719, 4,127,405, 4,120,691, 4,221,585, 4,190,432, 4,225,337, 4,371,391, 4,339,266, 4,191,553, 4,305,884, 4,214,890, 4,339,267, 4,302,241, 4,342,587, 4,310,346, 4,293,330, 4,301,286, 4,370,479 4,370,480, 4,368,067, 4,369,320, 4,348,219, 4,348,220, 4,333,760, 4,368,069, and 3,323,611 as well as European Patent Application No. 79300982.0 (Publication No. 7,687, published Feb. 6, 1980).

New compounds effective for controlling the growth of undesired vegetation are in constant demand. In the most common situation, such compounds are sought to selectively control the growth of undesired vegetation to permit the growth of useful crops such as cotton, rice, corn, wheat and soybeans, to name a few. Unchecked weed growth in such useful crops can cause significant losses, reducing profit to the farmer and increasing costs to the consumer. In other situations, herbicides are desired which will control all plant growth. Examples of areas in which complete control of all vegetation is desired are areas around fuel storage tanks, ammunition depots and industrial storage areas. There are many products commercially available for these purposes, but the search continues for products which are more effective, less costly and environmentally safe.

EPO Pub. No. 7,687, discloses herbicidal sulfonylureas bearing ortho-carboxylic acid ester groups.

EPO Pub. No. 23,141, discloses herbicidal sulfonylureas bearing ortho-sulfamoyl groups.

EPO Pub. No. 44,211, discloses herbicidal sulfonylureas bearing ortho-phenyl groups.

EPO Pub. No. 44,209, discloses herbicidal sulfonylureas bearing —$CH_2OR$ and $CH_2CO_2R_8$ ortho-groups.

EPO Pub. No. 35,893, discloses herbicidal sulfonylureas bearing an ortho-sulfonyl group.

EPO Pub. No. 44,212, discloses herbicidal sulfonylureas bearing ortho-sulfonate groups.

U.S. Pat. No. 4,369,058, issued Jan. 18, 1983 discloses herbicidal sulfonylureas bearing ortho-amino substituents.

EPO Pub. No. 83,975, discloses herbicidal sulfonylureas bearing ortho-heterocyclic substituents.

EPO Pub. No. 85,476, discloses herbicidal sulfonylureas bearing ortho-pyridyl, pyrimidyl, triazinyl and furanyl groups.

South African Patent Application No. 83/0127 discloses herbicidal N-arylsulfonyl-N'-pyrimidinylureas of formula $$XSO_2NHC(Z)N(R_{18})\text{-pyrimidine}(OCHF_2)(Y)$$

where

X is optionally substituted phenyl or naphthyl.

South African Patent Application No. 83/0441 discloses herbicidal ureas of formula $$R_1\text{-phenyl}(X-A_m-Q)\text{-}SO_2NHC(O)NH\text{-pyrimidine}(R_2)(E)(R_3)$$

where

X is O, S, SO or $SO_2$;

m is 0 or 1; and

Q is any of a wide variety of moieties.

South African Patent Application No. 83/8416 discloses herbicidal sulfonamides of formula $$R_1\text{-phenyl}(A)\text{-}SO_2NHC(Z)N(R_2)\text{-pyrimidine}(R_3)(E)(R_4)$$

where

A is an unsaturated or only partially saturated 5- or 6-membered heterocyclic ring system which is bonded through a carbon atom and contains 1, 2 or 3 heteroatoms and which may be substituted; and $R_1$ is H, halo, $NO_2$, $C_1$-$C_4$ alkyl, $C_1$-$C_4$ haloalkyl, $C_1$-$C_4$ alkoxy, $C_1$-$C_4$ haloalkoxy, $C_1$-$C_4$ alkoxycarbonyl, $C_1$-$C_4$ alkylthio, $C_1$-$C_4$ alkylsulfinyl, $C_1$-$C_4$ alkylsulfonyl or $C_2$-$C_5$ alkoxyalkoxy.

SUMMARY OF THE INVENTION

Novel compounds, suitable agricultural compositions thereof and a method for their use as preemergent or postemergent herbicides or plant growth regulants have been found. The novel compounds of this invention are of the formula $$\text{I}$$

phenyl ring (positions 1-6) with $R_1$, $R_2$, $R_3$ substituents and $SO_2NHC(O)N(R_4)$-A wherein $R_1$ is $S(O)_nR_5$, $CF_3$, $NR_6R_7$, $CO_2R_8$, $SO_2NR_9R_{10}$,

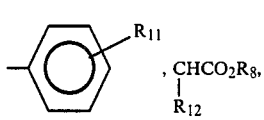

$OSO_2R_{13}$, $CH_2OR_{14}$ or Q;

$R_2$ is $S(O)_mR_5$, $CF_3$, $NR_6R_7$, $CO_2R_8$, $SO_2NR_9R_{10}$,

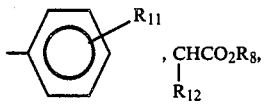

$OSO_2R_{13}$, $CH_2OR_{14}$ or Q;
$R_3$ is H, Cl, F, Br, $CH_3$, $OCH_3$ or $CF_3$;
$R_4$ is H or $CH_3$;
$R_5$ is $C_1$-$C_3$ alkyl;
$R_6$ and $R_7$ are independently $CH_3$ or $CH_2CH_3$;
$R_8$ is $C_1$-$C_3$ alkyl, $CH_2CH=CH_2$, $CH_2CH_2Cl$ or $CH_2CH_2OCH_3$;
$R_9$ is $CH_3$ or $OCH_3$;
$R_{10}$ is $C_1$-$C_3$ alkyl;
$R_{11}$ is H, Cl, Br, F, $CH_3$ or $OCH_3$;
$R_{12}$ is H or $CH_3$;
$R_{13}$ is $C_1$-$C_3$ alkyl or $CF_3$;
$R_{14}$ is $C_1$-$C_3$ alkyl or $CF_2H$;
n is 0, 1 or 2;
m is 0 or 1;

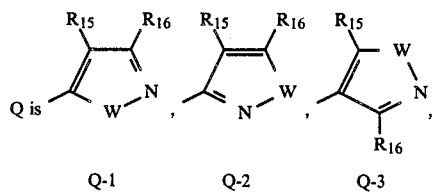

Q-1, Q-2, Q-3

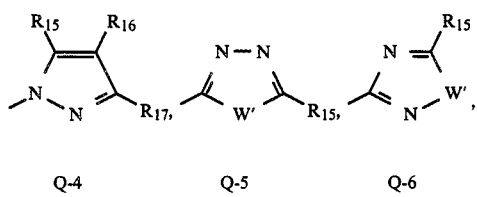

Q-4, Q-5, Q-6

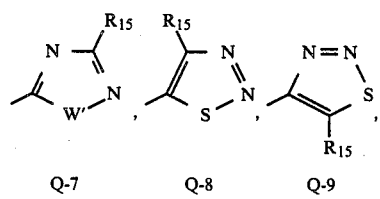

Q-7, Q-8, Q-9

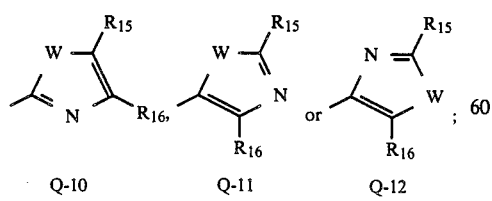

Q-10, Q-11, Q-12

W is O, S or $NR_{18}$;
W' is O or S;
$R_{15}$, $R_{16}$, $R_{17}$ and $R_{18}$ are independently H or $CH_3$;
Q is also

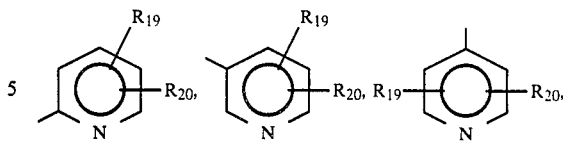

Q-13, Q-14, Q-15

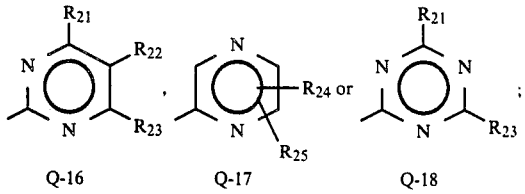

Q-16, Q-17, Q-18

$R_{19}$, $R_{20}$, $R_{22}$, $R_{24}$ and $R_{25}$ are independently H or $CH_3$;
$R_{21}$ and $R_{23}$ are independently H, $CH_3$ or $OCH_3$;
Q is also

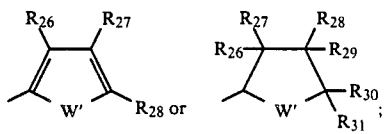

Q-19, Q-20

$R_{26}$, $R_{27}$, $R_{28}$, $R_{29}$, $R_{30}$ and $R_{31}$ are independently H or $CH_3$;

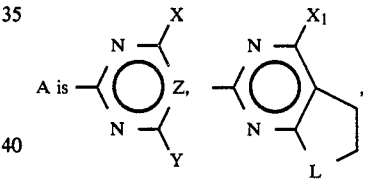

A-1, A-2

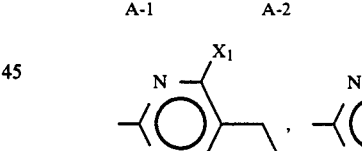

A-3, A-4

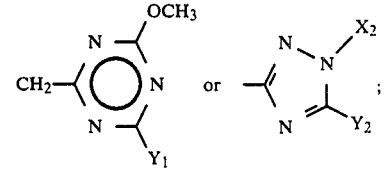

A-5, A-6

Z is CH or N;
L is O or $CH_2$;
X is $CH_3$, $OCH_3$, Cl, $OCH_2CH_3$, $OCF_2H$ or F;
Y is H, $NH_2$, $NHCH_3$, $N(CH_3)_2$, $CH_3$, $CH_2CH_3$, $CF_3$, $CH_2OCH_3$, $CH_2OCH_2CH_3$, $O(C_1$-$C_3$ alkyl), $SCH_3$, $O(C_3$-$C_4$ alkenyl), $O(C_3$-$C_4$ alkynyl), $OCH_2CF_3$, $OCH_2CH_2F$, $OCH_2CH_2Cl$, $OCH_2CH_2Br$ or $OCF_2H$;
$X_1$ is $CH_3$, $OCH_3$, Cl or $OCF_2H$;
$Y_1$ is $CH_3$ or $OCH_3$;
$X_2$ is $CH_3$, $CH_2CH_3$ or $CH_2CF_3$;
$Y_2$ is $CH_3$, $OCH_3$ or $SCH_3$; and
$Y_3$ is H or $CH_3$;
and agriculturally suitable salts thereof; provided that
(a) when either one of $R_1$ or $R_2$ is $CF_3$, then the other is also $CF_3$;
(b) $R_1$ and $R_2$ are not simultaneously $CO_2R_8$;
(c) when either one of $R_1$ or $R_2$ is $SO_2NR_9R_{10}$, then the other must not be $S(O)_nR_5$, $S(O)_mR_5$, $CH_2OR_{14}$ or $NR_6R_7$;
(d) when $R_9$ is $OCH_3$, then $R_{10}$ is $CH_3$;
(e) when either one of $R_1$ or $R_2$ is $CO_2R_8$, then the other must not be $S(O)_nR_5$, $S(O)_mR_5$ or $NR_6R_7$;
(f) the total number of carbon atoms in $R_{26}$ to $R_{31}$ combined, is equal to or less than four;
(g) when X is Cl or F, then Z is CH and Y is $NH_2$, $NHCH_3$, $N(CH_3)_2$, $OCH_3$ or $OCH_2CH_3$;
(h) when $R_1$ is $CO_2R_8$ and $R_2$ is $OSO_2R_{13}$, then A is not A-1; and
(i) when X or Y is $OCF_2H$ and A is A-1, then $R_2$ is Q.

The preferred compounds of the invention for their higher herbicidal activity, greater plant growth regulant activity and/or more favorable ease of synthesis are:

(1) Compounds of Formula 1 where A is A-1; $R_1$ and $R_2$ are not simultaneously Q and $R_4$ is H.
(2) Compounds of Preferred 1 where Y is $CH_3$, $CF_3$, $CH_2OCH_3$, $OCH_3$, $OCH_2CF_3$ or $OCF_2H$.
(3) Compounds of Preferred 2 where $R_3$ is in either the 3- or 5-position.
(4) Compounds of Preferred 3 where $R_1$ and $R_2$ are not simultaneously $SO_2NR_9R_{10}$ or $NR_6R_7$.
(5) Compounds of Preferred 4 where $R_3$ is H; and at least one of $R_1$ or $R_2$ is $S(O)_nR_5$, $S(O)_mR_5$, $CF_3$, $NR_6R_7$, $SO_2NR_9R_{10}$,

$OSO_2R_{13}$ or $CH_2OR_{14}$.

(6) Compounds of Preferred 5 where $R_5$ is $CH_3$ or $CH_2CH_3$; $R_6$ and $R_7$ are both $CH_3$; $R_{10}$ is $CH_3$; $R_{11}$ is H; $R_{13}$ is $CH_3$ or $CH_2CH_3$; and $R_{14}$ is $CH_3$.
(7) Compounds of Preferred 6 where X is $CH_3$, $OCH_3$ or Cl and Y is $CH_3$, $OCH_3$ or $CH_2OCH_3$.

The most preferred compounds of the invention for their highest herbicidal activity, greatest plant growth regulating activity and/or more favorable ease of synthesis are: N-[(4,6-dimethoxypyrimidin-2-yl)-aminocarbonyl]-3-methylsulfonyl-1,1'-biphenyl-2-sulfonamide, and N-[(4,6-dimethoxy-1,3,5-triazin-2-yl)-aminocarbonyl]-2,6-bis(methylthio)benzenesulfonamide.

DETAILED DESCRIPTION OF THE INVENTION

Synthesis

The compounds of Formula (I) may be prepared by one or more of the methods described below in Equations 1 to 4. The method of choice depends on the acid or base lability of the substituents and would be obvious to one skilled in the art.

As shown in Equation 1 below, compounds of Formula I can be prepared by the reaction of an appropriately substituted sulfonamide of Formula (II) with the appropriate methyl carbamate of Formula (III) in the presence of an equimolar amount of trimethylaluminum. The reactions are best carried out at 25° to 85° in an inert solvent such as methylene chloride or 1,2-dichloroethane under an inert atmosphere.

Equation 1

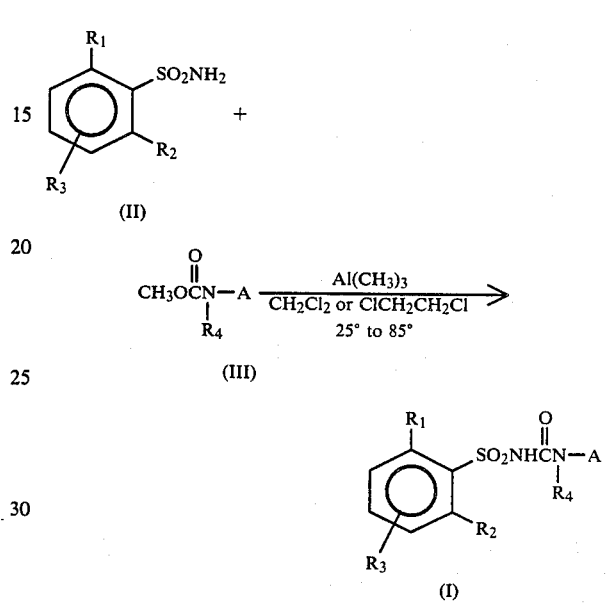

where
$R_1$ or $R_2$ is not $CO_2R_8$;
$R_3$ = H, Cl, F, Br, $CH_3$, $OCH_3$ or $CF_3$; and
$R_4$ is H.

Compounds of Formula (I) can also be prepared by reacting sulfonylcarbamate of Formula (IV) with an appropriate amine of Formula (V) as shown in Equation 2. The reaction is carried out at 50° to 100° in a solvent such as dioxane for 0.5 to 24 hours as taught in EPO Publication No. 44807, published Jan. 27, 1982. The required carbamates are prepared by reacting the preformed sodium salt of II with diphenylcarbonate.

Equation 2

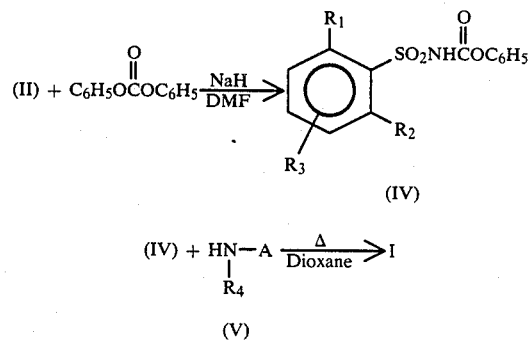

wherein
$R_1$ or $R_2$ is $S(O)_nR_5$, $CF_3$, $NR_6R_7$, $SO_2NR_9R_{10}$, $C_6H_4R_{11}$, $CH_2OR_{14}$ or Q;
$R_3$ is as described in Equation 1; and
$R_4$ is H or $CH_3$.

Some of the compounds of Formula (I) can also be prepared as shown in Equations 3a and 3b.

Equation 3a

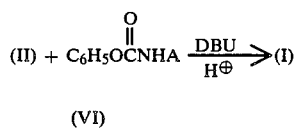

(VI)

The reaction of Equation 3a can be carried out by contacting equimolar amounts of a sulfonamide of Formula (II) with a heterocyclic phenyl carbamate of Formula (VI) in the presence of an equimolar amount of 1,8-diazabicyclo[5.4.0]undec-7-ene (DBU), by methods analogous to those described in South African Patent Application No. 830441. The phenyl carbamates of Formula (VI) can be prepared by methods, or modifications thereof known to those skilled in the art, described in South African Patent Application No. 825671 and South African Patent Application No. 825045.

Rarely a sulfonamide (II) may not be of sufficient stability to be useful as a starting material in Equations 1-3a. In this case, as well as others, the sulfonyl isocyanate (VIII), can be made as an unisolated intermediate by treating the corresponding sulfonyl chloride (XV) with isocyanate anion in the presence of the heterocyclic amine (V). The amine reacts with the sulfonyl isocyanate as it is formed to give the desired compound of Formula I.

Equations 3b

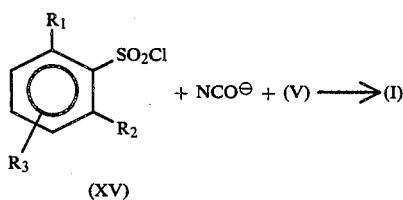

(XV)

The reaction is best carried out by adding over one to six hours a solution of at least one equivalent of a tetraalkylammonium isocyanate, such as tetra-n-butylammonium isocyanate, in a suitable aprotic organic solvent, such as dichloromethane or tetrahydrofuran, to a well-stirred mixture of one equivalent of sulfonyl chloride (XV) and at least one equivalent of heterocyclic amine (V) in a similar suitable organic solvent at 20°–40° C. The reaction mixture is then diluted with dichloromethane, washed with 1N sulfuric acid, and dried over sodium sulfate. Rotary evaporation of the solvent leaves the product of Formula (I).

The compounds of Formula I may be prepared as shown below in Equation 4 by the reaction of an appropriate benzenesulfonyl isocyanate, VIII with an appropriate aminoheterocycle, V.

Equation 4

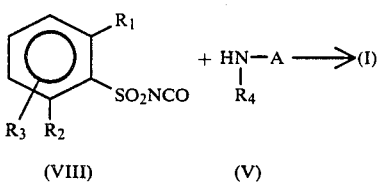

(VIII) (V)

wherein
$R_1$, $R_2$, $R_3$ and $R_4$ are as described in Equation 2; and
$R_1$ or $R_2$ may also be $CO_2R_8$,

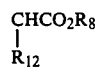

and $OSO_2R_{13}$.

The reaction of Equation 4 is best carried out in an inert aprotic solvent such as methylene chloride, tetrahydrofuran or acetonitrile at a temperature between 20° and 80°. A catalytic amount of 1,4-diazabicyclo [2,2,2]octane (DABCO) may be used to accelerate the reaction. In cases in which the products are insoluble in the reaction solvent, they may be isolated by simple filtration. When the products are soluble, they may be isolated by evaporation of the solvent and trituration of the residue with solvents such as 1-chlorobutane, diethyl ether or methanol and filtration. Impure products may be purified my column chromatography on silica gel.

The benzenesulfonyl isocyanates of Formula (VIII) may be prepared as shown in Equation 5, by phosgenation of the sulfonamides (II) in the presence of butyl isocyanate.

Equation 5

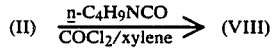

wherein
$R_1$, $R_2$ and $R_3$ are as described in Equation 4.

The above reaction is carried out by heating a mixture of the appropriate sulfonamide (II), an alkyl isocyanate such as butyl isocyanate and a catalytic amount of a tertiary amine such as 1,4-diazabicyclo[2,2,2]octane (DABCO) in xylene, or other inert solvent of boiling point ≧135°, to approximately 135°. Phosgene is then added to the mixture over a 1-6 hour period at 125°–135° until an excess of phosgene is present as indicated by a permanent drop in the boiling point to less than 130°. The mixture is cooled and filtered to remove a small amount of insoluble by-products. The solvent and the alkyl isocyanate are distilled off in vacuo leaving a residue of the crude, sulfonyl isocyanate (VIII) which can be used without further purification. This method is described in U.S. Pat. No. 4,238,621.

Alternatively, the sulfonyl isocyanates (VIII) can be prepared, as shown in Equation 6, in a two-step procedure. This method is similar to a procedure taught by Ulrich and Sayigh, *New Methods of Preparative Organic Chemisty*, Vol. VI, p. 223-241, Academic Press, New York and London, W. Forest Ed.

Equation 6

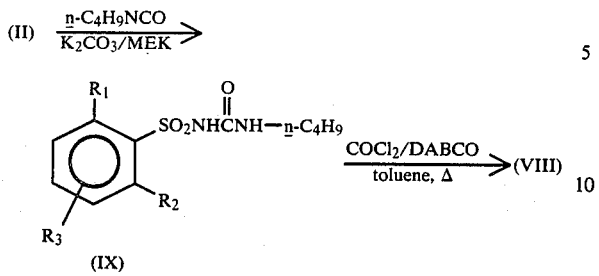

wherein $R_1$, $R_2$ and $R_3$ are as described in Equation 4.

The compounds of Formula (IX) are conveniently prepared by stirring a mixture of sulfonamides (II) anhydrous potassium carbonate, and n-butyl isocyanate in a solvent such as acetone or methyl ethyl ketone at 25°–80° until all of the isocyanate has reacted. The products are isolated by quenching in dilute mineral acid and recrystallizing the solid product. The compounds (IX) are treated with phosgene and a catalytic amount of DABCO in refluxing xylene or chlorobenzene in a manner analogous to that described in Equation 5.

Sulfonyl isocyanates of Formula (VIII) may also be prepared by the procedure shown below in Equation 7 starting from the appropriate sulfonamides.

Equation 7

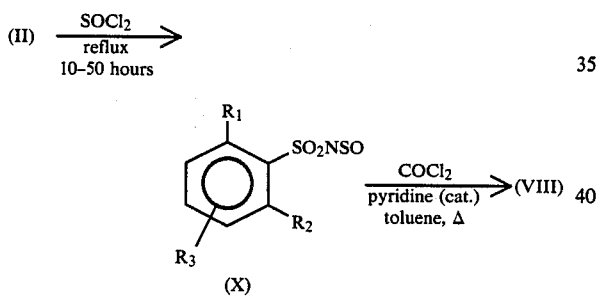

wherein $R_1$, $R_2$ and $R_3$ are as described in Equation 2.

The reactions of Equation 7 are best carried out according to the procedure of Ulrich et al. in *J. Org. Chem.*, 34, 3200 (1969). The sulfonamide is boiled under reflux with an excess of thionyl chloride which functions as both a reactant and solvent. When the sulfonamide protons are no longer detectable by proton NMR (15–20 hrs. on the average), the thionyl chloride is removed under reduced pressure and the residue is dissolved in an inert solvent such as toluene, benzene, xylenes, etc. A catalytic amount of pyridine is added. The mixture is treated with at least one equivalent of phosgene and heated to 60°–140° with 80°–100° C. preferred. Conversion to the isocyanate is substantially complete within about 174 to 3 hours. The mixture containing the sulfonyl isocyantate can be used directly or the sulfonyl isocyanate can be isolated in pure form by filtration and evaporation of the filtrate followed by vacuum distillation if necessary.

As shown in Equation 8 below, intermediate sulfonamides for Formula (II) can be prepared from t-butyl sulfonamides (XI). Of necessity, the reactions are limited to those cases in which $R_1$ is inert to lithium reagents under the conditions employed. During metallation, acids can be protected as amides and alcohols protected as tetrahydropyran ethers. For a general review of metallation with lithium reagents, see H. W. Gschwend and R. Rodriguez, *Org. Reactions*, 26, 1 (1979).

Equation 8

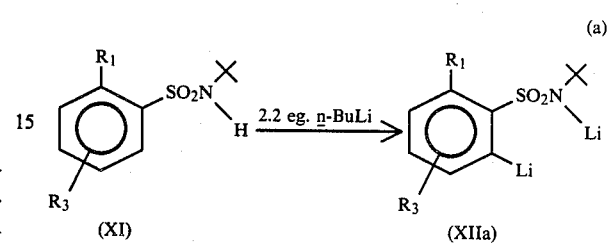

where $R_1$ is not $CH_2CO_2R_8$, $CO_2R_8$, $OSO_2R_{13}$ or $CH_2OR_{14}$;

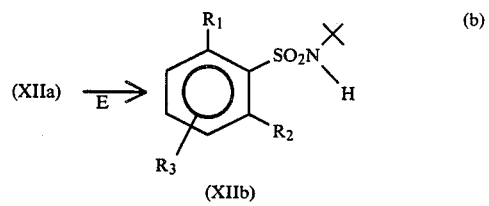

where $R_1$ is as defined above;

E is $R_5SSR_5$, $CO_2$, $$\overset{O}{\underset{}{ClCOR_8}}, \overset{O}{\underset{}{R_8OCOR_8}},$$

$CH_2O$, $CH_3I$, or $CH_3CH_2I$; and $R_2$ is $SR_5$, $CO_2H$, $CO_2R_8$, $CH_2OH$, $CH_3$ or $CH_2CH_3$.

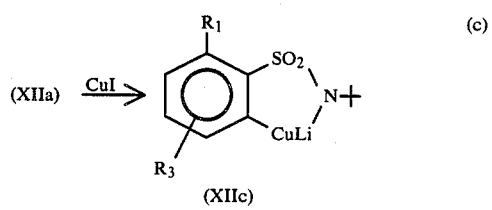

where $R_1$ is as defined above.

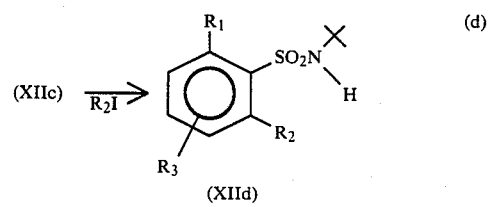

where $R_1$ is as defined above; and $R_2$ is $C_6H_4R_{11}$ or Q.

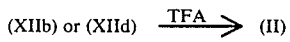 (e)

where
R₁ is $SR_5$, $CF_3$, $NR_6R_7$, $CO_2N(CH_3)_2$, $SO_2NR_9R_{10}$, $C_6H_4R_{11}$, OH, $CH_2OH$, Q or $$\begin{array}{c} CHCO_2R_8; \\ | \\ R_{12} \end{array}$$

$R_2$ is $SR_5$, $CO_2H$, $CO_2R_8$ or $CH_2OH$; and
$R_3$ is as defined in Equation 2.

Reaction step (8a) is best carried out under nitrogen in an inert anhydrous aprotic solvent such as tetrahydrofuran, diethyl ether or hexane at temperatures between −78° C. and 40° C. in a manner similar to that of J. G. Lombardino [*J. Org. Chem.*, 36, 1843 (1971)].

The preferred mode of addition is to add at least two equivalents of the alkyllithium or phenyllithium reagent to a −45° solution of the sulfonamide (XI) in tetrahydrofuran. After 15 minutes to 3 hours at room temperature, the lithium salt XIIa is obtained.

In Equation 8b, the reaction mixture is cooled to between 0° to −78° and a disulfide, carbon dioxide, chloroformate, dialkyl carbonate, formaldehyde, methyl iodide or ethyl iodide added to the lithium salt. The mixture is then allowed to warm and is stirred at ambient to reflux temperature for 6 to 20 hours. The addition of dilute acetic acid or ammonium chloride removes inorganic salts from the product contained in the organic phase to provide sulfonamides (XIIb).

In reaction 8c, XIIa is reacted with cuprous iodide at temperatures below 0° C., presumably forming XIIc. After 10 minutes to 1 hour, the aryl iodide or heterocyclic iodide is added and the mixture heated at reflux for 12 to 24 hours. After quenching the reaction with a dilute acid such as hydrochloric acid, ammonium hydroxide can be added in the presence of air to facilitate removal of the copper salts. The product may be extracted with solvents such as ethyl acetate or ether. The residue may be purified by chromatography or triturated using solvents such as hexane/chloroform or hexane/ether.

Several studies on the competition of substituents for ortho-direction capabilities indicates that for substituted sulfonamides, lithiation is directed to the position adjacent to the sulfonamide group:

D. W. Slocum and C. A. Jennings *J. Org. Chem.*, 41, 3653 (1976);

A. I. Meyers and K. Lutomski *J. Org. Chem.*, 44, 4464 (1979);

P. Beak and R. A. Brown *J. Org. Chem.*, 47, 34 (1982); and

P. Beak and V. Snieckus *Acc. Chem. Res.*, 15, 306 (1982).

For example, the metallation of (XIa) was found to occur in the 6-position. The absence of metallation at the 3 position or on the thiomethyl group attests to the powerful directing influence of the sulfonamide group and the thermodynamic stability of the resulting anion.

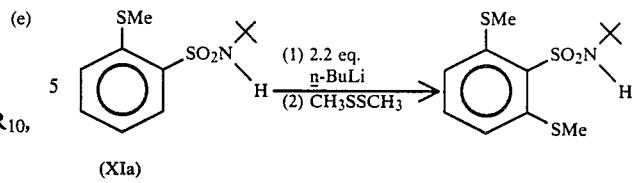

(XIa)

Reaction step (P8e) is best carried out in trifluoroacetic acid or ethanolic hydrogen chloride between ambient and reflux temperatures for 18 to 48 hours according to the method of J. G. Lombardino [*J. Org. Chem.*, 36, 1843 (1971)].

The deprotection appears to be concentration dependent. The yield of sulfonamide (II) can usually be increased by using a large excess of the acid as a solvent or by stripping off the by-products after 18 hours and redissolving or resuspending the residue in the acid of choice and stirring an additional 20 to 30 hours. The solvent is distilled off in vacuo and the residue can be triturated and recrystallized with solvents such as 1-chlorobutane or chloroform/hexane. The products can also be purified by chromatography.

Some sulfonamides (XIIe) are best prepared from (XIb) in a "one pot" sequence, an example of which is shown in Equation 8f.

Equation 8f

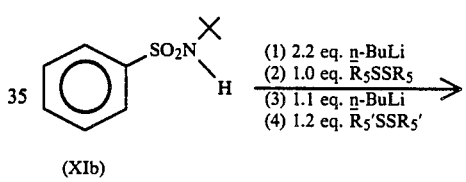

(XIb)

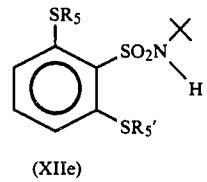

(XIIe)

where
$R_5$ and $R_5'$ are independently $C_1-C_3$ alkyl.

This reaction is best carried out in an inert atmosphere in an anhydrous aprotic solvent such as tetrahydrofuran, dimethylethylether or diethyl ether at temperatures between −78° and 40° C. in a manner similar to that described for Equation 8a.

The method of choice is to treat a −45° C solution of sulfonamide (XIb) in tetrahydrofuran sequentially with (1) 2.2 equivalents of alkyllithium at −45° C. followed by warming to room temperature and stirring for 2 hours, (2) 1.0 equivalent of dialkyl disulfide at 0° C. followed by warming to ambient temperature and stirring for 2 hours, (3) 1.1 equivalent of alkyllithium at −45° C. followed by warming to room temperature and stirring for 2 hours, and (4) 1.2 equivalents of dialkyl disulfide at 0° C. followed by stirring at ambient temperature for 18 hours.

The sulfonamides of Formula (XIIg) can be prepared from compounds of Formula (XIIf) as shown in Equation 8g.

Equation 8g

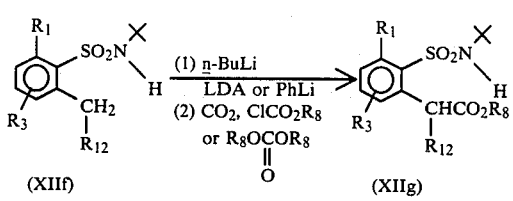

wherein
R$_1$ and R$_3$ are as described in Equation 8a;
R$_{12}$ is H or CH$_3$; and
R$_8$ is H, CH$_3$, CH$_2$CH$_3$ or CH$_2$CH$_2$CH$_3$.

The above reaction is best carried out at −45° to 0° under conditions described for Equations 8a and b. The lithiation of o-toluenesulfonamides and their subsequent reactions is described by H. Watanabe and C. R. Hauser [*J. Org. Chem.*, 33, 4278 (1968)].

The sulfonamides of Formula (XIIf) can be prepared as described in Equation 8b.

Many sulfonamides of Formula (XI) can be prepared from the corresponding sulfonyl chlorides in a manner similar to that taught by J. G. Lombardino [*J. Org. Chem.*, 36, 1843 (1971)] as shown below.

Equation 8h

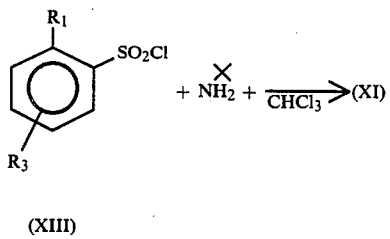

wherein
R$_1$ and R$_3$ are as defined in Equation 2.

The reaction of Equation 8h is accomplished by treating a 0° C. solution of at least two equivalents of t-butyl amine in a solvent such as chloroform with the sulfonyl chloride (XIII). The temperature is kept at 0° to 15° C. for 1 hour then raised to 50° to 80° C. and held at that temperature for 1 to 3 hours. This mixture is then poured into cold acid such as hydrochloric acid and extracted into a solvent such as methylene chloride or ethyl ether. Products are isolated by evaporation of the solvent and trituration of the solid residues with solvents such as hexane, chloroform or 1-chlorobutane.

The sulfonyl chlorides of Formula (XIII) have been disclosed. Certain sulfonyl chlorides are best prepared by chlorosulfonation of a substituted benzene according to the teaching of H. T. Clarke et al., *Org. Synth.* Coll. Vol. 1, 2nd Ed., 1941, p. 85. Other benzenesulfonyl chlorides are best prepared by diazotization of the appropriate aniline with sodium nitrite in HCl, followed by reaction of the diazonium salt with sulfur dioxide and cuprous chloride in acetic acid according to the teaching of H. L. Yale and F. Sowinski, *J. Org. Chem.*, 25, 1824 (1960). In addition, the oxidative chlorination of mercaptans to prepare sulfonyl chlorides is widely reported in the literature, e.g., Gilbert, "Sulfonation and Related Reactions, " pp. 202–214, Interscience Publishers, New York, 1965.

Sulfonamides of Formula (II) can also be prepared using the two step procedure shown in Equation 9.

Equation 9

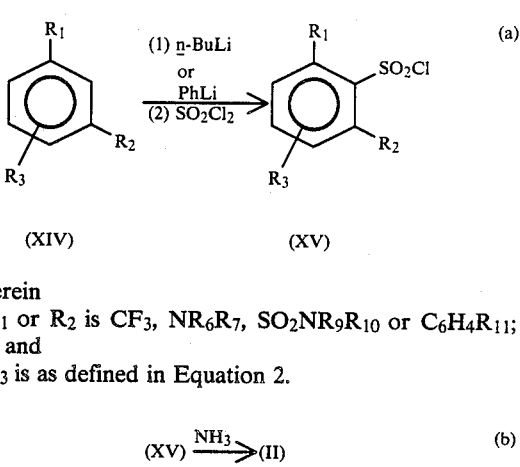

wherein
R$_1$ or R$_2$ is CF$_3$, NR$_6$R$_7$, SO$_2$NR$_9$R$_{10}$ or C$_6$H$_4$R$_{11}$; and
R$_3$ is as defined in Equation 2.

wherein
R$_1$, R$_2$ and R$_3$ are as defined above.

The reaction in Equation 9A is best carried out under nitrogen in an anhydrous, aprotic solvent such as tetrahydrofuran or diethyl ether with at least one equivalent of the alkyllithium at temperatures between −110° and −45° for 15 minutes to two hours. Sulfuryl chloride is then added and the mixture allowed to slowly warm to ambient temperature over the 1 to 4 hours. An aqueous wash removes inorganic salts and the product is obtained after evaporation of the solvent in vacuo. The crude sulfonyl chloride XV can be used without further purification. The reaction of sulfuryl chloride and phenyllithium is described by S. N. Bhattacharya et al. [*J. Chem. Soc. C.*, 1265 (1968)].

The initial site of lithiation depends on the directing ability of the various substituents. During metallation, acids are protected as amides and phenols are protected as tetrahydropyran ethers. Benzyl alcohols may be metallated by preparing the dianion as taught by D. Seebach [Agnew. Chem. Int. Ed. Engl. 17,521 (1978)]. In general, the highest degree of lithiation occurs between the more powerful directing groups. Thus, one skilled in the art may determine which isomer will predominate.

For example, metallation at the 2-position of several 1,3-substitued benzenes has been reported:

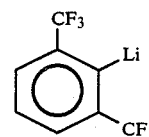

D. E. Grocock, et al.,
J. Chem. Soc., C. 3305 (1971).

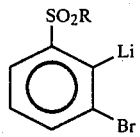

W. E. Truce and M. F. Amoo
J. Am. Chem. Soc., 73, 3013 (1951).

-continued

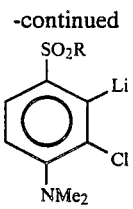

H.E. Zieger and G. Wittig
J. Org. Chem., 27, 3270 (1962).

The amination described in the reaction of Equation 9b is conveniently carried out by treating a solution of the sulfonyl chloride with at least two mole equivalents of anhydrous ammonia in a solvent such as ethyl ether or methylene chloride at $-20°$ to $30°$ C. If the sulfonamide product II is insoluble, it may be isolated by filtration followed by washing out the salts with water. If product II is soluble in the reaction solution, it may be isolated by filtering off the precipitated ammonium chloride and evaporation of the solvent. Alternatively, many sulfonamides II can be prepared by reaction of corresponding sulfonyl chlorides IX with excess aqueous ammonium hydroxide in tetrahydrofuran at $0°$ to about $40°$ C. for 0.5 to 10 hours. The sulfonamide product II is isolated by evaporation of the tetrahydrofuran solvent, addition of water to the residue and filtration.

In some cases the sulfonamides (II) are prepared from the sulfinic acid salts (XVI). The procedure of Equation 9c is well known in the art. See U.S. Pat. No. 4,127,405 and *Organic Reactions,* Vol. 26, 1979, J. Wiley and Sons, Inc., N.Y. Sulfonamides (II) are best prepared by treatment of sulfinic acid salts with chloramine. In this procedure an ethereal solution or suspension of the salt (XVI) is treated at low temperatures ($25°$ to $-30°$) with a dry ethereal solution of chloramine. The reaction is stirred for a period of several minutes to several hours. After filtration, the reaction mixture is washed with aqueous bisulfite and then dried and the solvent removed on a rotary evaporator. The crude product is further purified by usual methods such as crystallization or chromatography.

Equation 9c

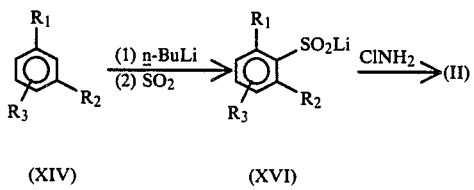

wherein $R_1$, $R_2$ and $R_3$ are as defined in Equation 9a.

Some sulfonamides (II) can be prepared from the corresponding nitro compounds as shown in Equation 10.

Equation 10

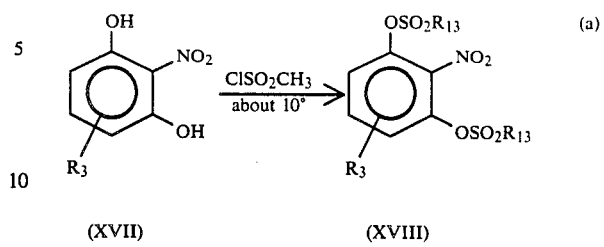

wherein
$R_3$ is as defined in Equation 2; and
$R_{13}$ is $C_1$-$C_3$ alkyl or $CF_3$.

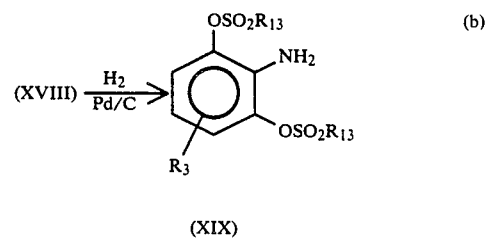

wherein
$R_3$ and $R_{13}$ are as defined above.

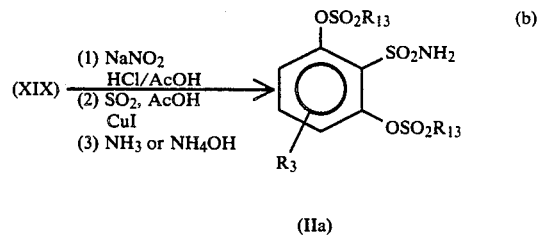

wherein
$R_3$ and $R_{13}$ are as defined above.

Reaction step 10a is best carried out in a solvent which will also act as an acid scavenger such as pyridine at temperatures below $10°$ C. during the addition of methanesulfonyl chloride. After 2 to 20 hours at ambient temperature, the products can be isolated by pouring the mixture into a cold solution of acid such as hydrochloric acid and washing the resulting precipitate with dilute acid.

The reduction in Equation 10b can be run by any of several methods in the literature. For example, the reaction can be run using catalytic reduction with 10% palladium-on-charcoal in an inert solvent such as methanol or tetrahydrofuran at $25°$ to $45°$ C. at 1 to 3 atmospheres of hydrogen. For details refer to a similar procedure described by M. Vincent, et al., *Bull. Soc. Chim. France,* 1580 (1962).

The reaction of Equation 10c is accomplished by treating a solution of amine such as (XIX) in a mixture of concentrated hydrochloric acid and glacial acetic acid with a solution of sodium nitrite in water at $-5°$ to $5°$ C. After stirring for 10–30 minutes at about $0°$ C. to insure complete diazotization, the solution is added to a mixture of an excess of sulfur dioxide and a catalytic amount of cuprous chloride or cupric chloride in glacial acetic acid at about $10°$ C. The temperature is kept at about 10° C. for ¼ to 1 hour, then raised to 20° to 30° C. and held at that temperature for 2 to about 24 hours. This solution is then poured into a large excess of ice water. The sulfonyl chloride XV can be isolated by filtration or by extraction into a solvent such as ethyl ether, methylene chloride or preferably, 1-chlorobutane, followed by evaporation of the solvent.

The amination is conveniently carried out as described for Equation 9b to provide sulfonamide (IIa).

Several heterocyclic sulfonamides (II) are conveniently prepared from the 2,6-disubstituted nitro compounds which are commercially available or described in Beilstein: for example, 2,6-dimethyl nitrobenzene; 2-nitro-3-methyl benzoic acid; and 2-nitro-3-methyl benzaldehyde.

The heterocyclic amines of Formula (V) in Equations 1a and 3 are also important intermediates for the preparation of the compounds of this invention, which can be prepared by the following methods.

The pyrimidines and triazines of Formula (Va) to (Vd) below are either known or can be prepared by obvious methods by one skilled in the art. For instance, the synthesis of pyrimidines and triazines of the general formula (Va) has been reviewed in "The Chemistry of Heterocyclic Compounds", a series published by Interscience Publishers, Inc., New York and London. 2-Aminopyrimidines are described by D. J. Brown in "The Pyrimidines", Vol. 16 of this series. 2-Amino-1,3,5-triazines are reviewed by E. M. Smolin and L. Rapaport in "s-Triazines and Derivatives", Vol. 13 of the same series. The synthesis of triazines is also described by F. C. Schaefer, U.S. Pat. No. 3,154,547 and by K. R. Huffman and F. C. Schaefer, J. Org. Chem., 28, 1812 (1963). The synthesis of the bicyclic amines (Vc) and (Vd) are described in EPO Publication No. 15,683, and that of (Vb) in European Patent Publication No. 46,677.

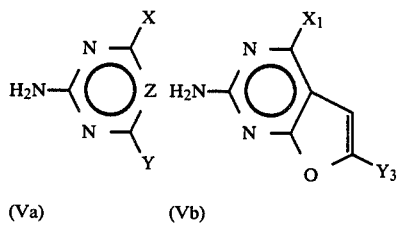

(Va)     (Vb)

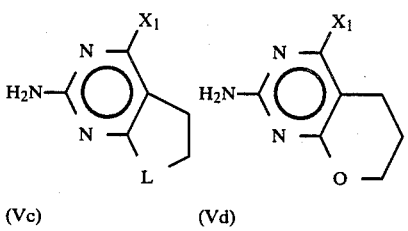

(Vc)     (Vd)

wherein
L, X, $X_1$, Y and Z are as originally defined.

Heating equimolar amounts of ethyl propionimidate hydrochloride and N-aminoguanidine nitrate in pyridine gives 3-amino-5-ethyltriazole; German Pat. No. 1,073,499 (1960); Berichte, 96, 1064 (1963).

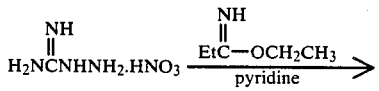

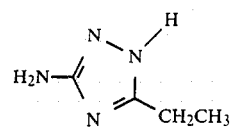

Condensation of hydrazine with ethyl N-cyanoacetimidate yields 3-amino-5-methyltriazole; Journal of Organic Chemistry, 28, 1816 (1963).

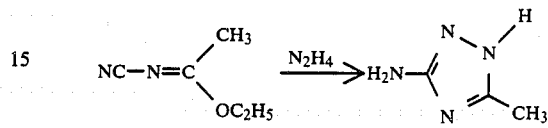

British Pat. No. 736,568 (1955) describes the synthesis of 3-amino-5-mercaptotriazole.

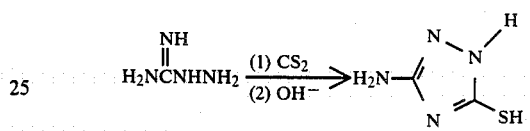

Condensing hydrazine with dimethyl cyanodithioimidocarbonate in acetonitrile gives 3-amino-5-methylthio-1,2,4-triazole while reaction of hydrazine with dimethyl N-cyanoimidocarbonate produces 3-amino-5-methoxy-1,2,4-triazole; Journal of Organic Chemistry, 39, 1522 (1974).

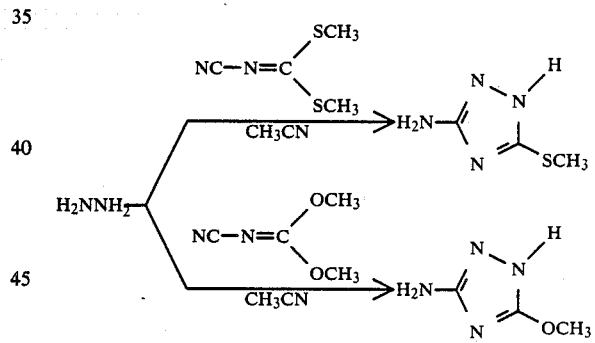

Reaction of substituted hydrazines with N-cyanothioimidocarbonates (prepared according to the procedure given in D. M. Wieland, Ph. D. Thesis, 1971, pp. 123-124) yields disubstituted aminotriazoles as shown below.

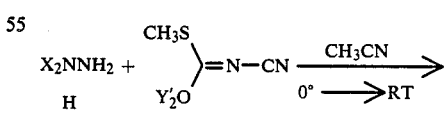

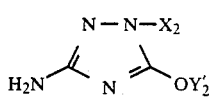

($Y_2'$ = $CH_3$ or $C_2H_5$)

Many of the aminoheterocyclic intermediates of Formula (V) where $R_4$ is methyl may be prepared by a two-step procedure as described for (VI) in Equation 11.

Equation 11

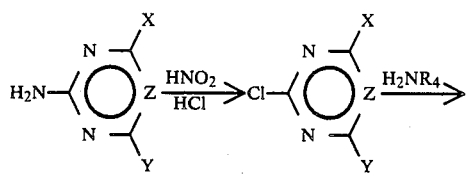

(XX)  (XXI)

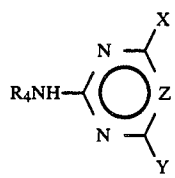

(VI)

wherein

X, Y and Z are as originally defined and $R_4$ is $CH_3$.

A solution of the amine (XX) in concentrated hydrochloric acid is treated with sodium nitrite solution and the chloro compound (XXI) is isolated in the usual manner by filtration of the acidic solution. A representative procedure is described by Bee and Rose in *J. Chem. Soc. C*, 2031 (1966), for the case in which $Z=CH$, and $X=Y=OCH_3$. Displacement of the chlorine of (XXI) may be accomplished by heating with an excess of methylamine in water to obtain the methylamino heterocycle (VI).

Equation 12 below illustrates the preparation of the required methyl pyrimidinyl carbamates and methyl triazinyl carbamates of Formula (III) in Equation 1. By obvious modifications, other methyl carbamates of Formula (III) may be prepared by this method by one skilled in the art.

Equation 12

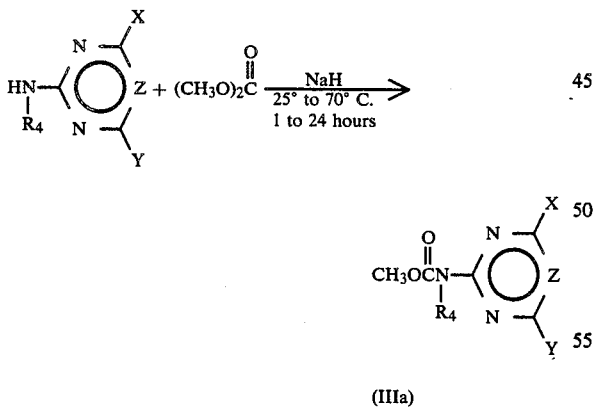

(IIIa)

wherein

X, Y and Z are as originally defined; and $R_4$ is H.

According to Equation 12, a heterocyclic amine is reacted with two equivalents of sodium hydride and excess dimethyl carbonate to form IIIa. The reaction is run in an inert solvent such as tetrahydrofuran at 25° C. to reflux for 1 to 24 hours. The product is isolated by (a) adding about two equivalents of concentrated hydrochloric acid under nitrogen at 0° to 30° C.; (b) filtering; and (c) separating out the organic phase, then drying (sodium sulfate and/or magnesium sulfate) and concentrating to dryness in vacuo. The product IIIa may be purified further by recrystallization or chromatography procedures.

Agriculturally suitable salts of compounds of Formula I are also useful herbicides and can be prepared in a number of ways known to the art. For example, metal salts can be made by treating compounds of Formula I with a solution of alkali or alkaline earth metal salt having a sufficiently basic anion (e.g., hydroxide, alkoxide, carbonate or hydride). Quaternary amine salts can be made by similar techniques.

Salts of compounds of Formula I can also be prepared by exchange of one cation to another. Cationic exchange can be effected by direct treatment of an aqueous solution of a salt of a compound of Formula I (e.g., alkali metal or quaternary amine salt) with a solution containing the cation to be exchanged. This method is most effective when the desired salt containing the exchanged cation is insoluble in water. e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is further illustrated by the following specific examples. Unless otherwise indicated, temperatures are in degrees centigrade.

EXAMPLE 1

N-[1,1-(Dimethylethyl)]-2-(methylthio)benzenesulfonamide (XIa; $R_1=SCH_3$, $R_3=H$)

To a mixture of 21.3 g (0.10 mol) of N-[1,1-(dimethylethyl)]benzenesulfonamide in 400 ml anhydrous tetrahydrofuran (THF) under nitrogen atmosphere was added 137 ml (0.22 mol) 1.6M butyllithium in hexanes dropwise at −40°. The mixture was then warmed to room temperature for 2 hours then recooled to −20° and treated with 10.8 ml (0.12 mol) methyl disulfide in 15 ml THF. After stirring overnight at ambient temperature, 80 ml of 10% hydrochloric acid was added and the layers separated. The aqueous phase was extracted with ether and the combined organic extracts washed with brine, dried, and evaporated to a solid. The residue was triturated with ether/hexanes and collected to afford 23.5 g of the title compound, m.p. 138°–140°.

NMR (CDCl$_3$): δ 1.20 (s, 9H); 2.58 (s, 3H); 5.39 (s, NH); 7.2–7.6 (m, 4H); and 8.02–8.27 (m, 1H) ppm.

EXAMPLE 2

N-(1,1-Dimethylethyl)-2-(methylthio)-6-phenylbenzenesulfonamide (XIId; $R_1=SCH_3$, $R_2=C_6H_5$, $R_3=H$)

A solution of 11.3 g (0.0436 mol) N-(1,1-dimethylethyl)-2-(methylthio)benzenesulfonamide in 300 ml tetrahydrofuran (THF) was treated with 60.5 ml (0.096 mol)

2M n-butyllithium in hexanes at −30° under a nitrogen atmosphere. The mixture was stirred for 1 hour at ambient temperature then recooled to −20° and treated with 8.3 g (0.0436 mol) of cuprous iodide (anhydrous). After 10 minutes at −15°, 4.9 ml (0.0438 mol) iodobenzene was added and the mixture was then heated to reflux overnight. Acetic acid (10 ml) was added after cooling the mixture to 15°, then 200 ml concentrated ammonium hydroxide plus 200 ml ethyl acetate was introduced and the mixture was stirred vigorously in the presence of air to facilitate removal of the copper salts. The aqueous phase was separated, extracted with more ethyl acetate and the combined organic extracts were washed successively with concentrated ammonium hydroxide, water and brine, then dried ($MgSO_4$) and evaporated to an oil. The product crystallized from ether/hexanes to afford 10 g of material, m.p. 162°–165°.

NMR ($CDCl_3$): δ 1.1 (s, 9H); 2.65 (s, 3H); 5.2 (s, NH); 7.2 (t, J=4 Hz, 1H); and 7.5 (m, 7H) ppm.

EXAMPLE 3

2,6-Bis(methylthio)-N-(1,1-dimethylethyl)benzenesulfonamide (XIIb; $R_1=R_2=SCH_3$, $R_3=H$)

Under nitrogen, a homogeneous solution of 80 g of N-(1,1-dimethylethyl)benzenesulfonamide in 1100 ml dry THF was cooled to −40° and 516 ml of 1.6M n-butyllithium added dropwise at this temperature. After the addition was complete, the reaction mixture was allowed to warm to room temperature and stirred for 2 hours. The resulting thick ppt. was cooled to 0° and 38 ml of methyl disulfide added dropwise. After warming to room temperature, the suspension was stirred for 1.5 hour. It was then cooled to −40° and an additional 285 ml n-butyllithium added dropwise. The suspension was allowed to warm to 25° C. and stirred at this temperature for 2 hours. Cooling to 0° and the dropwise addition of 41 ml of methyl disulfide gave a bright orange suspension. After stirring at room temperature for 18 hours, the white suspension was cooled to 0° and 20 ml of saturated ammonium chloride added dropwise. The mixture was poured into 1 l of water and extracted with ether. An insoluble precipitate remained which was collected by filtration and air dried to provide 42.3 g of 2,6-bis(methylthio)-N-(1,1-dimethylethyl)benzenesulfonamide as a white powder, m.p. 182°–185°.

The combined ether extracts were washed twice with water, once with brine and dried over sodium sulfate. Concentration gave a pale yellow solid which was washed with n-butyl chloride, providing an additional 34.5 g of the title compound, m.p. 174°–184°.

NMR (DMSO-$d_6$): δ 1.11 (s, 9, t-Bu); 2.48 (s, 6, $SCH_3$); and 7.12–7.65 (m, 4).

IR (nujol): 3.05 (NH).

EXAMPLE 4

2-(Methylthio)-6-phenylbenzenesulfonamide (II; $R_1=SCH_3$, $R_2=C_6H_5$, $R_3=H$)

In a mixture of 75 ml trifluoroacetic acid plus 2 ml water was dissolved 10 g (0.030 mol) of N-(1,1-dimethylethyl)-2-(methylthio)-6-phenylbenzenesulfonamide and heated to 85°. After 15 minutes the mixture was cooled and evaporated, then diluted with water and extracted with methylene chloride. The methylene chloride was washed with saturated sodium bicarbonate solution, dried ($MgSO_4$), evaporated in vacuo and crystallized from ether/hexanes to afford 6.5 g of the title compound, m.p. 167°–168°.

NMR ($CDCl_3$): δ 2.55 (s, 3H); 6.62 (2, $NH_2$); 7.07 (m, 1H); and 7.35–7.55 (m, 7H) ppm.

EXAMPLE 5

2-(Methylsulfonyl)-6-phenylbenzenesulfonamide (II; $R_1=SO_2CH_3$, $R_2=C_6H_5$, $R_3=H$)

A solution of 6.5 g (0.023 mol) 2-(methylthio)-6-phenylbenzenesulfonamide in 100 ml methylene chloride plus 20 ml ethyl acetate was treated with 10 g (0.046 mol) 80% m-chloroperoxybenzoic acid. The mixture was subsequently stirred at ambient temperature for 3 days then filtered. The solids were rinsed with saturated sodium bicarbonate, water and more methylene chloride. A second crop was obtained from the combined bicarbonate washed methylene chloride filtrates to afford 6.9 g of the title compound, m.p. 258°–259°.

NMR ($CDCl_3$/DMSO-$d_6$): δ 3.50 (s, 3H); 6.95 (s, $NH_2$); 7.47 (s, 5H); 7.5–7.98 (m, 3H); and 8.42 (m, 1H) ppm.

EXAMPLE 6

N-[(4-Methoxy-6-methylpyrimidin-2-yl)aminocarbonyl]-3-(methylsulfonyl)-1,1'-biphenyl-2-sulfonamide (I; $R_1=SO_2CH_3$, $R_2=C_6H_5$, $R_3=R_4=H$, A=A-1, X=$OCH_3$, Y=$CH_3$, Z=CH)

To a stirred suspension of 1.2 g (3.86 mmol) 2-(methylsulfonyl)-6-phenylbenzenesulfonamide in 35 ml methylene chloride under nitrogen atmosphere was added 2.5 ml (5 mmol) of 2M trimethylaluminum in toluene via syringe at ambient temperature. Solid methyl N-(4-methoxy-6-methylpyrimidin-2-yl)carbamate (0.95 g, 4.8 mmol) was then added and the mixture was heated to reflux for 1 day. Aqueous 5% hydrochloric acid (50 ml) was added to the cooled mixture followed by ether. The solid product which separated was collected and rinsed with ether and water, then chromatographed on silica gel with 10% ethyl acetate in methylene chloride as the eluant. Trituration of the solid product with ether/hexanes afforded 0.32 g of the title compound, m.p. 206°–208°.

NMR ($CDCl_3$/DMSO-$d_6$): δ 2.30 (s, 3H); 3.60 (s, 3H); 3.88 (s, 3H); 6.27 (s, 1H); 7.15–7.9 (m, 7H); 8.4 (sbr, NH); 8.45 (m, 1H); and 12.3 (sbr, NH) ppm.

IR (nujol): 1700, 3250 $cm^{-1}$.

EXAMPLE 7

2,6-Bis(methylthio)benzenesulfonamide (II; $R_1=R_2=SCH_3$; $R_3=H$)

A brown solution of 70 g of 2,6-bis(methylthio)-N-(1,1-dimethylethyl)benzenesulfonamide in 200 ml trifluoroacetic acid was stirred at room temperature. After 10 minutes, a heavy precipitate formed, the suspension was stirred for 18 hours. The resulting solid was collected by filtration and dissolved in 10% NaOH, filtered and the filtrate acidified with 10% HCl. The precipitated solid was washed with water and air dried to provide 48 g of 2,6-bis(methylthio)benzenesulfonamide, m.p. 197°–199°.

NMR (DMSO-$d_6$): δ 2.48 (s, 6, $SCH_3$); and 7.12–7.62 (m, 5).

IR (nujol): 2.90 and 3.00 ($NH_2$).

EXAMPLE 8

2,6-Bis(Methylthio)-N-(butylaminocarbonyl)benzenesulfonamide (IX; $R_1=R_2=SCH_3$, $R_3=H$)

A stirred suspension of 5.0 g (0.02 mol) of 2,6-bis(methylthio)benzenesulfonamide, 8.3 g (0.06 mol) potassium carbonate and 3.4 ml (0.03 mol) n-butyl isocyanate was heated at reflux for four hours. After stirring at 25° overnight, the mixture was poured into ice and 30 ml 10% HCl. The resulting precipitate was collected, washed several times with water and air dried to provide 6.5 g of the title compound, m.p. 151°–154°.

NMR (DMSO-$d_6$): δ 0.50–1.00 (m, 3); 1.00–1.47 (m, 4); 2.43 (s, 6); 2.67–3.15 (m, 2); 6.18–6.56 (m, 1); and 7.10–7.75 (m, 3).

IR (nujol): 3.00 (NH); and 5.95 (c=o).

EXAMPLE 9

2,6-Bis(methylthio)-N-[(4-chloro-6-methoxypyrimidin-2-yl)aminocarbonyl]benzenesulfonamide (I; $R_1=R_2=SCH_3$, $R_3=H$, A=A-1, X=Cl, Y=OCH$_3$, Z=CH)

A suspension of 2.3 g (6.7 mmol) of 2,6-bis(methylthio)-N-(butylaminocarbonyl)benzenesulfonamide and 0.07 g (0.67 mmol) of DABCO in 30 ml xylene was heated to 140°. To the resulting solution, phosgene (1.9 ml, 16 mmol) was added dropwise at 135° to 140° C. The mixture was heated at reflux for 2 hours, cooled and the solvent removed in vacuo. The resulting solid was dissolved in 50 ml methylene chloride under $N_2$ and 1.37 g (8.6 mmol) 2-amino-4-chloro-6-methylpyrimidine added with 0.01 g (0.1 mmol) of DABCO. The mixture was stirred overnight and the solvent removed in vacuo. The residue was triturated with 1-chlorobutane. The resulting solid was dissolved in cold 1% NaOH, filtered and precipitated with 10% HCl washed with water and air dried to provide 0.46 g of the title compound, m.p. 179°–180° C.

NMR (DMSO-$d_6$): δ 2.48 (s, 6, SCH$_3$); 4.00 (s, 3, OCH$_3$); 6.90 (s, 1, ArH); 7.18–7.79 (m, 3, ArH); 10.88 (brs, 1, NH); and 12.48 (brs, 1, NH).

IR (nujol): 5.80 (c=o).

Following the procedures described above, the compounds in Tables 1–15 can be prepared. In these tables, some variables are defined twice, there being a different definition when Z=CH and when Z=N. Thus, for example, in the thirteenth row in Table 3, X is defined as Cl, but, when Z=N (definition a), then X is defined as OCF$_2$H. Similarly, in Tble 3 and the following tables, when a row is followed by a superscript, those substituent definitions apply only when Z has the definition denoted by the superscript.

TABLE 1

$$\text{(Ar)}\text{-SO}_2\text{NHCNH-A}$$
with $R_1$, $R_2$, $R_3$ substituents and C=O

| $R_1$ | $R_2$ | $R_3$ | A | L | $X_1$ | $Y_1$ | $X_2$ | $Y_2$ | $Y_3$ |
|---|---|---|---|---|---|---|---|---|---|
| SO$_2$CH$_3$ | C$_6$H$_5$ | H | A-2 | O | CH$_3$ | — | — | — | — |
| SO$_2$CH$_3$ | C$_6$H$_5$ | H | A-2 | O | OCH$_3$ | — | — | — | — |
| SO$_2$CH$_3$ | C$_6$H$_5$ | H | A-2 | CH$_2$ | CH$_3$ | — | — | — | — |
| SO$_2$CH$_3$ | C$_6$H$_5$ | H | A-2 | CH$_2$ | OCH$_3$ | — | — | — | — |
| SCH$_3$ | SCH$_3$ | H | A-2 | O | CH$_3$ | — | — | — | — |
| SCH$_3$ | SCH$_3$ | H | A-2 | O | OCH$_3$ | — | — | — | — |
| SO$_2$CH$_3$ | C$_6$H$_5$ | H | A-2 | O | Cl | — | — | — | — |
| SO$_2$CH$_3$ | C$_6$H$_5$ | H | A-2 | O | OCF$_2$H | — | — | — | — |
| SO$_2$CH$_3$ | C$_6$H$_5$ | H | A-3 | — | CH$_3$ | — | — | — | — |
| SO$_2$CH$_3$ | C$_6$H$_5$ | H | A-3 | — | OCH$_3$ | — | — | — | — |
| SO$_2$CH$_3$ | C$_6$H$_5$ | H | A-3 | — | Cl | — | — | — | — |
| SO$_2$CH$_3$ | C$_6$H$_5$ | H | A-3 | — | OCF$_2$H | — | — | — | — |
| SCH$_3$ | SCH$_3$ | H | A-3 | — | OCH$_3$ | — | — | — | — |
| SCH$_3$ | SCH$_3$ | H | A-3 | — | CH$_3$ | — | — | — | — |
| SO$_2$CH$_3$ | C$_6$H$_5$ | H | A-4 | — | CH$_3$ | — | — | — | CH$_3$ |
| SO$_2$CH$_3$ | C$_6$H$_5$ | H | A-4 | — | OCH$_3$ | — | — | — | CH$_3$ |
| SO$_2$CH$_3$ | C$_6$H$_5$ | H | A-4 | — | Cl | — | — | — | H |
| SO$_2$CH$_3$ | C$_6$H$_5$ | H | A-4 | — | OCF$_2$H | — | — | — | CH$_3$ |
| SCH$_3$ | SCH$_3$ | H | A-4 | — | OCH$_3$ | — | — | — | CH$_3$ |
| SCH$_3$ | SCH$_3$ | H | A-4 | — | CH$_3$ | — | — | — | H |
| SO$_2$CH$_3$ | C$_6$H$_5$ | H | A-5 | — | — | CH$_3$ | — | — | — |
| SO$_2$CH$_3$ | C$_6$H$_5$ | H | A-5 | — | — | OCH$_3$ | — | — | — |
| SCH$_3$ | SCH$_3$ | H | A-5 | — | — | CH$_3$ | — | — | — |
| SCH$_3$ | SCH$_3$ | H | A-5 | — | — | OCH$_3$ | — | — | — |
| SO$_2$CH$_3$ | C$_6$H$_5$ | H | A-6 | — | — | — | CH$_3$ | CH$_3$ | — |
| SO$_2$CH$_3$ | C$_6$H$_5$ | H | A-6 | — | — | — | CH$_3$ | OCH$_3$ | — |
| SO$_2$CH$_3$ | C$_6$H$_5$ | H | A-6 | — | — | — | CH$_3$ | SCH$_3$ | — |
| SO$_2$CH$_3$ | C$_6$H$_5$ | H | A-6 | — | — | — | CH$_2$CH$_3$ | CH$_3$ | — |
| SO$_2$CH$_3$ | C$_6$H$_5$ | H | A-6 | — | — | — | CH$_2$CH$_3$ | OCH$_3$ | — |
| SO$_2$CH$_3$ | C$_6$H$_5$ | H | A-6 | — | — | — | CH$_2$CH$_3$ | SCH$_3$ | — |
| SO$_2$CH$_3$ | C$_6$H$_5$ | H | A-6 | — | — | — | CH$_2$CF$_3$ | CH$_3$ | — |
| SO$_2$CH$_3$ | C$_6$H$_5$ | H | A-6 | — | — | — | CH$_2$CF$_3$ | OCH$_3$ | — |
| SCH$_3$ | SCH$_3$ | H | A-6 | — | — | — | CH$_3$ | CH$_3$ | — |
| SCH$_3$ | SCH$_3$ | H | A-6 | — | — | — | CH$_3$ | OCH$_3$ | — |

TABLE 2a $$\text{structure: } R_1, R_2, R_3\text{-substituted phenyl-}SO_2NHCONH\text{-pyrimidine with X and Y substituents}$$

| $R_1$ | $R_2$ | $R_3$ | X | Y | m.p. (°C.) |
|---|---|---|---|---|---|
| $SCH_3$ | $SCH_2CH_3$ | H | $CH_3$ | $OCH_3$ | |
| $SCH_2CH_3$ | $SCH_2CH_3$ | 3-Cl | $CH_3$ | $OCH_3$ | |
| $SCH_2CH_3$ | $SCH_2CH_2CH_3$ | H | $OCH_3$ | $OCH_3$ | |
| $SCH_2CH_2CH_3$ | $SCH_2CH_2CH_3$ | H | $CH_3$ | $OCH_3$ | |
| $S(O)CH_3$ | $SCH_3$ | H | $CH_3$ | $CH_3$ | |
| $S(O)_2CH_3$ | $SCH_3$ | H | $CH_3$ | $OCH_3$ | |
| $S(O)CH_3$ | $S(O)CH_3$ | H | $OCH_3$ | $OCH_3$ | |
| $S(O)_2CH_3$ | $S(O)CH_3$ | H | Cl | $OCH_3$ | |
| $SCH_3$ | $N(CH_3)_2$ | H | $CH_3$ | $OCH_3$ | |
| $S(O)CH_3$ | $N(CH_3)_2$ | H | $OCH_3$ | $OCH_3$ | |
| $S(O)_2CH_3$ | $N(CH_3)_2$ | H | Cl | $OCH_3$ | |
| $SCH_3$ | $N(CH_3)CH_2CH_3$ | 3-F | $CH_3$ | $OCH_3$ | |
| $SCH_3$ | $N(CH_2CH_3)_2$ | H | $OCH_3$ | $OCH_3$ | |
| $CF_3$ | $CF_3$ | H | $CH_3$ | $OCH_3$ | |
| $CF_3$ | $CF_3$ | 4-Br | $CH_3$ | $CH_3$ | |
| $N(CH_3)_2$ | $N(CH_3)_2$ | H | $CH_3$ | $OCH_3$ | |
| $N(CH_3)CH_2CH_3$ | $N(CH_3)_2$ | H | $OCH_3$ | $OCH_3$ | |
| $N(CH_2CH_3)_2$ | $N(CH_3)_2$ | 4-$CH_3$ | $CH_3$ | $OCH_3$ | |
| $N(CH_3)CH_2CH_3$ | $N(CH_3)CH_2CH_3$ | H | $OCH_3$ | $OCH_3$ | |
| $N(CH_2CH_3)_2$ | $N(CH_2CH_3)_2$ | H | Cl | $OCH_3$ | |
| $N(CH_3)_2$ | $C_6H_5$ | H | $CH_3$ | $OCH_3$ | |
| $N(CH_3)_2$ | 2'-$C_6H_4Cl$ | H | Cl | $OCH_3$ | |
| $N(CH_3)_2$ | $CH_2CO_2CH_3$ | H | $CH_3$ | $CH_3$ | |
| $N(CH_3)_2$ | $CH_2CO_2CH_2CH_3$ | H | $CH_3$ | $OCH_3$ | |
| $N(CH_3)_2$ | $CH_2CO_2CH_2CH_2CH_3$ | H | Cl | $OCH_3$ | |
| $N(CH_3)_2$ | $CH_2CO_2CH_2CH=CH_2$ | H | $OCH_3$ | $OCH_3$ | |
| $N(CH_3)_2$ | $CH_2CO_2CH_2CH_2Cl$ | 5-$OCH_3$ | $CH_3$ | $CH_3$ | |
| $N(CH_3)_2$ | $CH_2CO_2CH_2CH_2OCH_3$ | H | $CH_3$ | $CH_3$ | |
| $N(CH_3)_2$ | $CH(CH_3)CO_2CH_3$ | H | $CH_3$ | $OCH_3$ | |
| $N(CH_3)_2$ | $CH(CH_3)CO_2CH_2CH=CH_2$ | H | $OCH_3$ | $OCH_3$ | |
| $N(CH_3)_2$ | $OSO_2CH_3$ | H | $CH_3$ | $OCH_3$ | |
| $N(CH_3)_2$ | $OSO_2CH_2CH_3$ | 3-$CF_3$ | Cl | $OCH_3$ | |
| $N(CH_3)_2$ | $OSO_2CH_2CH_2CH_3$ | H | $CH_3$ | $OCH_3$ | |
| $N(CH_3)_2$ | $OSO_2CF_3$ | H | $OCH_3$ | $OCH_3$ | |
| $N(CH_3)_2$ | $CH_2OCH_3$ | H | $CH_3$ | $OCH_3$ | |
| $N(CH_3)_2$ | $CH_2OCH_2CH_3$ | H | $CH_3$ | $CH_3$ | |
| $N(CH_3)_2$ | $CH_2OCH_2CH_2CH_3$ | H | $OCH_3$ | $OCH_3$ | |
| $N(CH_3)_2$ | $CH_2OCF_2H$ | H | $CH_3$ | $OCH_3$ | |
| $CO_2CH_3$ | $SO_2N(CH_3)_2$ | H | $CH_3$ | $OCH_3$ | |
| $CO_2CH_3$ | $SO_2N(CH_3)OCH_3$ | H | $CH_3$ | $CH_3$ | |
| $CO_2CH_2CH_2Cl$ | $SO_2N(CH_3)_2$ | H | $OCH_3$ | $OCH_3$ | |
| $CO_2CH_3$ | $C_6H_5$ | H | $CH_3$ | $CH_3$ | |
| $CO_2CH_3$ | 2'-$C_6H_4OCH_3$ | H | $OCH_3$ | $OCH_3$ | |
| $CO_2CH_2CH_2CH_3$ | 3'-$C_6H_4CH_3$ | H | $CH_3$ | $CH_3$ | |
| $CO_2CH_3$ | $CH_2CO_2CH_3$ | H | $CH_3$ | $OCH_3$ | |
| $CO_2CH_2CH_2Cl$ | $CH(CH_3)CO_2CH_3$ | H | $OCH_3$ | $OCH_3$ | |
| $CO_2CH_3$ | $CH_2OCH_3$ | H | $CH_3$ | $OCH_3$ | |
| $CO_2CH_3$ | $CH_2OCF_2H$ | H | $OCH_3$ | $OCH_3$ | |
| $SO_2N(CH_3)_2$ | $SO_2N(CH_3)_2$ | H | $CH_3$ | $CH_3$ | |
| $SO_2N(CH_3)OCH_3$ | $SO_2N(CH_3)_3$ | H | $OCH_3$ | $OCH_3$ | |
| $SO_2N(CH_3)OCH_3$ | $SO_2N(CH_3)OCH_3$ | H | $CH_3$ | $CH_3$ | |
| $SO_2N(CH_3)_2$ | $C_6H_5$ | H | $OCH_3$ | $OCH_3$ | |
| $SO_2N(CH_3)_2$ | 4'-$C_6H_4Cl$ | H | $CH_3$ | $OCH_3$ | |
| $SO_2N(CH_3)_2$ | 2'-$C_6H_4OCH_3$ | H | $OCH_3$ | $OCH_3$ | |
| $SO_2N(CH_3)_2$ | $CH_2CO_2CH_3$ | H | $CH_3$ | $OCH_3$ | |
| $SO_2N(CH_3)_2$ | $CH(CH_3)CO_2CH_3$ | H | $CH_3$ | $CH_3$ | |

TABLE 2a-continued

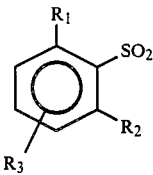

| R₁ | R₂ | R₃ | X | Y | m.p. (°C.) |
|---|---|---|---|---|---|
| SO₂N(CH₃)₂ | OSO₂CH₃ | H | CH₃ | OCH₃ | |
| SO₂N(CH₃)₂ | OSO₂CF₃ | H | OCH₃ | OCH₃ | |
| C₆H₅ | C₆H₅ | H | CH₃ | OCH₃ | |
| C₆H₅ | 2'-C₆H₄Cl | H | OCH₃ | OCH₃ | |
| C₆H₅ | 3'-C₆H₄Cl | H | CH₃ | OCH₃ | |
| 2-ClC₆H₄– | 2-ClC₆H₄– | H | OCH₃ | OCH₃ | |
| 2-ClC₆H₄– | 3-MeC₆H₄– | H | CH₃ | CH₃ | |
| C₆H₅ | CH₂CO₂CH₃ | H | CH₃ | OCH₃ | |
| C₆H₅ | —CH(CH₃)CO₂CH₃ | H | OCH₃ | OCH₃ | |
| 2'-C₆H₄CH₃ | CH₂CO₂CH₃ | H | Cl | OCH₃ | |
| C₆H₅ | OSO₂CH₃ | H | CH₃ | OCH₃ | |
| C₆H₅ | OSO₂CF₃ | H | CH₃ | OCH₃ | |
| 2'-C₆H₄F | OSO₂CH₂CH₃ | H | OCH₃ | OCH₃ | |
| C₆H₅ | CH₂OCH₃ | H | CH₃ | OCH₃ | |
| 4'-C₆H₄Cl | CH₂OCF₂H | H | CH₃ | OCH₃ | |
| CH₂CO₂CH₃ | CH₂CO₂CH₃ | 3-CH₃ | CH₃ | OCH₃ | |
| CH₂CO₂CH₃ | CH₂CO₂CH₂CH₂Cl | H | CH₃ | OCH₃ | |
| CH₂CO₂CH₂CH₂OCH₃ | CH₂CO₂CH₂CH=CH₂ | H | CH₃ | OCH₃ | |
| CH(CH₃)CO₂CH₃ | CH₂CO₂CH₃ | H | OCH₃ | OCH₃ | |
| CH(CH₃)CO₂CH₂CH₂Cl | CH₂CO₂CH₃ | H | CH₃ | CH₃ | |
| CH(CH₃)CO₂CH₃ | CH(CH₃)CO₂CH₃ | H | OCH₃ | CH₃ | |
| CH₂CO₂CH₃ | OSO₂CH₃ | H | OCH₃ | OCH₃ | |
| CH(CH₃)CO₂CH₃ | OSO₂CF₃ | H | CH₃ | OCH₃ | |
| CH₂CO₂CH₃ | CH₂OCH₃ | H | CH₃ | OCH₃ | |
| CH(CH₃)CO₂CH₃ | CH₂OCF₂H | H | CH₃ | CH₃ | |
| OSO₂CH₃ | OSO₂CH₃ | H | CH₃ | OCH₃ | |
| OSO₂CF₃ | OSO₂CH₃ | H | CH₃ | CH₃ | |
| OSO₂CF₃ | OSO₂CF₃ | H | CH₃ | CH₃ | |
| OSO₂CH₃ | CH₂OCH₃ | 4-CF₃ | CH₃ | OCH₃ | |
| OSO₂CF₃ | CH₂OCH₃ | H | OCH₃ | OCH₃ | |
| OSO₂CH₃ | CH₂OCF₂H | H | CH₃ | OCH₃ | |
| OSO₂CF₃ | CH₂OCF₂H | 5-Cl | CH₃ | CH₃ | |
| CH₂OCH₃ | CH₂OCH₃ | H | CH₃ | OCH₃ | |
| CH₂OCF₂H | CH₂OCH₃ | H | OCH₃ | OCH₃ | |

TABLE 2a-continued

[Structure: benzene ring with R1, R2, R3 substituents, SO2NHCONH linker to pyrimidine ring with X and Y substituents]

| R₁ | R₂ | R₃ | X | Y | m.p. (°C.) |
|---|---|---|---|---|---|
| CH₂OCF₂H | CH₂OCF₂H | H | CH₃ | CH₃ | |
| SO₂CH₃ | C₆H₅ | H | CH₃ | CH₃ | 228–230° d |
| SO₂CH₃ | C₆H₅ | H | CH₃ | OCH₃ | 206–208° d |
| SO₂CH₃ | C₆H₅ | H | CH | CF₃ | |
| SO₂CH₃ | C₆H₅ | H | CH₃ | CH₂OCH₃ | |
| SO₂CH₃ | C₆H₅ | 3-Cl | CH₃ | CH₂OCH₃ | |
| SCH₃ | SCH₃ | H | CH₃ | CH₃ | 188–194° |
| SCH₃ | SCH₃ | H | CH₃ | OCH₃ | 206–208° |
| SCH₃ | SCH₃ | H | CH₃ | CF₃ | |
| SCH₃ | SCH₃ | H | CH₃ | H | |
| SCH₃ | SCH₃ | H | CH₃ | NH₂ | |
| SCH₃ | SCH₃ | H | CH₃ | NHCH₃ | |
| SCH₃ | SCH₃ | H | CH₃ | N(CH₃)₂ | |
| SCH₃ | SCH₃ | H | CH₃ | CH₂CH₃ | |
| SCH₃ | SCH₃ | H | CH₃ | CH₂OCH₂CH₃ | |
| SCH₃ | SCH₃ | H | CH₃ | OCH₂CH₃ | |
| SCH₃ | SCH₃ | 5-CF₃ | CH₃ | OCH₂CH₃ | |
| SCH₃ | SCH₃ | H | CH₃ | SCH₃ | |
| SCH₃ | SCH₃ | H | CH₃ | OCH₂CH=CH₂ | |
| SCH₃ | SCH₃ | H | CH₃ | OCH₂C≡CH | |
| SCH₃ | SCH₃ | H | CH₃ | OCH₂CH₂F | |
| SCH₃ | C₆H₅ | H | CH₃ | OCH₂CH₂Cl | |
| SCH₃ | C₆H₅ | H | CH₃ | OCH₂CH₂Br | |
| SCH₃ | SCH₃ | 3-Cl | CH₃ | OCH₃ | |
| SCH₃ | SCH₃ | 3-CH₃ | CH₃ | OCH₃ | |
| SO₂CH₃ | 2'-C₆H₄Cl | H | CH₃ | OCH₃ | |
| SO₂CH₃ | C₆H₅ | 3-Cl | CH₃ | OCH₃ | |
| SO₂CH₃ | C₆H₅ | 5-Cl | CH₃ | OCH₃ | |
| SO₂CH₃ | C₆H₅ | H | OCH₃ | CF₃ | |
| SO₂CH₃ | C₆H₅ | H | OCH₃ | CH₂OCH₃ | |
| SO₂CH₃ | C₆H₅ | H | OCH₃ | OCH₃ | 212–214° |
| SO₂CH₃ | C₆H₅ | H | OCH₃ | OCH₂CF₃ | |
| SCH₃ | SCH₃ | H | OCH₃ | CF₃ | |
| SCH₃ | SCH₃ | H | OCH₃ | OCH₃ | 220–225° |
| SCH₃ | SCH₃ | H | OCH₃ | CH₂OCH₃ | |
| SCH₃ | SCH₃ | 3-Cl | CH₃ | OCH₃ | |
| SCH₃ | SCH₃ | 3-OCH₃ | OCH₃ | OCH₃ | |
| SCH₃ | SCH₃ | H | OCH₃ | N(CH₃)₂ | |
| SCH₃ | SCH₃ | H | OCH₃ | CH₂CH₃ | |
| SCH₃ | SCH₃ | H | OCH₃ | SCH₃ | |
| SO₂CH₃ | C₆H₅ | H | Cl | NH₂ | |
| SO₂CH₃ | C₆H₅ | H | Cl | NHCH₃ | |
| SO₂CH₃ | C₆H₅ | H | Cl | N(CH₃)₂ | |
| SO₂CH₃ | C₆H₅ | H | Cl | OCH₃ | |
| SCH₃ | SCH₃ | H | Cl | OCH₃ | 179–186° |
| SCH₃ | SCH₃ | H | Cl | N(CH₃)₂ | |
| SCH₃ | SCH₃ | 3-Cl | CH₃ | OCH₃ | |
| SCH₃ | SCH₃ | 3-CH₃ | OCH₃ | OCH₃ | |
| SO₂CH₃ | C₆H₅ | H | OCH₂CH₃ | H | |
| SO₂CH₃ | C₆H₅ | H | OCH₂CH₃ | CH₃ | |
| SO₂CH₃ | C₆H₅ | H | OCH₂CH₃ | CF₃ | |
| SO₂CH₃ | C₆H₅ | H | OCH₂CH₃ | CH₂OCH₃ | |
| SCH₃ | SCH₃ | H | OCH₂CH₃ | CH₃ | |
| SCH₃ | SCH₃ | H | OCH₂CH₃ | CF₃ | |
| SCH₃ | SCH₃ | 3-OCH₃ | OCH₂CH₃ | CH₃ | |
| SO₂CH₃ | C₆H₅ | H | F | OCH₃ | |
| SO₂CH₃ | C₆H₅ | H | F | NH₂ | |
| SO₂CH₃ | C₆H₅ | H | F | NHCH₃ | |
| SO₂CH₃ | C₆H₅ | H | F | N(CH₃)₂ | |
| SCH₃ | SCH₃ | H | F | OCH₃ | |
| SCH₃ | SCH₃ | H | F | N(CH₃)₂ | |
| SCH₃ | C₆H₅ | H | CH₃ | CH₃ | 218–221° d |
| SCH₃ | C₆H₅ | H | CH₃ | OCH₃ | 170–173° |
| SCH₃ | C₆H₅ | H | OCH₃ | OCH₃ | 187–189° |

TABLE 2b $$\text{structure: benzene ring with } R_1 \text{ (ortho), } SO_2NHCONH- \text{ group connected to pyrimidine ring with X and Y substituents, } R_2 \text{ and } R_3 \text{ on benzene}$$

| $R_1$ | $R_2$ | $R_3$ | X | Y | m.p. (°C.) |
|---|---|---|---|---|---|
| $SCH_3$ | $SCH_2CH_3$ | H | $CH_3$ | $OCH_3$ | |
| $SCH_2CH_3$ | $SCH_2CH_3$ | 3-Cl | $CH_3$ | $OCH_3$ | |
| $SCH_2CH_3$ | $SCH_2CH_2CH_3$ | H | $OCH_3$ | $OCH_3$ | |
| $SCH_2CH_2CH_3$ | $SCH_2CH_2CH_3$ | H | $CH_3$ | $OCH_3$ | |
| $S(O)CH_3$ | $SCH_3$ | H | $CH_3$ | $CH_3$ | |
| $S(O)_2CH_3$ | $SCH_3$ | H | $CH_3$ | $OCH_3$ | |
| $S(O)CH_3$ | $S(O)CH_3$ | H | $OCH_3$ | $OCH_3$ | |
| $S(O)_2CH_3$ | $S(O)CH_3$ | H | $CH_3$ | $OCH_3$ | |
| $SCH_3$ | $N(CH_3)_2$ | H | $CH_3$ | $OCH_3$ | |
| $S(O)CH_3$ | $N(CH_3)_2$ | H | $OCH_3$ | $OCH_3$ | |
| $S(O)_2CH_3$ | $N(CH_3)_2$ | H | $CH_3$ | $OCH_3$ | |
| $SCH_3$ | $N(CH_3)CH_2CH_3$ | 3-F | $CH_3$ | $OCH_3$ | |
| $SCH_3$ | $N(CH_2CH_3)_2$ | H | $OCH_3$ | $OCH_3$ | |
| $CF_3$ | $CF_3$ | H | $CH_3$ | $OCH_3$ | |
| $CF_3$ | $CF_3$ | 4-Br | $CH_3$ | $CH_3$ | |
| $N(CH_3)_2$ | $N(CH_3)_2$ | H | $CH_3$ | $OCH_3$ | |
| $N(CH_3)CH_2CH_3$ | $N(CH_3)_2$ | H | $OCH_3$ | $OCH_3$ | |
| $N(CH_2CH_3)_2$ | $N(CH_3)_2$ | 4-$CH_3$ | $CH_3$ | $OCH_3$ | |
| $N(CH_3)CH_2CH_3$ | $N(CH_3)CH_2CH_3$ | H | $OCH_3$ | $OCH_3$ | |
| $N(CH_2CH_3)_2$ | $N(CH_2CH_3)_2$ | H | $CH_3$ | $OCH_3$ | |
| $N(CH_3)_2$ | $C_6H_5$ | H | $CH_3$ | $OCH_3$ | |
| $N(CH_3)_2$ | 2'-$C_6H_4Cl$ | H | $CH_3$ | $OCH_3$ | |
| $N(CH_3)_2$ | $CH_2CO_2CH_3$ | H | $CH_3$ | $CH_3$ | |
| $N(CH_3)_2$ | $CH_2CO_2CH_2CH_3$ | H | $CH_3$ | $OCH_3$ | |
| $N(CH_3)_2$ | $CH_2CO_2CH_2CH_2CH_3$ | H | $OCH_3$ | $OCH_3$ | |
| $N(CH_3)_2$ | $CH_2CO_2CH_2CH=CH_2$ | H | $OCH_3$ | $OCH_3$ | |
| $N(CH_3)_2$ | $CH_2CO_2CH_2CH_2Cl$ | 5-$OCH_3$ | $CH_3$ | $CH_3$ | |
| $N(CH_3)_2$ | $CH_2CO_2CH_2CH_2OCH_3$ | H | $CH_3$ | $CH_3$ | |
| $N(CH_3)_2$ | $CHCO_2CH_3$<br>    \|<br>    $CH_3$ | H | $CH_3$ | $OCH_3$ | |
| $N(CH_3)_2$ | $CHCO_2CH_2CH=CH_2$<br>    \|<br>    $CH_3$ | H | $OCH_3$ | $OCH_3$ | |
| $N(CH_3)_2$ | $OSO_2CH_3$ | H | $CH_3$ | $OCH_3$ | |
| $N(CH_3)_2$ | $OSO_2CH_2CH_3$ | 3-$CF_3$ | $CH_3$ | $OCH_3$ | |
| $N(CH_3)_2$ | $OSO_2CH_2CH_2CH_3$ | H | $CH_3$ | $OCH_3$ | |
| $N(CH_3)_2$ | $OSO_2CF_3$ | H | $OCH_3$ | $OCH_3$ | |
| $N(CH_3)_2$ | $CH_2OCH_3$ | H | $CH_3$ | $OCH_3$ | |
| $N(CH_3)_2$ | $CH_2OCH_2CH_3$ | H | $CH_3$ | $CH_3$ | |
| $N(CH_3)_2$ | $CH_2OCH_2CH_2CH_3$ | H | $OCH_3$ | $OCH_3$ | |
| $N(CH_3)_2$ | $CH_2OCF_2H$ | H | $CH_3$ | $OCH_3$ | |
| $CO_2CH_3$ | $SO_2N(CH_3)_2$ | H | $CH_3$ | $OCH_3$ | |
| $CO_2CH_3$ | $SO_2N(CH_3)OCH_3$ | H | $CH_3$ | $CH_3$ | |
| $CO_2CH_2CH_2Cl$ | $SO_2N(CH_3)_2$ | H | $OCH_3$ | $OCH_3$ | |
| $CO_2CH_3$ | $C_6H_5$ | H | $CH_3$ | $OCH_3$ | |
| $CO_2CH_3$ | 2'-$C_6H_4OCH_3$ | H | $OCH_3$ | $OCH_3$ | |
| $CO_2CH_2CH_2CH_3$ | 3'-$C_6H_4CH_3$ | H | $CH_3$ | $CH_3$ | |
| $CO_2CH_3$ | $CH_2CO_2CH_3$ | H | $CH_3$ | $OCH_3$ | |
| $CO_2CH_2CH_2Cl$ | $CHCO_2CH_3$<br>    \|<br>    $CH_3$ | H | $OCH_3$ | $OCH_3$ | |
| $CO_2CH_3$ | $CH_2OCH_3$ | H | $CH_3$ | $OCH_3$ | |
| $CO_2CH_3$ | $CH_2OCF_2H$ | H | $OCH_3$ | $OCH_3$ | |
| $SO_2N(CH_3)_2$ | $SO_2N(CH_3)_2$ | H | $CH_3$ | $CH_3$ | |
| $SO_2N(CH_3)OCH_3$ | $SO_2N(CH_3)_3$ | H | $CH_3$ | $OCH_3$ | |
| $SO_2N(CH_3)OCH_3$ | $SO_2N(CH_3)OCH_3$ | H | $CH_3$ | $CH_3$ | |
| $SO_2N(CH_3)_2$ | $C_6H_5$ | H | $OCH_3$ | $OCH_3$ | |
| $SO_2N(CH_3)_2$ | 4'-$C_6H_4Cl$ | H | $CH_3$ | $OCH_3$ | |
| $SO_2N(CH_3)_2$ | 2'-$C_6H_4OCH_3$ | H | $OCH_3$ | $OCH_3$ | |
| $SO_2N(CH_3)_2$ | $CH_2CO_2CH_3$ | H | $CH_3$ | $OCH_3$ | |
| $SO_2N(CH_3)_2$ | $CHCO_2CH_3$<br>    \|<br>    $CH_3$ | H | $CH_3$ | $CH_3$ | |

TABLE 2b-continued

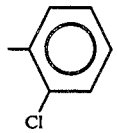

| R₁ | R₂ | R₃ | X | Y | m.p. (°C.) |
|---|---|---|---|---|---|
| SO₂N(CH₃)₂ | OSO₂CH₃ | H | CH₃ | OCH₃ | |
| SO₂N(CH₃)₂ | OSO₂CF₃ | H | OCH₃ | OCH₃ | |
| C₆H₅ | C₆H₅ | H | CH₃ | OCH₃ | |
| C₆H₅ | 2'-C₆H₄Cl | H | OCH₃ | OCH₃ | |
| C₆H₅ | 3'-C₆H₄Cl | H | CH₃ | OCH₃ | |
| 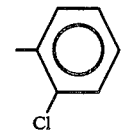 | 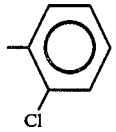 | H | OCH₃ | OCH₃ | |
| 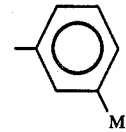 |  | H | CH₃ | CH₃ | |
| C₆H₅ | CH₂CO₂CH₃ | H | CH₃ | OCH₃ | |
| C₆H₅ | —CHCO₂CH₃<br>\|<br>CH₃ | H | OCH₃ | OCH₃ | |
| 2'-C₆H₄CH₃ | CH₂CO₂CH₃ | H | CH₃ | OCH₃ | |
| C₆H₅ | OSO₂CH₃ | H | CH₃ | OCH₃ | |
| C₆H₅ | OSO₂CF₃ | H | CH₃ | OCH₃ | |
| 2'-C₆H₄F | OSO₂CH₂CH₃ | H | OCH₃ | OCH₃ | |
| C₆H₅ | CH₂OCH₃ | H | CH₃ | OCH₃ | |
| 4'-C₆H₄Cl | CH₂OCF₂H | H | CH₃ | OCH₃ | |
| CH₂CO₂CH₃ | CH₂CO₂CH₃ | 3-CH₃ | CH₃ | OCH₃ | |
| CH₂CO₂CH₃ | CH₂CO₂CH₂CH₂Cl | H | CH₃ | OCH₃ | |
| CH₂CO₂CH₂CH₂OCH₃ | CH₂CO₂CH₂CH=CH₂ | H | CH₃ | OCH₃ | |
| CHCO₂CH₃<br>\|<br>CH₃ | CH₂CO₂CH₃ | H | OCH₃ | OCH₃ | |
| CHCO₂CH₂CH₂Cl<br>\|<br>CH₃ | CH₂CO₂CH₃ | H | CH₃ | CH₃ | |
| CHCO₂CH₃<br>\|<br>CH₃ | CHCO₂CH₃<br>\|<br>CH₃ | H | OCH₃ | CH₃ | |
| CH₂CO₂CH₃ | OSO₂CH₃ | H | OCH₃ | OCH₃ | |
| CHCO₂CH₃<br>\|<br>CH₃ | OSO₂CF₃ | H | CH₃ | OCH₃ | |
| CH₂CO₂CH₃ | CH₂OCH₃ | H | CH₃ | OCH₃ | |
| CHCO₂CH₃<br>\|<br>CH₃ | CH₂OCF₂H | H | CH₃ | CH₃ | |
| OSO₂CH₃ | OSO₂CH₃ | H | CH₃ | OCH₃ | |
| OSO₂CF₃ | OSO₂CH₃ | H | CH₃ | CH₃ | |
| OSO₂CF₃ | OSO₂CF₃ | H | CH₃ | CH₃ | |
| OSO₂CH₃ | CH₂OCH₃ | 4-CF₃ | CH₃ | OCH₃ | |
| OSO₂CF₃ | CH₂OCH₃ | H | OCH₃ | OCH₃ | |
| OSO₂CH₃ | CH₂OCF₂H | H | CH₃ | OCH₃ | |
| OSO₂CF₃ | CH₂OCF₂H | 5-Cl | CH₃ | CH₃ | |
| CH₂OCH₃ | CH₂OCH₃ | H | CH₃ | OCH₃ | |

TABLE 2b-continued

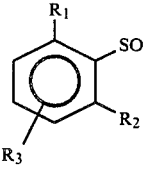

| R₁ | R₂ | R₃ | X | Y | m.p. (°C.) |
|---|---|---|---|---|---|
| CH₂OCF₂H | CH₂OCH₃ | H | OCH₃ | OCH₃ | |
| CH₂OCF₂H | CH₂OCF₂H | H | CH₃ | CH₃ | |
| SO₂CH₃ | C₆H₅ | H | CH₃ | CH₃ | |
| SO₂CH₃ | C₆H₅ | H | CH₃ | OCH₃ | 204–208°d |
| SO₂CH₃ | C₆H₅ | H | CH | CF₃ | |
| SO₂CH₃ | C₆H₅ | H | CH₃ | CH₂OCH₃ | |
| SO₂CH₃ | C₆H₅ | 3-Cl | CH₃ | CH₂OCH₃ | |
| SO₂CH₃ | C₆H₅ | H | CH₃ | OCH₂CF₃ | |
| SCH₃ | SCH₃ | H | CH₃ | CH₃ | 179–193° |
| SCH₃ | SCH₃ | H | CH₃ | OCH₃ | |
| SCH₃ | SCH₃ | H | CH₃ | CF₃ | |
| SCH₃ | SCH₃ | H | CH₃ | H | |
| SCH₃ | SCH₃ | H | CH₃ | NH₂ | |
| SCH₃ | SCH₃ | H | CH₃ | NHCH₃ | |
| SCH₃ | SCH₃ | H | CH₃ | N(CH₃)₂ | |
| SCH₃ | SCH₃ | H | CH₃ | CH₂CH₃ | |
| SCH₃ | SCH₃ | H | CH₃ | CH₂OCH₂CH₃ | |
| SCH₃ | SCH₃ | H | CH₃ | CH₂OCH₃ | |
| SCH₃ | SCH₃ | 5-CF₃ | CH₃ | OCH₂CH₃ | |
| SCH₃ | SCH₃ | H | CH₃ | SCH₃ | |
| SCH₃ | SCH₃ | H | CH₃ | OCH₂CH=CH₂ | |
| SCH₃ | SCH₃ | H | CH₃ | OCH₂C≡CH | |
| SCH₃ | SCH₃ | H | CH₃ | OCH₂CH₂F | |
| SCH₃ | C₆H₅ | H | CH₃ | OCH₂CH₂Cl | |
| SCH₃ | SCH₃ | H | CH₃ | OCH₂CH₂Br | |
| SCH₃ | SCH₃ | 3-Cl | CH₃ | OCH₃ | |
| SCH₃ | SCH₃ | 3-CH₃ | CH₃ | OCH₃ | |
| SO₂CH₃ | 2'-C₆H₄Cl | H | CH₃ | OCH₃ | |
| SO₂CH₃ | C₆H₅ | 3-Cl | CH₃ | OCH₃ | |
| SO₂CH₃ | C₆H₅ | 5-Cl | CH₃ | OCH₃ | |
| SO₂CH₃ | C₆H₅ | H | OCH₃ | CF₃ | |
| SO₂CH₃ | C₆H₅ | H | OCH₃ | CH₂OCH₃ | |
| SO₂CH₃ | C₆H₅ | H | OCH₃ | OCH₃ | 216–220°d |
| SO₂CH₃ | C₆H₅ | H | OCH₃ | OCH₂CF₃ | |
| SCH₃ | SCH₃ | H | OCH₃ | CF₃ | |
| SCH₃ | SCH₃ | H | OCH₃ | OCH₃ | 121–132° |
| SCH₃ | SCH₃ | H | OCH₃ | CH₂OCH₃ | |
| SCH₃ | SCH₃ | 3-Cl | CH₃ | OCH₃ | |
| SCH₃ | SCH₃ | 3-OCH₃ | OCH₃ | OCH₃ | |
| SCH₃ | SCH₃ | H | OCH₃ | N(CH₃)₂ | |
| SCH₃ | SCH₃ | H | OCH₃ | CH₂CH₃ | |
| SCH₃ | SCH₃ | H | OCH₃ | SCH₃ | |
| SCH₃ | SCH₃ | 3-Cl | CH₃ | OCH₃ | |
| SCH₃ | SCH₃ | 3-CH₃ | OCH₃ | OCH₃ | |
| SO₂CH₃ | C₆H₅ | H | OCH₂CH₃ | H | |
| SO₂CH₃ | C₆H₅ | H | OCH₂CH₃ | CH₃ | |
| SO₂CH₃ | C₆H₅ | H | OCH₂CH₃ | CF₃ | |
| SO₂CH₃ | C₆H₅ | H | OCH₂CH₃ | CH₂OCH₃ | |
| SCH₃ | SCH₃ | H | OCH₂CH₃ | CH₃ | |
| SCH₃ | SCH₃ | H | OCH₂CH₃ | CF₃ | |
| SCH₃ | SCH₃ | 3-OCH₃ | OCH₂CH₃ | CH₃ | |
| SCH₃ | C₆H₅ | H | OCH₃ | CH₃ | 130–135°d |

TABLE 3

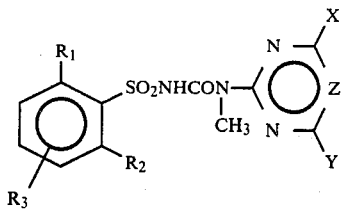

Z = (a.) N or (b.) CH

| R₁ | R₂ | R₃ | X | Y |
|---|---|---|---|---|
| SCH₃ | SCH₂CH₃ | H | CH₃ | CH₃ |
| SCH₃ | SCH₂CH₃ | H | CH₃ | OCH₃ |
| SCH₃ | SCH₂CH₃ | 5-CF₃ | CH₃ | OCH₃ |
| SCH₃ | SCH₂CH₃ | H | OCH₃ | OCH₃ |
| SCH₃ | SCH₂CH₃ | 3-Cl | OCH₃ | OCH₃ |
| SCH₃ | SCH₂CH₂CH₃ | H | CH₃ | OCH₃ |
| SCH₃ | SCH₂CH₂CH₃ | H | OCH₃ | OCH₃ |
| SCH₂CH₂CH₃ | SCH₂CH₂CH₃ | H | CH₃ | OCH₃ |
| SCH₂CH₂CH₃ | SCH₂CH₂CH₃ | H | OCH₃ | OCH₃ |
| SCH₂CH₂CH₃ | SCH₂CH₂CH₃ | 4-OCH₃ | CH₃ | OCH₃ |
| S(O)CH₃ | SCH₃ | H | CH₃ | OCH₃ |
| S(O)CH₃ | S(O)CH₃ | H | OCH₃ | OCH₃ |
| S(O)₂CH₃ | S(O)CH₃ | H | Cl[b] | OCH₃ |
| N(CH₃)₂ | C₆H₅ | H | CH₃ | CH₃ |
| N(CH₃)₂ | C₆H₅ | H | CH₃ | OCH₃ |
| N(CH₃)₂ | C₆H₅ | H | OCH₃ | OCH₃ |
| N(CH₃)₂ | C₆H₅ | H | Cl[b] | OCH₃ |
| N(CH₃)₂ | N(CH₃)₂ | H | CH₃ | OCH₃ |
| N(CH₃)₂ | N(CH₃)₂ | H | OCH₃ | OCH₃ |
| N(CH₃)₂ | N(CH₃)₂ | H | Cl[b] | OCH₃ |
| CF₃ | CF₃ | H | CH₃ | CH₃ |
| CF₃ | CF₃ | H | CH₃ | OCH₃ |
| CF₃ | CF₃ | H | OCH₃ | OCH₃ |
| CO₂CH₃ | C₆H₅ | H | CH₃ | OCH₃ |
| CO₂CH₃ | C₆H₅ | H | OCH₃ | OCH₃ |
| CO₂CH₃ | C₆H₅ | H | Cl[b] | OCH₃ |
| OSO₂N(CH₃)₂ | C₆H₅ | H | CH₃ | OCH₃ |
| OSO₂N(CH₃)₂ | C₆H₅ | H | OCH₃ | OCH₃ |
| C₆H₅ | C₆H₅ | H | CH₃ | CH₃ |
| C₆H₅ | C₆H₅ | H | CH₃ | OCH₃ |
| C₆H₅ | C₆H₅ | H | OCH₃ | OCH₃ |
| OSO₂CH₃ | C₆H₅ | H | CH₃ | OCH₃ |
| OSO₂CH₃ | C₆H₅ | H | OCH₃ | OCH₃ |
| OSO₂CH₃ | OSO₂CH₃ | H | CH₃ | CH₃ |
| OSO₂CH₃ | OSO₂CH₃ | H | CH₃ | OCH₃ |
| OSO₂CH₃ | OSO₂CH₃ | H | OCH₃ | OCH₃ |
| SCH₃ | N(CH₃)₂ | H | CH₃ | CH₃ |
| SCH₃ | N(CH₃)₂ | H | CH₃ | OCH₃ |
| SCH₃ | N(CH₃)₂ | H | OCH₃ | OCH₃ |
| S(O)CH₃ | N(CH₃)₂ | H | OCH₃ | OCH₃ |
| S(O)₂CH₃ | N(CH₃)₂ | H | OCH₃ | OCH₃ |

TABLE 4

Z = (a.) N or (b.) CH

| R₁ | R₃ | R₁₅ | R₁₆ | R₁₇ | X | Y |
|---|---|---|---|---|---|---|
| SCH₃ | H | H | H | H | CH₃ | OCH₃ |
| SCH₃ | H | H | H | H | OCH₃ | OCH₃ |
| SCH₃ | H | CH₃ | H | H | CH₃ | OCH₃ |
| SCH₃ | H | H | H | CH₃ | OCH₃ | OCH₃ |
| SCH₃ | H | CH₃ | CH₃ | CH₃ | CH₃ | CH₃ |
| SCH₂CH₃ | H | H | H | H | CH₃ | OCH₃ |
| SCH₂CH₂CH₃ | H | H | H | H | CH₃ | OCH₃ |
| S(O)CH₃ | H | H | H | H | CH₃ | CH₃ |
| S(O)CH₃ | H | H | H | H | CH₃ | OCH₃ |
| S(O)CH₃ | H | CH₃ | H | H | Cl | OCH₃[b] |
| S(O)CH₃ | H | H | H | CH₃ | CH₃ | OCH₃ |
| S(O)CH₃ | H | H | H | H | OCH₃ | OCH₃ |
| S(O)₂CH₃ | H | CH₃ | H | H | CH₃ | OCH₃ |
| S(O)₂CH₃ | H | H | H | CH₃ | OCH₃ | OCH₃ |
| CF₃ | H | H | H | H | CH₃ | CH₃ |
| CF₃ | H | CH₃ | H | H | OCH₃ | CH₃ |
| CF₃ | H | H | CH₃ | H | OCH₃ | OCH₃ |
| CF₃ | H | CH₃ | CH₃ | CH₃ | CH₃ | OCH₃ |
| N(CH₃)₂ | H | H | H | H | CH₃ | OCH₃ |
| N(CH₃)₂ | H | H | H | H | OCH₃ | OCH₃ |
| N(CH₃)₂ | H | CH₃ | H | H | CH₃ | OCH₃ |
| N(CH₃)₂ | H | H | CH₃ | H | OCH₃ | OCH₃ |
| N(CH₃)CH₂CH₃ | H | H | H | H | CH₃ | OCH₃ |
| N(CH₂CH₃)₂ | H | H | H | H | OCH₃ | OCH₃ |
| CO₂CH₃ | H | H | H | H | CH₃ | OCH₃ |
| CO₂CH₃ | H | CH₃ | H | H | OCH₃ | OCH₃ |
| CO₂CH₃ | H | H | CH₃ | CH₃ | CH₃ | CH₃ |
| CO₂CH₂CH₂Cl | H | H | H | H | CH₃ | OCH₃ |
| SO₂N(CH₃)₂ | H | H | H | H | OCH₃ | OCH₃ |
| SO₂N(CH₃)₂ | H | CH₃ | H | CH₃ | CH₃ | OCH₃ |
| C₆H₅ | H | H | H | H | CH₃ | OCH₃ |
| C₆H₅ | H | H | H | H | OCH₃ | OCH₃ |
| C₆H₅ | H | CH₃ | H | CH₃ | Cl | OCH₃[b] |
| C₆H₅ | H | H | CH₃ | H | CH₃ | OCH₃ |
| 2'-C₆H₄Cl | H | H | H | H | OCH₃ | OCH₃ |
| 2'-C₆H₄CH₃ | H | H | H | H | OCF₂H | OCH₃ |
| 2'-C₆H₄OCH₃ | H | H | H | H | CH₃ | OCH₃ |
| 3'-C₆H₄F | H | CH₃ | H | CH₃ | OCH₃ | OCH₃ |
| 4'-C₆H₄Br | H | CH₃ | CH₃ | CH₃ | Cl | OCH₃[b] |
| CH₂CO₂CH₃ | H | H | H | H | CH₃ | OCH₃ |
| CH₂CO₂CH₃ | H | CH₃ | H | H | OCH₃ | OCH₃ |
| CH₂CO₂CH₃ | H | H | CH₃ | H | Cl | OCH₃[b] |
| CHCO₂CH₃<br>\|<br>CH₃ | H | H | H | H | OCH₃ | OCF₂H |
| OSO₂CH₃ | H | H | H | H | CH₃ | OCH₃ |
| OSO₂CH₃ | H | CH₃ | H | H | OCH₃ | OCH₃ |
| OSO₂CH₃ | H | H | CH₃ | CH₃ | Cl | OCH₃[b] |
| OSO₂CH₃ | H | H | CH₃ | H | OCH₃ | OCF₂H |
| OSO₂CF₃ | H | H | H | H | CH₃ | OCH₃ |
| CH₂OCH₃ | H | H | H | H | CH₃ | OCH₃ |
| CH₂OCH₃ | H | CH₃ | H | H | OCH₃ | OCH₃ |
| CH₂OCH₃ | H | H | CH₃ | H | OCH₃ | OCF₂H |
| CH₂OCH₃ | H | CH₃ | CH₃ | CH₃ | CH₃ | CH₃ |
| CH₂OCF₂H | H | H | H | H | OCH₃ | OCH₃ |
| CH₂OCF₂H | H | CH₃ | H | CH₃ | OCH₃ | OCF₂H |
| CH₂OCF₂H | H | H | CH₃ | H | Cl | OCH₃[b] |
| CH₂OCF₂H | H | CH₃ | CH₃ | H | CH₃ | OCH₃ |

TABLE 5

(a.) Z = N
(b.) Z = CH

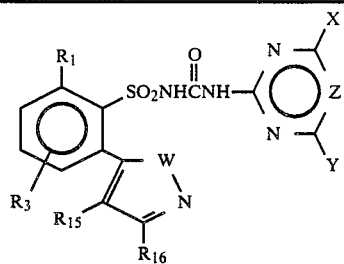

(c.) Z = N
(d.) Z = CH

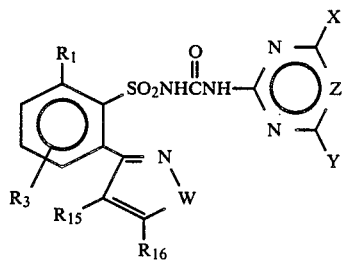

(e.) Z = N
(f.) Z = CH

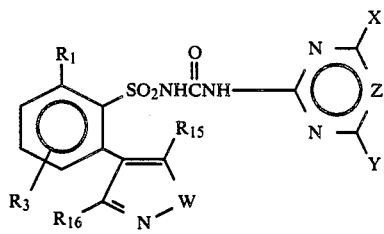

| R₁ | R₃ | W | R₁₅ | R₁₆ | X | Y |
|---|---|---|---|---|---|---|
| SCH₃ | H | O | H | H | CH₃ | OCH₃ |
| SCH₃ | H | O | H | H | OCH₃ | OCH₃ |
| SCH₃ | H | O | CH₃ | H | CH₃ | OCH₃ |
| SCH₃ | H | O | H | CH₃ | OCH₃ | OCH₃ |
| SCH₃ | H | O | CH₃ | CH₃ | CH₃ | CH₃ |
| SCH₃ | 3-CH₃ | O | CH₃ | CH₃ | CH₃ | OCH₃ |
| SCH₂CH₃ | H | O | H | H | CH₃ | OCH₃ |
| SCH₂CH₂CH₃ | H | O | H | H | CH₃ | OCH₃ |
| S(O)CH₃ | H | O | H | H | CH₃ | CH₃ |
| S(O)CH₃ | H | O | H | H | CH₃ | OCH₃ |
| S(O)CH₃ | H | O | CH₃ | H | Cl[b,d,f] | OCH₃ |
| S(O)CH₃ | H | O | H | CH₃ | CH₃ | OCH₃ |
| S(O)₂CH₃ | H | O | H | H | OCH₃ | OCH₃ |
| S(O)₂CH₃ | H | O | CH₃ | H | CH₃ | OCH₃ |
| S(O)₂CH₃ | H | O | H | CH₃ | OCH₃ | OCH₃ |
| CF₃ | H | O | H | H | CH₃ | CH₃ |
| CF₃ | H | O | CH₃ | H | OCH₃ | CH₃ |
| CF₃ | H | O | H | CH₃ | OCH₃ | OCH₃ |
| CF₃ | H | O | CH₃ | CH₃ | CH₃ | OCH₃ |
| N(CH₃)₂ | H | O | H | H | CH₃ | OCH₃ |
| N(CH₃)₂ | H | O | H | H | OCH₃ | OCH₃ |
| N(CH₃)₂ | H | O | CH₃ | H | CH₃ | OCH₃ |
| N(CH₃)₂ | H | O | H | CH₃ | OCH₃ | OCH₃ |
| N(CH₃)CH₂CH₃ | H | O | H | H | CH₃ | OCH₃ |
| N(CH₂CH₃)₂ | H | O | H | H | OCH₃ | OCH₃ |
| CO₂CH₃ | H | O | H | H | CH₃ | OCH₃ |
| CO₂CH₃ | H | O | CH₃ | H | OCH₃ | OCH₃ |
| CO₂CH₃ | H | O | H | CH₃ | CH₃ | CH₃ |
| CO₂CH₂CH₂Cl | H | O | H | H | CH₃ | OCH₃ |
| SO₂N(CH₃)₂ | H | O | H | H | OCH₃ | OCH₃ |
| SO₂N(CH₃)₂ | H | O | CH₃ | H | CH₃ | OCH₃ |
| C₆H₅ | H | O | H | H | CH₃ | CH₃ |
| C₆H₅ | H | O | H | H | CH₃ | OCH₃ |
| C₆H₅ | H | O | H | H | OCH₃ | OCH₃ |
| C₆H₅ | H | O | CH₃ | H | CH₃ | OCH₃ |
| C₆H₅ | H | O | H | CH₃ | OCH₃ | OCH₃ |
| C₆H₅ | H | O | CH₃ | CH₃ | OCH₃ | OCF₂H |
| 2'-C₆H₄Cl | H | O | H | H | CH₃ | OCH₃ |
| 2'-C₆H₄OCH₃ | H | O | H | H | OCH₃ | OCH₃ |
| 2'-C₆H₄CH₃ | H | O | H | H | Cl[b,d,f] | OCH₃ |
| 3'-C₆H₄Br | H | O | H | H | CH₃ | OCH₃ |
| 4'-C₆H₄F | H | O | H | H | OCH₃ | OCH₃ |

TABLE 5-continued

| | | | | | | |
|---|---|---|---|---|---|---|
| CH$_2$CO$_2$CH$_3$ | H | O | H | H | CH$_3$ | OCH$_3$ |
| CH$_2$CO$_2$CH$_3$ | H | O | CH$_3$ | H | OCH$_3$ | OCH$_3$ |
| CH$_2$CO$_2$CH$_3$ | H | O | H | CH$_3$ | Cl$^{b,d,f}$ | OCH$_3$ |
| CHCO$_2$CH$_3$<br>\|<br>CH$_3$ | H | O | H | H | OCH$_3$ | OCF$_2$H |
| OSO$_2$CH$_3$ | H | O | H | H | CH$_3$ | OCH$_3$ |
| OSO$_2$CH$_3$ | H | O | CH$_3$ | H | OCH$_3$ | OCH$_3$ |
| OSO$_2$CH$_3$ | H | O | H | CH$_3$ | Cl$^{b,d,f}$ | OCH$_3$ |
| OSO$_2$CH$_3$ | H | O | CH$_3$ | CH$_3$ | OCH$_3$ | OCF$_2$H |
| OSO$_2$CF$_3$ | H | O | H | H | CH$_3$ | OCH$_3$ |
| CH$_2$OCH$_3$ | H | O | H | H | CH$_3$ | OCH$_3$ |
| CH$_2$OCH$_3$ | H | O | CH$_3$ | H | OCH$_3$ | OCH$_3$ |
| CH$_2$OCH$_3$ | H | O | H | CH$_3$ | OCH$_3$ | OCF$_2$H |
| CH$_2$OCH$_3$ | H | O | CH$_3$ | CH$_3$ | CH$_3$ | CH$_3$ |
| CH$_2$OCF$_2$H | H | O | H | H | OCH$_3$ | OCH$_3$ |
| CH$_2$OCF$_2$H | H | O | CH$_3$ | H | OCH$_3$ | OCF$_2$H |
| CH$_2$OCF$_2$H | H | O | H | CH$_3$ | Cl$^{b,d,f}$ | OCH$_3$ |
| CH$_2$OCF$_2$H | H | O | CH$_3$ | CH$_3$ | CH$_3$ | OCH$_3$ |
| SCH$_3$ | H | NCH$_3$ | H | H | CH$_3$ | OCH$_3$ |
| SCH$_3$ | H | NCH$_3$ | H | H | OCH$_3$ | OCH$_3$ |
| SCH$_3$ | H | NCH$_3$ | CH$_3$ | H | CH$_3$ | OCH$_3$ |
| SCH$_3$ | H | NCH$_3$ | H | CH$_3$ | OCH$_3$ | OCH$_3$ |
| SCH$_3$ | H | NH | CH$_3$ | CH$_3$ | CH$_3$ | CH$_3$ |
| SCH$_3$ | 3-OCH$_3$ | NCH$_3$ | CH$_3$ | CH$_3$ | CH$_3$ | OCH$_3$ |
| SCH$_2$CH$_3$ | H | NCH$_3$ | H | H | CH$_3$ | OCH$_3$ |
| SCH$_2$CH$_2$CH$_3$ | H | NCH$_3$ | H | H | CH$_3$ | OCH$_3$ |
| S(O)CH$_3$ | H | NH | H | H | CH$_3$ | CH$_3$ |
| S(O)CH$_3$ | H | NCH$_3$ | H | H | CH$_3$ | OCH$_3$ |
| S(O)CH$_3$ | H | NCH$_3$ | CH$_3$ | H | Cl$^{b,d,f}$ | OCH$_3$ |
| S(O)CH$_3$ | H | NCH$_3$ | H | CH$_3$ | CH$_3$ | OCH$_3$ |
| S(O)$_2$CH$_3$ | H | NCH$_3$ | H | H | OCH$_3$ | OCH$_3$ |
| S(O)$_2$CH$_3$ | H | NCH$_3$ | CH$_3$ | H | CH$_3$ | OCH$_3$ |
| S(O)$_2$CH$_3$ | H | NCH$_3$ | H | CH$_3$ | OCH$_3$ | OCH$_3$ |
| CF$_3$ | H | NH | H | H | CH$_3$ | CH$_3$ |
| CF$_3$ | H | NCH$_3$ | CH$_3$ | H | OCH$_3$ | CH$_3$ |
| CF$_3$ | H | NCH$_3$ | H | CH$_3$ | OCH$_3$ | OCH$_3$ |
| CF$_3$ | H | NH | CH$_3$ | CH$_3$ | CH$_3$ | OCH$_3$ |
| N(CH$_3$)$_2$ | H | NCH$_3$ | H | H | CH$_3$ | OCH$_3$ |
| N(CH$_3$)$_2$ | H | NCH$_3$ | H | H | OCH$_3$ | OCH$_3$ |
| N(CH$_3$)$_2$ | H | NCH$_3$ | CH$_3$ | H | CH$_3$ | OCH$_3$ |
| N(CH$_3$)$_2$ | H | NCH$_3$ | H | H | OCH$_3$ | OCH$_3$ |
| N(CH$_3$)CH$_2$CH$_3$ | H | NCH$_3$ | H | H | CH$_3$ | OCH$_3$ |
| N(CH$_2$CH$_3$)$_2$ | H | NCH$_3$ | H | H | OCH$_3$ | OCH$_3$ |
| CO$_2$CH$_3$ | H | NCH$_3$ | H | H | CH$_3$ | OCH$_3$ |
| CO$_2$CH$_3$ | H | NCH$_3$ | CH$_3$ | H | OCH$_3$ | OCH$_3$ |
| CO$_2$CH$_3$ | H | NCH$_3$ | H | H | CH$_3$ | CH$_3$ |
| CO$_2$CH$_2$CH$_2$Cl | H | NCH$_3$ | H | H | CH$_3$ | OCH$_3$ |
| SO$_2$N(CH$_3$)$_2$ | H | NCH$_3$ | H | H | OCH$_3$ | OCH$_3$ |
| SO$_2$N(CH$_3$)$_2$ | H | NH | CH$_3$ | H | CH$_3$ | OCH$_3$ |
| C$_6$H$_5$ | H | NCH$_3$ | H | H | CH$_3$ | CH$_3$ |
| C$_6$H$_5$ | H | NCH$_3$ | H | H | CH$_3$ | OCH$_3$ |
| C$_6$H$_5$ | H | NCH$_3$ | H | H | OCH$_3$ | OCH$_3$ |
| C$_6$H$_5$ | H | NCH$_3$ | CH$_3$ | H | CH$_3$ | OCH$_3$ |
| C$_6$H$_5$ | H | NCH$_3$ | H | CH$_3$ | OCH$_3$ | OCH$_3$ |
| C$_6$H$_5$ | H | NCH$_3$ | CH$_3$ | CH$_3$ | OCH$_3$ | OCF$_2$H |
| 2'-C$_6$H$_4$Cl | H | NCH$_3$ | H | H | CH$_3$ | OCH$_3$ |
| 2'-C$_6$H$_4$OCH$_3$ | H | NCH$_3$ | H | H | OCH$_3$ | OCH$_3$ |
| 2'-C$_6$H$_4$CH$_3$ | H | NCH$_3$ | H | H | Cl$^{b,d,f}$ | OCH$_3$ |
| 3'-C$_6$H$_4$Br | H | NH | H | H | CH$_3$ | OCH$_3$ |
| 4'-C$_6$H$_4$F | H | NCH$_3$ | H | H | OCH$_3$ | OCH$_3$ |
| CH$_2$CO$_2$CH$_3$ | H | NCH$_3$ | H | H | CH$_3$ | OCH$_3$ |
| CH$_2$CO$_2$CH$_3$ | H | NCH$_3$ | CH$_3$ | H | OCH$_3$ | OCH$_3$ |
| CH$_2$CO$_2$CH$_3$ | H | NCH$_3$ | H | CH$_3$ | Cl$^{b,d,f}$ | OCH$_3$ |
| CHCO$_2$CH$_3$<br>\|<br>CH$_3$ | H | NCH$_3$ | H | H | OCH$_3$ | OCF$_2$H |
| OSO$_2$CH$_3$ | H | NCH$_3$ | H | H | CH$_3$ | OCH$_3$ |
| OSO$_2$CH$_3$ | H | NCH$_3$ | CH$_3$ | H | OCH$_3$ | OCH$_3$ |
| OSO$_2$CH$_3$ | H | NCH$_3$ | H | CH$_3$ | Cl$^{b,d,f}$ | OCH$_3$ |
| OSO$_2$CH$_3$ | H | NCH$_3$ | CH$_3$ | CH$_3$ | OCH$_3$ | OCF$_2$H |
| OSO$_2$CF$_3$ | H | NCH$_3$ | H | H | CH$_3$ | OCH$_3$ |
| CH$_2$OCH$_3$ | H | NCH$_3$ | H | H | CH$_3$ | OCH$_3$ |
| CH$_2$OCH$_3$ | H | NCH$_3$ | CH$_3$ | H | OCH$_3$ | OCH$_3$ |
| CH$_2$OCH$_3$ | H | NH | H | CH$_3$ | OCH$_3$ | OCF$_2$H |
| CH$_2$OCH$_3$ | H | NCH$_3$ | CH$_3$ | CH$_3$ | CH$_3$ | CH$_3$ |
| CH$_2$OCF$_2$H | H | NCH$_3$ | H | H | OCH$_3$ | OCH$_3$ |
| CH$_2$OCF$_2$H | H | NCH$_3$ | CH$_3$ | H | OCH$_3$ | OCF$_2$H |

TABLE 5-continued

| | | | | | | |
|---|---|---|---|---|---|---|
| CH2OCF2H | H | NCH3 | H | CH3 | OCF2H | OCH3 |
| CH2OCF2H | H | NCH3 | CH3 | CH3 | CH3 | OCH3 |
| SCH3 | H | S | H | H | CH3 | OCH3 |
| SCH3 | H | S | H | H | OCH3 | OCH3 |
| SCH3 | H | S | CH3 | H | CH3 | OCH3 |
| SCH3 | H | S | H | CH3 | OCH3 | OCH3 |
| SCH3 | H | S | CH3 | CH3 | CH3 | CH3 |
| SCH3 | 3-Cl | S | CH3 | CH3 | CH3 | OCH3 |
| SCH2CH3 | H | S | H | H | CH3 | OCH3 |
| SCH2CH2CH3 | H | S | H | H | CH3 | OCH3 |
| S(O)CH3 | H | S | H | H | CH3 | CH3 |
| S(O)CH3 | H | S | H | H | CH3 | OCH3 |
| S(O)CH3 | H | S | CH3 | H | Cl[b,d,f] | OCH3 |
| S(O)CH3 | H | S | H | CH3 | CH3 | OCH3 |
| S(O)CH3 | H | S | H | H | OCH3 | OCH3 |
| S(O)CH3 | H | S | CH3 | H | CH3 | OCH3 |
| S(O)CH3 | H | S | H | CH3 | OCH3 | OCH3 |
| CF3 | H | S | H | H | CH3 | CH3 |
| CF3 | H | S | CH3 | H | OCH3 | CH3 |
| CF3 | H | O | H | CH3 | OCH3 | OCH3 |
| CF3 | H | S | CH3 | CH3 | CH3 | OCH3 |
| N(CH3)2 | H | S | H | H | CH3 | OCH3 |
| N(CH3)2 | H | S | H | H | OCH3 | OCH3 |
| N(CH3)2 | H | S | CH3 | H | CH3 | OCH3 |
| N(CH3)2 | H | S | H | CH3 | OCH3 | OCH3 |
| N(CH3)CH2CH3 | H | S | H | H | CH3 | OCH3 |
| N(CH2CH3)2 | H | S | H | H | OCH3 | OCH3 |
| CO2CH3 | H | S | H | H | CH3 | OCH3 |
| CO2CH3 | H | S | CH3 | H | OCH3 | OCH3 |
| CO2CH3 | H | S | H | CH3 | CH3 | CH3 |
| CO2CH2CH2Cl | H | S | H | H | CH3 | OCH3 |
| SO2N(CH3)2 | H | S | H | H | OCH3 | OCH3 |
| SO2N(CH3)2 | H | S | CH3 | H | CH3 | OCH3 |
| C6H5 | H | S | H | H | CH3 | CH3 |
| C6H5 | H | S | H | H | CH3 | OCH3 |
| C6H5 | H | S | H | H | OCH3 | OCH3 |
| C6H5 | H | S | CH3 | H | CH3 | OCH3 |
| C6H5 | H | S | H | CH3 | OCH3 | OCH3 |
| C6H5 | H | S | CH3 | CH3 | OCH3 | OCF2H |
| 2'-C6H4Cl | H | S | H | H | CH3 | OCH3 |
| 2'-C6H4OCH3 | H | S | H | H | OCH3 | OCH3 |
| 2'-C6H4CH3 | H | S | H | H | Cl[b,d,f] | OCH3 |
| 3'-C6H4Br | H | S | H | H | CH3 | OCH3 |
| 4'-C6H4F | H | S | H | H | OCH3 | OCH3 |
| CH2CO2CH3 | H | S | H | H | CH3 | OCH3 |
| CH2CO2CH3 | H | S | CH3 | H | OCH3 | OCH3 |
| CH2CO2CH3 | H | S | H | CH3 | OCF2H | OCH3 |
| CHCO2CH3<br>\|<br>CH3 | H | S | H | H | OCH3 | OCF2H |
| OSO2CH3 | H | S | H | H | CH3 | OCH3 |
| OSO2CH3 | H | S | CH3 | H | OCH3 | OCH3 |
| OSO2CH3 | H | S | H | CH3 | Cl[b,d,f] | OCH3 |
| OSO2CH3 | H | S | CH3 | CH3 | OCH3 | OCF2H |
| OSO2CF3 | H | S | H | H | CH3 | OCH3 |
| CH2OCH3 | H | S | H | H | CH3 | OCH3 |
| CH2OCH3 | H | S | CH3 | H | OCH3 | OCH3 |
| CH2OCH3 | H | S | H | CH3 | OCH3 | OCF2H |
| CH2OCH3 | H | S | CH3 | CH3 | CH3 | CH3 |
| CH2OCF2H | H | S | H | H | OCH3 | OCH3 |
| CH2OCF2H | H | S | CH3 | H | OCH3 | OCF2H |
| CH2OCF2H | H | S | H | CH3 | Cl[b,d,f] | OCH3 |
| CH2OCF2H | H | S | CH3 | CH3 | CH3 | OCH3 |

TABLE 6

(a.) Z = N
(b.) Z = CH

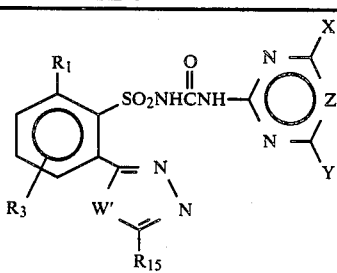

TABLE 6-continued (c.) Z = N
(d.) Z = CH

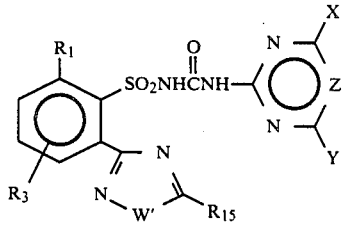

TABLE 6-continued (e.) Z = N
(f.) Z = CH

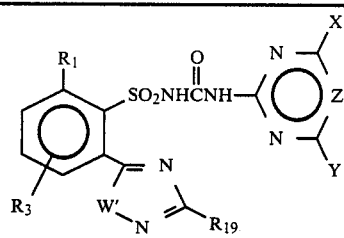

| R₁ | R₃ | W' | R₁₅ | X | Y |
|---|---|---|---|---|---|
| SCH₃ | H | O | H | CH₃ | OCH₃ |
| SCH₃ | H | O | H | OCH₃ | OCH₃ |
| SCH₃ | H | O | CH₃ | CH₃ | OCH₃ |
| SCH₃ | H | O | CH₃ | CH₃ | CH₃ |
| SCH₂CH₃ | H | O | H | CH₃ | OCH₃ |
| SCH₂CH₂CH₃ | H | O | H | CH₃ | OCH₃ |
| S(O)CH₃ | H | O | H | CH₃ | CH₃ |
| S(O)CH₃ | H | O | H | CH₃ | OCH₃ |
| S(O)CH₃ | H | O | CH₃ | Cl | OCH₃[b,d,f] |
| S(O)₂CH₃ | H | O | H | OCH₃ | OCH₃ |
| S(O)₂CH₃ | H | O | CH₃ | CH₃ | OCH₃ |
| S(O)₂CH₃ | H | O | CH₃ | OCH₃ | OCH₃ |
| CF₃ | H | O | H | CH₃ | CH₃ |
| CF₃ | H | O | H | OCH₃ | OCH₃ |
| CF₃ | H | O | CH₃ | CH₃ | OCH₃ |
| N(CH₃)₂ | H | O | H | CH₃ | OCH₃ |
| N(CH₃)₂ | H | O | H | OCH₃ | OCH₃ |
| N(CH₃)₂ | H | O | CH₃ | CH₃ | OCH₃ |
| N(CH₃)CH₂CH₃ | H | O | H | CH₃ | OCH₃ |
| N(CH₂CH₃)₂ | H | O | H | OCH₃ | OCH₃ |
| CO₂CH₃ | H | O | H | CH₃ | OCH₃ |
| CO₂CH₃ | H | O | H | OCH₃ | OCH₃ |
| CO₂CH₃ | H | O | CH₃ | CH₃ | CH₃ |
| CO₂CH₂CH₂Cl | H | O | H | CH₃ | OCH₃ |
| SO₂N(CH₃)₂ | H | O | H | OCH₃ | OCH₃ |
| SO₂N(CH₃)₂ | H | O | CH₃ | CH₃ | OCH₃ |
| C₆H₅ | H | O | H | CH₃ | CH₃ |
| C₆H₅ | H | O | H | CH₃ | OCH₃ |
| C₆H₅ | H | O | H | OCH₃ | OCH₃ |
| C₆H₅ | H | O | CH₃ | OCH₃ | OCH₃ |
| 2'-C₆H₄Cl | H | O | H | CH₃ | OCH₃ |
| 2'-C₆H₄CH₃ | H | O | H | OCH₃ | OCH₃ |
| 2'-C₆H₄OCH₃ | H | O | H | OCF₂H | OCH₃ |
| 3'-C₆H₄Br | H | O | H | CH₃ | OCH₃ |
| 4'-C₆H₄F | H | O | H | Cl | OCH₃[b,d,f] |
| CH₂CO₂CH₃ | H | O | H | CH₃ | OCH₃ |
| CH₂CO₂CH₃ | H | O | H | OCH₃ | OCH₃ |
| CH₂CO₂CH₃ | H | O | CH₃ | Cl | OCH₃[b,d,f] |
| CHCO₂CH₃<br>\|<br>CH₃ | H | O | H | OCH₃ | OCF₂H |
| OSO₂CH₃ | H | O | H | CH₃ | OCH₃ |
| OSO₂CH₃ | H | O | H | OCH₃ | OCH₃ |
| OSO₂CH₃ | H | O | CH₃ | Cl | OCH₃[b,d,f] |
| OSO₂CH₃ | H | O | CH₃ | OCH₃ | OCF₂H |
| OSO₂CF₃ | H | O | H | CH₃ | OCH₃ |
| CH₂OCH₃ | H | O | H | CH₃ | OCH₃ |
| CH₂OCH₃ | H | O | H | OCH₃ | OCH₃ |
| CH₂OCH₃ | H | O | CH₃ | OCH₃ | OCF₂H |
| CH₂OCH₃ | H | O | CH₃ | CH₃ | CH₃ |
| CH₂OCF₂H | H | O | H | OCH₃ | OCH₃ |
| CH₂OCF₂H | H | O | H | OCH₃ | OCF₂H |
| CH₂OCF₂H | H | O | CH₃ | Cl | OCH₃[b,d,f] |
| CH₂OCF₂H | H | O | CH₃ | CH₃ | OCH₃ |
| SCH₃ | H | S | H | CH₃ | OCH₃ |
| SCH₃ | H | S | H | OCH₃ | OCH₃ |
| SCH₃ | H | S | CH₃ | CH₃ | OCH₃ |
| SCH₃ | H | S | CH₃ | CH₃ | CH₃ |
| SCH₂CH₃ | H | S | H | CH₃ | OCH₃ |
| SCH₂CH₂CH₃ | H | S | H | CH₃ | OCH₃ |
| S(O)CH₃ | H | S | H | CH₃ | CH₃ |
| S(O)CH₃ | H | S | H | CH₃ | OCH₃ |
| S(O)CH₃ | H | S | CH₃ | Cl | OCH₃[b,d,f] |
| S(O)₂CH₃ | H | S | H | OCH₃ | OCH₃ |
| S(O)₂CH₃ | H | S | CH₃ | CH₃ | OCH₃ |
| S(O)₂CH₃ | H | S | CH₃ | CH₃ | CH₃ |
| CF₃ | H | S | H | CH₃ | CH₃ |
| CF₃ | H | O | H | OCH₃ | OCH₃ |
| CF₃ | H | S | CH₃ | CH₃ | OCH₃ |
| N(CH₃)₂ | H | S | H | CH₃ | OCH₃ |
| N(CH₃)₂ | H | S | H | OCH₃ | OCH₃ |
| N(CH₃)₂ | H | S | CH₃ | CH₃ | OCH₃ |
| N(CH₃)CH₂CH₃ | H | S | H | CH₃ | OCH₃ |
| N(CH₂CH₃)₂ | H | S | H | OCH₃ | OCH₃ |
| CO₂CH₃ | H | S | H | CH₃ | OCH₃ |
| CO₂CH₃ | H | S | H | OCH₃ | OCH₃ |
| CO₂CH₃ | H | S | CH₃ | CH₃ | CH₃ |
| CO₂CH₂CH₂Cl | H | S | H | CH₃ | OCH₃ |
| SO₂N(CH₃)₂ | H | S | H | OCH₃ | OCH₃ |
| SO₂N(CH₃)₂ | H | S | CH₃ | CH₃ | CH₃ |
| C₆H₅ | H | S | H | CH₃ | CH₃ |
| C₆H₅ | H | S | H | CH₃ | OCH₃ |
| C₆H₅ | H | S | H | OCH₃ | OCH₃ |
| C₆H₅ | H | S | CH₃ | OCH₃ | OCH₃ |
| 2'-C₆H₄Cl | H | S | H | CH₃ | OCH₃ |
| 2'-C₆H₄CH₃ | H | S | H | OCH₃ | OCH₃ |
| 2'-C₆H₄OCH₃ | H | S | H | OCF₂H | OCH₃ |
| 3'-C₆H₄Br | H | S | H | CH₃ | OCH₃ |
| 4'-C₆H₄F | H | S | H | Cl | OCH₃[b,d,f] |
| CH₂CO₂CH₃ | H | S | H | CH₃ | OCH₃ |
| CH₂CO₂CH₃ | H | S | H | OCH₃ | OCH₃ |
| CH₂CO₂CH₃ | H | S | CH₃ | Cl | OCH₃[b,d,f] |
| CHCO₂CH₃<br>\|<br>CH₃ | H | S | H | OCH₃ | OCF₂H |
| OSO₂CH₃ | H | S | H | CH₃ | OCH₃ |
| OSO₂CH₃ | H | S | H | OCH₃ | OCH₃ |
| OSO₂CH₃ | H | S | CH₃ | Cl | OCH₃[b,d,f] |
| OSO₂CH₃ | H | S | CH₃ | OCH₃ | OCF₂H |
| OSO₂CF₃ | H | S | H | CH₃ | OCH₃ |
| CH₂OCH₃ | H | S | H | CH₃ | OCH₃ |
| CH₂OCH₃ | H | S | H | OCH₃ | OCH₃ |
| CH₂OCH₃ | H | S | CH₃ | OCH₃ | OCF₂H |
| CH₂OCH₃ | H | S | CH₃ | CH₃ | CH₃ |
| CH₂OCF₂H | H | S | H | OCH₃ | OCH₃ |
| CH₂OCF₂H | H | S | H | OCH₃ | OCF₂H |
| CH₂OCF₂H | H | S | CH₃ | Cl | OCH₃[b,d,f] |
| CH₂OCF₂H | H | S | CH₃ | CH₃ | OCH₃ |

TABLE 7

(a.) Z = N
(b.) Z = CH

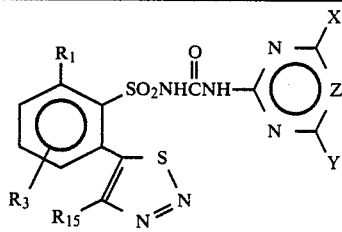

(c.) Z = N
(d.) Z = CH

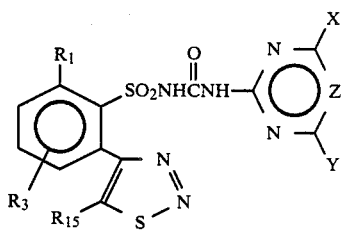

| R₁ | R₃ | R₁₅ | X | Y |
|---|---|---|---|---|
| SCH₃ | H | H | CH₃ | OCH₃ |
| SCH₃ | H | H | OCH₃ | OCH₃ |
| SCH₃ | H | CH₃ | OCH₃ | OCH₃ |
| SCH₃ | H | CH₃ | CH₃ | CH₃ |
| SCH₂CH₃ | H | H | CH₃ | OCH₃ |
| SCH₂CH₂CH₃ | H | H | CH₃ | OCH₃ |
| S(O)CH₃ | H | H | CH₃ | CH₃ |
| S(O)CH₃ | H | H | CH₃ | OCH₃ |
| S(O)CH₃ | H | CH₃ | Cl | OCH₃[b,d] |
| S(O)₂CH₃ | H | H | OCH₃ | OCH₃ |
| S(O)₂CH₃ | H | H | CH₃ | OCH₃ |

TABLE 7-continued

| | | | | |
|---|---|---|---|---|
| S(O)$_2$CH$_3$ | H | CH$_3$ | OCH$_3$ | OCH$_3$ |
| CF$_3$ | H | H | CH$_3$ | CH$_3$ |
| CF$_3$ | H | H | OCH$_3$ | OCH$_3$ |
| CF$_3$ | H | CH$_3$ | CH$_3$ | OCH$_3$ |
| N(CH$_3$)$_2$ | H | H | CH$_3$ | OCH$_3$ |
| N(CH$_3$)$_2$ | H | H | OCH$_3$ | OCH$_3$ |
| N(CH$_3$)$_2$ | H | CH$_3$ | CH$_3$ | OCH$_3$ |
| N(CH$_3$)CH$_2$CH$_3$ | H | H | CH$_3$ | OCH$_3$ |
| N(CH$_2$CH$_3$)$_2$ | H | H | OCH$_3$ | OCH$_3$ |
| CO$_2$CH$_3$ | H | H | CH$_3$ | OCH$_3$ |
| CO$_2$CH$_3$ | H | H | OCH$_3$ | OCH$_3$ |
| CO$_2$CH$_3$ | H | CH$_3$ | CH$_3$ | CH$_3$ |
| CO$_2$CH$_2$CH$_2$Cl | H | H | CH$_3$ | OCH$_3$ |
| SO$_2$N(CH$_3$)$_2$ | H | H | OCH$_3$ | OCH$_3$ |
| SO$_2$N(CH$_3$)$_2$ | H | CH$_3$ | CH$_3$ | OCH$_3$ |
| C$_6$H$_5$ | H | H | CH$_3$ | CH$_3$ |
| C$_6$H$_5$ | H | H | CH$_3$ | OCH$_3$ |
| C$_6$H$_5$ | H | H | OCH$_3$ | OCH$_3$ |
| C$_6$H$_5$ | H | CH$_3$ | OCH$_3$ | OCH$_3$ |
| 2'-C$_6$H$_4$Cl | H | H | CH$_3$ | OCH$_3$ |
| 2'-C$_6$H$_4$CH$_3$ | H | H | OCH$_3$ | OCH$_3$ |
| 2'-C$_6$H$_4$OCH$_3$ | H | H | OCF$_2$H | OCH$_3$ |
| 3'-C$_6$H$_4$Br | H | H | CH$_3$ | OCH$_3$ |
| 4'-C$_6$H$_4$F | H | H | Cl | OCH$_3$ [b,d] |
| CH$_2$CO$_2$CH$_3$ | H | H | CH$_3$ | OCH$_3$ |
| CH$_2$CO$_2$CH$_3$ | H | H | OCH$_3$ | OCH$_3$ |
| CH$_2$CO$_2$CH$_3$ | H | CH$_3$ | Cl | OCH$_3$ [b,d] |
| CHCO$_2$CH$_3$<br>\|<br>CH$_3$ | H | H | OCH$_3$ | OCF$_2$H |
| OSO$_2$CH$_3$ | H | H | CH$_3$ | OCH$_3$ |
| OSO$_2$CH$_3$ | H | H | OCH$_3$ | OCH$_3$ |
| OSO$_2$CH$_3$ | H | CH$_3$ | Cl | OCH$_3$ [b,d] |
| OSO$_2$CH$_3$ | H | CH$_3$ | OCH$_3$ | OCF$_2$H |
| OSO$_2$CF$_3$ | H | H | CH$_3$ | OCH$_3$ |
| CH$_2$OCH$_3$ | H | H | CH$_3$ | OCH$_3$ |
| CH$_2$OCH$_3$ | H | H | OCH$_3$ | OCH$_3$ |
| CH$_2$OCH$_3$ | H | CH$_3$ | CH$_3$ | OCF$_2$H |
| CH$_2$OCH$_3$ | H | CH$_3$ | CH$_3$ | CH$_3$ |
| CH$_2$OCF$_2$H | H | H | OCH$_3$ | OCH$_3$ |
| CH$_2$OCF$_2$H | H | H | OCH$_3$ | OCF$_2$H |
| CH$_2$OCF$_2$H | H | CH$_3$ | Cl | OCH$_3$ [b,d] |
| CH$_2$OCF$_2$H | H | CH$_3$ | CH$_3$ | OCH$_3$ |

TABLE 8

(a.) Z = N
(b.) Z = CH

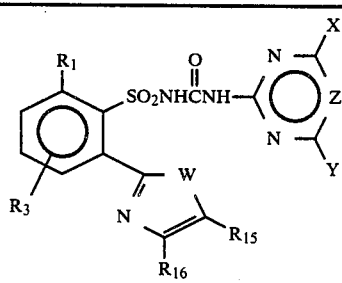

(c.) Z = N
(d.) Z = CH

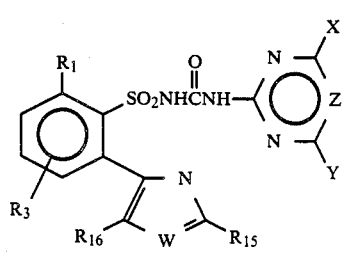

(e.) Z = N
(f.) Z = CH

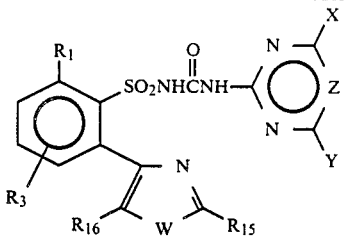

| R$_1$ | R$_3$ | W | R$_{15}$ | R$_{16}$ | X | Y |
|---|---|---|---|---|---|---|
| SCH$_3$ | H | O | H | H | CH$_3$ | OCH$_3$ |
| SCH$_3$ | H | O | H | H | OCH$_3$ | OCH$_3$ |
| SCH$_3$ | H | O | CH$_3$ | H | CH$_3$ | OCH$_3$ |
| SCH$_3$ | H | O | H | CH$_3$ | OCH$_3$ | OCH$_3$ |
| SCH$_3$ | H | O | CH$_3$ | CH$_3$ | CH$_3$ | CH$_3$ |
| SCH$_2$CH$_3$ | H | O | H | H | CH$_3$ | OCH$_3$ |
| SCH$_2$CH$_2$CH$_3$ | H | O | H | H | CH$_3$ | OCH$_3$ |
| S(O)CH$_3$ | H | O | H | H | CH$_3$ | OCH$_3$ |
| S(O)CH$_3$ | H | O | H | H | CH$_3$ | CH$_3$ |
| S(O)CH$_3$ | H | O | CH$_3$ | H | Cl | OCH$_3$ [b,d,f] |
| S(O)CH$_3$ | H | O | H | CH$_3$ | CH$_3$ | OCH$_3$ |
| S(O)$_2$CH$_3$ | H | O | H | H | OCH$_3$ | OCH$_3$ |
| S(O)$_2$CH$_3$ | H | O | CH$_3$ | H | CH$_3$ | OCH$_3$ |
| S(O)$_2$CH$_3$ | H | O | H | CH$_3$ | OCH$_3$ | OCH$_3$ |
| CF$_3$ | H | O | H | H | CH$_3$ | CH$_3$ |
| CF$_3$ | H | O | CH$_3$ | H | OCH$_3$ | OCH$_3$ |
| CF$_3$ | H | O | H | CH$_3$ | OCH$_3$ | OCH$_3$ |
| CF$_3$ | H | O | CH$_3$ | CH$_3$ | CH$_3$ | OCH$_3$ |
| N(CH$_3$)$_2$ | H | O | H | H | CH$_3$ | OCH$_3$ |
| N(CH$_3$)$_2$ | H | O | H | H | OCH$_3$ | OCH$_3$ |
| N(CH$_3$)$_2$ | H | O | CH$_3$ | H | CH$_3$ | OCH$_3$ |
| N(CH$_3$)$_2$ | H | O | H | CH$_3$ | OCH$_3$ | OCH$_3$ |
| N(CH$_3$)CH$_2$CH$_3$ | H | O | H | H | CH$_3$ | OCH$_3$ |
| N(CH$_2$CH$_3$)$_2$ | H | O | H | H | OCH$_3$ | OCH$_3$ |
| CO$_2$CH$_3$ | H | O | H | H | CH$_3$ | OCH$_3$ |
| CO$_2$CH$_3$ | H | O | CH$_3$ | H | OCH$_3$ | OCH$_3$ |
| CO$_2$CH$_3$ | H | O | H | CH$_3$ | CH$_3$ | CH$_3$ |
| CO$_2$CH$_2$CH$_2$Cl | H | O | H | H | CH$_3$ | OCH$_3$ |
| SO$_2$N(CH$_3$)$_2$ | H | O | H | H | OCH$_3$ | OCH$_3$ |
| SO$_2$N(CH$_3$)$_2$ | H | O | CH$_3$ | H | CH$_3$ | OCH$_3$ |
| C$_6$H$_5$ | H | O | H | H | CH$_3$ | CH$_3$ |
| C$_6$H$_5$ | H | O | H | H | CH$_3$ | OCH$_3$ |
| C$_6$H$_5$ | H | O | H | H | OCH$_3$ | OCH$_3$ |
| C$_6$H$_5$ | H | O | CH$_3$ | H | CH$_3$ | OCH$_3$ |
| C$_6$H$_5$ | H | O | H | CH$_3$ | OCH$_3$ | OCH$_3$ |
| C$_6$H$_5$ | H | O | CH$_3$ | CH$_3$ | OCH$_3$ | OCF$_2$H |
| 2'-C$_6$H$_4$Cl | H | O | H | H | CH$_3$ | OCH$_3$ |
| 2'-C$_6$H$_4$OCH$_3$ | H | O | H | H | OCH$_3$ | OCH$_3$ |
| 2'-C$_6$H$_4$CH$_3$ | H | O | H | H | Cl | OCH$_3$ [b,d,f] |
| 3'-C$_6$H$_4$Br | H | O | H | H | CH$_3$ | OCH$_3$ |
| 4'-C$_6$H$_4$F | H | O | H | H | OCH$_3$ | OCH$_3$ |
| CH$_2$CO$_2$CH$_3$ | H | O | H | H | CH$_3$ | OCH$_3$ |
| CH$_2$CO$_2$CH$_3$ | H | O | CH$_3$ | H | OCH$_3$ | OCH$_3$ |
| CH$_2$CO$_2$CH$_3$ | H | O | H | CH$_3$ | Cl | OCH$_3$ [b,d,f] |
| CHCO$_2$CH$_3$<br>\|<br>CH$_3$ | H | O | H | H | OCH$_3$ | OCF$_2$H |
| OSO$_2$CH$_3$ | H | O | H | H | CH$_3$ | OCH$_3$ |
| OSO$_2$CH$_3$ | H | O | CH$_3$ | H | OCH$_3$ | OCH$_3$ |
| OSO$_2$CH$_3$ | H | O | H | CH$_3$ | Cl | OCH$_3$ [b,d,f] |
| OSO$_2$CH$_3$ | H | O | CH$_3$ | CH$_3$ | OCH$_3$ | OCF$_2$H |
| OSO$_2$CF$_3$ | H | O | H | H | CH$_3$ | OCH$_3$ |
| CH$_2$OCH$_3$ | H | O | H | H | CH$_3$ | OCH$_3$ |
| CH$_2$OCH$_3$ | H | O | CH$_3$ | H | OCH$_3$ | OCH$_3$ |
| CH$_2$OCH$_3$ | H | O | H | CH$_3$ | OCH$_3$ | OCF$_2$H |
| CH$_2$OCH$_3$ | H | O | CH$_3$ | CH$_3$ | CH$_3$ | CH$_3$ |
| CH$_2$OCF$_2$H | H | O | H | H | OCH$_3$ | OCH$_3$ |
| CH$_2$OCF$_2$H | H | O | CH$_3$ | H | OCH$_3$ | OCF$_2$H |
| CH$_2$OCF$_2$H | H | O | H | CH$_3$ | Cl | OCH$_3$ [b,d,f] |
| CH$_2$OCF$_2$H | H | O | CH$_3$ | CH$_3$ | CH$_3$ | OCH$_3$ |
| SCH$_3$ | H | NCH$_3$ | H | H | CH$_3$ | OCH$_3$ |
| SCH$_3$ | H | NCH$_3$ | H | H | OCH$_3$ | OCH$_3$ |
| SCH$_3$ | H | NCH$_3$ | CH$_3$ | H | CH$_3$ | OCH$_3$ |
| SCH$_3$ | H | NCH$_3$ | H | CH$_3$ | OCH$_3$ | OCH$_3$ |
| SCH$_3$ | H | NH | CH$_3$ | CH$_3$ | CH$_3$ | CH$_3$ |
| SCH$_2$CH$_3$ | H | NCH$_3$ | H | H | CH$_3$ | OCH$_3$ |
| SCH$_2$CH$_2$CH$_3$ | H | NCH$_3$ | H | H | CH$_3$ | OCH$_3$ |

TABLE 8-continued

| | | | | | | |
|---|---|---|---|---|---|---|
| S(O)CH$_3$ | H | NH | H | H | CH$_3$ | CH$_3$ |
| S(O)CH$_3$ | H | NCH$_3$ | H | H | CH$_3$ | OCH$_3$ |
| S(O)CH$_3$ | H | NCH$_3$ | CH$_3$ | H | Cl | OCH$_3$[b,d,f] |
| S(O)CH$_3$ | H | NCH$_3$ | H | CH$_3$ | CH$_3$ | OCH$_3$ |
| S(O)$_2$CH$_3$ | H | NCH$_3$ | H | H | OCH$_3$ | OCH$_3$ |
| S(O)$_2$CH$_3$ | H | NCH$_3$ | CH$_3$ | H | CH$_3$ | OCH$_3$ |
| S(O)$_2$CH$_3$ | H | NCH$_3$ | H | CH$_3$ | OCH$_3$ | OCH$_3$ |
| CF$_3$ | H | NH | H | H | CH$_3$ | CH$_3$ |
| CF$_3$ | H | NCH$_3$ | CH$_3$ | H | OCH$_3$ | CH$_3$ |
| CF$_3$ | H | NCH$_3$ | H | CH$_3$ | OCH$_3$ | OCH$_3$ |
| CF$_3$ | H | NH | CH$_3$ | CH$_3$ | CH$_3$ | OCH$_3$ |
| N(CH$_3$)$_2$ | H | NCH$_3$ | H | H | CH$_3$ | OCH$_3$ |
| N(CH$_3$)$_2$ | H | NCH$_3$ | H | H | OCH$_3$ | OCH$_3$ |
| N(CH$_3$)$_2$ | H | NCH$_3$ | CH$_3$ | H | CH$_3$ | OCH$_3$ |
| N(CH$_3$)$_2$ | H | NCH$_3$ | H | CH$_3$ | OCH$_3$ | OCH$_3$ |
| N(CH$_3$)CH$_2$CH$_3$ | H | NCH$_3$ | H | H | CH$_3$ | OCH$_3$ |
| N(CH$_2$CH$_3$)$_2$ | H | NCH$_3$ | H | H | OCH$_3$ | OCH$_3$ |
| CO$_2$CH$_3$ | H | NCH$_3$ | H | H | CH$_3$ | OCH$_3$ |
| CO$_2$CH$_3$ | H | NCH$_3$ | CH$_3$ | H | OCH$_3$ | OCH$_3$ |
| CO$_2$CH$_3$ | H | NCH$_3$ | H | CH$_3$ | CH$_3$ | CH$_3$ |
| CO$_2$CH$_2$CH$_2$Cl | H | NCH$_3$ | H | H | CH$_3$ | OCH$_3$ |
| SO$_2$N(CH$_3$)$_2$ | H | NCH$_3$ | H | H | OCH$_3$ | OCH$_3$ |
| SO$_2$N(CH$_3$)$_2$ | H | NH | CH$_3$ | H | CH$_3$ | OCH$_3$ |
| C$_6$H$_5$ | H | NCH$_3$ | H | H | CH$_3$ | CH$_3$ |
| C$_6$H$_5$ | H | NCH$_3$ | H | H | CH$_3$ | OCH$_3$ |
| C$_6$H$_5$ | H | NCH$_3$ | H | H | OCH$_3$ | OCH$_3$ |
| C$_6$H$_5$ | H | NCH$_3$ | CH$_3$ | H | CH$_3$ | OCH$_3$ |
| C$_6$H$_5$ | H | NCH$_3$ | H | CH$_3$ | OCH$_3$ | OCH$_3$ |
| C$_6$H$_5$ | H | NCH$_3$ | CH$_3$ | CH$_3$ | OCH$_3$ | OCF$_2$H |
| 2'-C$_6$H$_4$Cl | H | NCH$_3$ | H | H | CH$_3$ | OCH$_3$ |
| 2'-C$_6$H$_4$OCH$_3$ | H | NCH$_3$ | H | H | OCH$_3$ | OCH$_3$ |
| 2'-C$_6$H$_4$CH$_3$ | H | NCH$_3$ | H | H | Cl | OCH$_3$[b,d,f] |
| 3'-C$_6$H$_4$Br | H | NH | H | H | CH$_3$ | OCH$_3$ |
| 4'-C$_6$H$_4$F | H | NCH$_3$ | H | H | OCH$_3$ | OCH$_3$ |
| CH$_2$CO$_2$CH$_3$ | H | NCH$_3$ | H | H | CH$_3$ | OCH$_3$ |
| CH$_2$CO$_2$CH$_3$ | H | NCH$_3$ | CH$_3$ | H | OCH$_3$ | OCH$_3$ |
| CH$_2$CO$_2$CH$_3$ | H | NCH$_3$ | H | CH$_3$ | Cl | OCH$_3$[b,d,f] |
| CHCO$_2$CH$_3$ \| CH$_3$ | H | NCH$_3$ | H | H | OCH$_3$ | OCF$_2$H |
| OSO$_2$CH$_3$ | H | NCH$_3$ | H | H | CH$_3$ | OCH$_3$ |
| OSO$_2$CH$_3$ | H | NCH$_3$ | CH$_3$ | H | OCH$_3$ | OCH$_3$ |
| OSO$_2$CH$_3$ | H | NCH$_3$ | H | H | Cl | OCH$_3$[b,d,f] |
| OSO$_2$CH$_3$ | H | NCH$_3$ | CH$_3$ | CH$_3$ | OCH$_3$ | OCF$_2$H |
| OSO$_2$CF$_3$ | H | NCH$_3$ | H | H | CH$_3$ | OCH$_3$ |
| CH$_2$OCH$_3$ | H | NCH$_3$ | H | H | CH$_3$ | OCH$_3$ |
| CH$_2$OCH$_3$ | H | NCH$_3$ | CH$_3$ | H | OCH$_3$ | OCH$_3$ |
| CH$_2$OCH$_3$ | H | NH | H | H | OCH$_3$ | OCF$_2$H |
| CH$_2$OCH$_3$ | H | NCH$_3$ | CH$_3$ | H | CH$_3$ | CH$_3$ |
| CH$_2$OCF$_2$H | H | NCH$_3$ | H | H | CH$_3$ | OCH$_3$ |
| CH$_2$OCF$_2$H | H | NCH$_3$ | CH$_3$ | H | OCH$_3$ | OCF$_2$H |
| CH$_2$OCF$_2$H | H | NCH$_3$ | H | CH$_3$ | Cl | OCH$_3$[b,d,f] |
| CH$_2$OCF$_2$H | H | NCH$_3$ | CH$_3$ | CH$_3$ | CH$_3$ | OCH$_3$ |
| SCH$_3$ | H | S | H | H | CH$_3$ | OCH$_3$ |
| SCH$_3$ | H | S | H | H | OCH$_3$ | OCH$_3$ |
| SCH$_3$ | H | S | CH$_3$ | H | CH$_3$ | OCH$_3$ |
| SCH$_3$ | H | S | H | CH$_3$ | OCH$_3$ | OCH$_3$ |
| SCH$_3$ | H | S | CH$_3$ | CH$_3$ | CH$_3$ | CH$_3$ |
| SCH$_3$ | 3-Cl | S | CH$_3$ | CH$_3$ | CH$_3$ | OCH$_3$ |
| SCH$_2$CH$_3$ | H | S | H | H | CH$_3$ | OCH$_3$ |
| SCH$_2$CH$_2$CH$_3$ | H | S | H | H | OCH$_3$ | OCH$_3$ |
| S(O)CH$_3$ | H | S | H | H | CH$_3$ | CH$_3$ |
| S(O)CH$_3$ | H | S | H | H | CH$_3$ | OCH$_3$ |
| S(O)CH$_3$ | H | S | CH$_3$ | H | Cl | OCH$_3$[b,d,f] |
| S(O)CH$_3$ | H | S | H | CH$_3$ | CH$_3$ | OCH$_3$ |
| S(O)$_2$CH$_3$ | H | S | H | H | OCH$_3$ | OCH$_3$ |
| S(O)$_2$CH$_3$ | H | S | CH$_3$ | H | OCH$_3$ | OCH$_3$ |
| CF$_3$ | H | S | H | H | CH$_3$ | CH$_3$ |
| CF$_3$ | H | S | CH$_3$ | H | OCH$_3$ | CH$_3$ |
| CF$_3$ | H | O | H | CH$_3$ | OCH$_3$ | OCH$_3$ |
| CF$_3$ | H | S | CH$_3$ | CH$_3$ | CH$_3$ | OCH$_3$ |
| N(CH$_3$)$_2$ | H | S | H | H | CH$_3$ | OCH$_3$ |
| N(CH$_3$)$_2$ | H | S | H | H | OCH$_3$ | OCH$_3$ |
| N(CH$_3$)$_2$ | H | S | CH$_3$ | H | CH$_3$ | OCH$_3$ |
| N(CH$_3$)$_2$ | H | S | H | CH$_3$ | OCH$_3$ | OCH$_3$ |
| N(CH$_3$)CH$_2$CH$_3$ | H | S | H | H | CH$_3$ | OCH$_3$ |
| N(CH$_2$CH$_3$)$_2$ | H | S | H | H | OCH$_3$ | OCH$_3$ |
| CO$_2$CH$_3$ | H | S | H | H | CH$_3$ | OCH$_3$ |
| CO$_2$CH$_3$ | H | S | CH$_3$ | H | OCH$_3$ | OCH$_3$ |
| CO$_2$CH$_3$ | H | S | H | CH$_3$ | CH$_3$ | CH$_3$ |
| CO$_2$CH$_2$CH$_2$Cl | H | S | H | H | CH$_3$ | OCH$_3$ |
| SO$_2$N(CH$_3$)$_2$ | H | S | H | H | OCH$_3$ | OCH$_3$ |
| SO$_2$N(CH$_3$)$_2$ | H | S | CH$_3$ | H | OCH$_3$ | OCH$_3$ |
| C$_6$H$_5$ | H | S | H | H | CH$_3$ | CH$_3$ |
| C$_6$H$_5$ | H | S | H | H | CH$_3$ | OCH$_3$ |
| C$_6$H$_5$ | H | S | H | H | OCH$_3$ | OCH$_3$ |
| C$_6$H$_5$ | H | S | CH$_3$ | H | CH$_3$ | OCH$_3$ |
| C$_6$H$_5$ | H | S | H | CH$_3$ | OCH$_3$ | OCH$_3$ |
| C$_6$H$_5$ | H | S | CH$_3$ | CH$_3$ | OCH$_3$ | OCF$_2$H |
| 2'-C$_6$H$_4$Cl | H | S | H | H | CH$_3$ | OCH$_3$ |
| 2'-C$_6$H$_4$OCH$_3$ | H | S | H | H | OCH$_3$ | OCH$_3$ |
| 2'-C$_6$H$_4$CH$_3$ | H | S | H | H | Cl | OCH$_3$[b,d,f] |
| 3'-C$_6$H$_4$Br | H | S | H | H | CH$_3$ | OCH$_3$ |
| 4'-C$_6$H$_4$F | H | S | H | H | OCH$_3$ | OCH$_3$ |
| CH$_2$CO$_2$CH$_3$ | H | S | H | H | CH$_3$ | OCH$_3$ |
| CH$_2$CO$_2$CH$_3$ | H | S | CH$_3$ | H | OCH$_3$ | OCH$_3$ |
| CH$_2$CO$_2$CH$_3$ | H | S | H | CH$_3$ | Cl | OCH$_3$[b,d,f] |
| CHCO$_2$CH$_3$ \| CH$_3$ | H | S | H | H | OCH$_3$ | OCF$_2$H |
| OSO$_2$CH$_3$ | H | S | H | H | CH$_3$ | OCH$_3$ |
| OSO$_2$CH$_3$ | H | S | CH$_3$ | H | OCH$_3$ | OCH$_3$ |
| OSO$_2$CH$_3$ | H | S | H | CH$_3$ | Cl | OCH$_3$[b,d,f] |
| OSO$_2$CH$_3$ | H | S | CH$_3$ | CH$_3$ | OCH$_3$ | OCF$_2$H |
| OSO$_2$CF$_3$ | H | S | H | H | CH$_3$ | OCH$_3$ |
| CH$_2$OCH$_3$ | H | S | H | H | CH$_3$ | OCH$_3$ |
| CH$_2$OCH$_3$ | H | S | CH$_3$ | H | OCH$_3$ | OCH$_3$ |
| CH$_2$OCH$_3$ | H | S | H | CH$_3$ | OCH$_3$ | OCF$_2$H |
| CH$_2$OCH$_3$ | H | S | CH$_3$ | CH$_3$ | CH$_3$ | CH$_3$ |
| CH$_2$OCF$_2$H | H | S | H | H | OCH$_3$ | OCH$_3$ |
| CH$_2$OCF$_2$H | H | S | CH$_3$ | H | OCH$_3$ | OCF$_2$H |
| CH$_2$OCF$_2$H | H | S | H | CH$_3$ | Cl | OCH$_3$[b,d,f] |
| CH$_2$OCF$_2$H | H | S | CH$_3$ | CH$_3$ | CH$_3$ | OCH$_3$ |

TABLE 9

(a.) Z = N
(b.) Z = CH

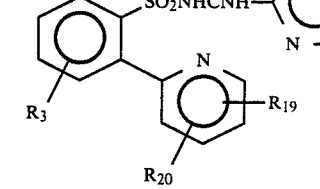

(c.) Z = N
(d.) Z = CH

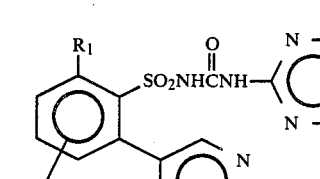

(e.) Z = N
(f.) Z = CH

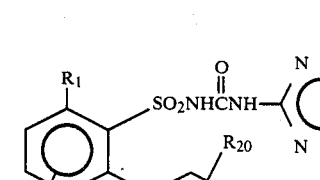

TABLE 9-continued

| R₁ | R₃ | R₁₉ | R₂₀ | X | Y |
|---|---|---|---|---|---|
| SCH₃ | H | H | H | CH₃ | OCH₃ |
| SCH₃ | H | H | H | OCH₃ | OCH₃ |
| SCH₃ | H | 3-CH₃ | H | CH₃ | OCH₃ |
| SCH₃ | H | 4-CH₃ | H | CH₃ | CH₃ |
| SCH₂CH₃ | H | H | H | CH₃ | OCH₃ |
| SCH₂CH₂CH₃ | H | H | H | CH₃ | OCH₃ |
| S(O)CH₃ | H | H | H | CH₃ | CH₃ |
| S(O)CH₃ | H | H | H | CH₃ | OCH₃ |
| S(O)CH₃ | H | 5-CH₃ | H | Cl[b,d,f] | OCH₃ |
| S(O)₂CH₃ | H | H | H | OCH₃ | OCH₃ |
| S(O)₂CH₃ | H | H | H | CH₃ | OCH₃ |
| S(O)₂CH₃ | H | 6-CH₃ | H | OCH₃ | OCH₃ |
| CF₃ | H | H | H | CH₃ | CH₃ |
| CF₃ | H | H | H | OCH₃ | OCH₃ |
| CF₃ | H | 3-CH₃ | 4-CH₃ | CH₃ | OCH₃ |
| N(CH₃)₂ | H | H | H | CH₃ | CH₃ |
| N(CH₃)₂ | H | H | H | OCH₃ | OCH₃ |
| N(CH₃)₂ | H | 3-CH₃ | 5-CH₃ | CH₃ | OCH₃ |
| N(CH₃)CH₂CH₃ | H | H | H | CH₃ | OCH₃ |
| N(CH₂CH₃)₂ | H | H | H | OCH₃ | OCH₃ |
| CO₂CH₃ | H | H | H | CH₃ | OCH₃ |
| CO₂CH₃ | H | H | H | OCH₃ | OCH₃ |
| CO₂CH₃ | H | 3-CH₃ | 6-CH₃ | CH₃ | CH₃ |
| CO₂CH₂CH₂Cl | H | H | H | CH₃ | OCH₃ |
| SO₂N(CH₃)₂ | H | H | H | OCH₃ | OCH₃ |
| SO₂N(CH₃)₂ | H | 4-CH₃ | 5-CH₃ | CH₃ | OCH₃ |
| C₆H₅ | H | H | H | CH₃ | CH₃ |
| C₆H₅ | H | H | H | CH₃ | OCH₃ |
| C₆H₅ | H | H | H | OCH₃ | OCH₃ |
| C₆H₅ | H | 4-CH₃ | 6-CH₃ | OCH₃ | OCH₃ |
| 2'-C₆H₄Cl | H | H | H | CH₃ | OCH₃ |
| 2'-C₆H₄CH₃ | H | H | H | OCH₃ | OCH₃ |
| 2'-C₆H₄OCH₃ | H | H | H | OCF₂H | OCH₃ |
| 3'-C₆H₄Br | H | H | H | CH₃ | OCH₃ |
| 4'-C₆H₄F | H | H | H | Cl[b,d,f] | OCH₃ |
| CH₂CO₂CH₃ | H | H | H | CH₃ | OCH₃ |
| CH₂CO₂CH₃ | H | H | H | OCH₃ | OCH₃ |
| CH₂CO₂CH₃ | H | 5-CH₃ | 6-CH₃ | Cl[b,d,f] | OCH₃ |
| CHCO₂CH₃<br>\|<br>CH₃ | H | H | H | OCH₃ | OCF₂H |
| OSO₂CH₃ | H | H | H | CH₃ | OCH₃ |
| OSO₂CH₃ | H | H | H | OCH₃ | OCH₃ |
| OSO₂CH₃ | H | 6-CH₃ | H | Cl[b,d,f] | OCH₃ |
| OSO₂CH₃ | H | 3-CH₃ | H | OCH₃ | OCF₂H |
| OSO₂CF₃ | H | H | H | CH₃ | OCH₃ |
| CH₂OCH₃ | H | H | H | CH₃ | OCH₃ |
| CH₂OCH₃ | H | H | H | OCH₃ | OCH₃ |
| CH₂OCH₃ | H | 6-CH₃ | H | OCH₃ | OCF₂H |
| CH₂OCH₃ | H | 3-CH₃ | H | CH₃ | CH₃ |
| CH₂OCF₂H | H | H | H | OCH₃ | OCH₃ |
| CH₂OCF₂H | H | H | H | OCH₃ | OCF₂H |
| CH₂OCF₂H | H | 6-CH₃ | H | Cl[b,d,f] | OCH₃ |
| CH₂OCF₂H | H | 3-CH₃ | H | CH₃ | OCH₃ |

TABLE 10

(a.) Z = N
(b.) Z = CH

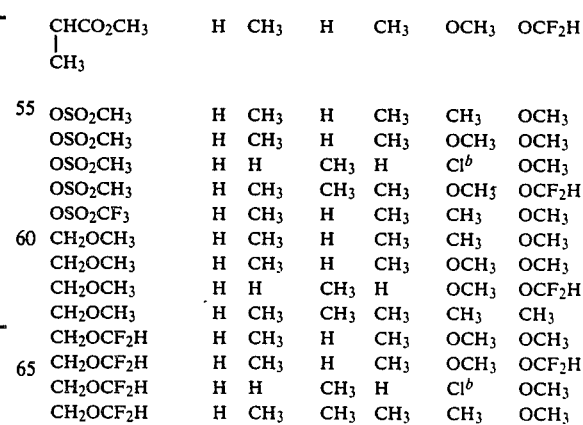

| R₁ | R₃ | R₂₁ | R₂₂ | R₂₃ | X | Y |
|---|---|---|---|---|---|---|
| SCH₃ | H | CH₃ | H | OCH₃ | CH₃ | OCH₃ |
| SCH₃ | H | CH₃ | H | CH₃ | OCH₃ | OCH₃ |
| SCH₃ | H | CH₃ | CH₃ | H | CH₃ | OCH₃ |
| SCH₃ | H | H | CH₃ | H | OCH₃ | OCH₃ |
| SCH₃ | H | CH₃ | CH₃ | CH₃ | CH₃ | CH₃ |
| SCH₂CH₃ | H | OCH₃ | H | OCH₃ | CH₃ | OCH₃ |

TABLE 10-continued (a.) Z = N
(b.) Z = CH

| R₁ | R₃ | R₂₁ | R₂₂ | R₂₃ | X | Y |
|---|---|---|---|---|---|---|
| SCH₂CH₂CH₃ | H | CH₃ | H | CH₃ | CH₃ | OCH₃ |
| S(O)CH₃ | H | CH₃ | H | OCH₃ | CH₃ | CH₃ |
| S(O)CH₃ | H | H | H | CH₃ | CH₃ | OCH₃ |
| S(O)CH₃ | H | H | H | CH₃ | Cl[b] | OCH₃ |
| S(O)CH₃ | H | H | CH₃ | CH₃ | CH₃ | OCH₃ |
| S(O)₂CH₃ | H | CH₃ | H | CH₃ | OCH₃ | OCH₃ |
| S(O)₂CH₃ | H | CH₃ | H | CH₃ | CH₃ | OCH₃ |
| S(O)₂CH₃ | H | H | CH₃ | H | OCH₃ | OCH₃ |
| CF₃ | H | OCH₃ | H | CH₃ | CH₃ | CH₃ |
| CF₃ | H | CH₃ | H | CH₃ | OCH₃ | CH₃ |
| CF₃ | H | H | CH₃ | H | OCH₃ | OCH₃ |
| CF₃ | H | CH₃ | CH₃ | CH₃ | CH₃ | OCH₃ |
| N(CH₃)₂ | H | CH₃ | H | CH₃ | CH₃ | OCH₃ |
| N(CH₃)₂ | H | CH₃ | H | CH₃ | OCH₃ | OCH₃ |
| N(CH₃)₂ | H | H | CH₃ | CH₃ | CH₃ | OCH₃ |
| N(CH₃)₂ | H | H | CH₃ | H | OCH₃ | OCH₃ |
| N(CH₃)CH₂CH₃ | H | CH₃ | H | CH₃ | CH₃ | OCH₃ |
| N(CH₂CH₃)₂ | H | CH₃ | H | CH₃ | OCH₃ | OCH₃ |
| CO₂CH₃ | H | CH₃ | H | CH₃ | CH₃ | OCH₃ |
| CO₂CH₃ | H | CH₃ | H | CH₃ | OCH₃ | OCH₃ |
| CO₂CH₃ | H | H | CH₃ | H | CH₃ | CH₃ |
| CO₂CH₂CH₂Cl | H | CH₃ | H | CH₃ | CH₃ | OCH₃ |
| SO₂N(CH₃)₂ | H | CH₃ | H | CH₃ | OCH₃ | OCH₃ |
| SO₂N(CH₃)₂ | H | CH₃ | H | CH₃ | CH₃ | OCH₃ |
| C₆H₅ | H | CH₃ | H | CH₃ | CH₃ | CH₃ |
| C₆H₅ | H | CH₃ | H | CH₃ | CH₃ | OCH₃ |
| C₆H₅ | H | CH₃ | H | CH₃ | OCH₃ | OCH₃ |
| C₆H₅ | H | CH₃ | CH₃ | CH₃ | CH₃ | OCH₃ |
| C₆H₅ | H | H | CH₃ | H | OCH₃ | OCH₃ |
| 2'-C₆H₄Cl | H | CH₃ | H | CH₃ | CH₃ | OCH₃ |
| 3'-C₆H₄Br | H | CH₃ | H | OCH₃ | OCH₃ | OCH₃ |
| 4'-C₆H₄F | H | CH₃ | H | CH₃ | CH₃ | OCH₃ |
| 2'-C₆H₄CH₃ | H | CH₃ | H | CH₃ | OCH₃ | OCH₃ |
| 2'-C₆H₄OCH₃ | H | CH₃ | H | CH₃ | OCH₃ | OCH₃ |
| CH₂CO₂CH₃ | H | CH₃ | H | CH₃ | CH₃ | OCH₃ |
| CH₂CO₂CH₃ | H | CH₃ | H | CH₃ | OCH₃ | OCH₃ |
| CH₂CO₂CH₃ | H | H | CH₃ | CH₃ | Cl[b] | OCH₃ |
| CHCO₂CH₃<br>\|<br>CH₃ | H | CH₃ | H | CH₃ | OCH₃ | OCF₂H |
| OSO₂CH₃ | H | CH₃ | H | CH₃ | CH₃ | OCH₃ |
| OSO₂CH₃ | H | CH₃ | H | CH₃ | OCH₃ | OCH₃ |
| OSO₂CH₃ | H | H | CH₃ | H | Cl[b] | OCH₃ |
| OSO₂CH₃ | H | CH₃ | CH₃ | CH₃ | OCH₅ | OCF₂H |
| OSO₂CF₃ | H | CH₃ | H | CH₃ | CH₃ | OCH₃ |
| CH₂OCH₃ | H | CH₃ | H | CH₃ | CH₃ | OCH₃ |
| CH₂OCH₃ | H | CH₃ | H | CH₃ | OCH₃ | OCH₃ |
| CH₂OCH₃ | H | H | CH₃ | H | OCH₃ | OCF₂H |
| CH₂OCH₃ | H | CH₃ | CH₃ | CH₃ | CH₃ | CH₃ |
| CH₂OCF₂H | H | CH₃ | H | CH₃ | OCH₃ | OCH₃ |
| CH₂OCF₂H | H | CH₃ | H | CH₃ | OCH₃ | OCF₂H |
| CH₂OCF₂H | H | H | CH₃ | H | Cl[b] | OCH₃ |
| CH₂OCF₂H | H | CH₃ | CH₃ | CH₃ | CH₃ | OCH₃ |

TABLE 11

(a.) Z = N
(b.) Z = CH

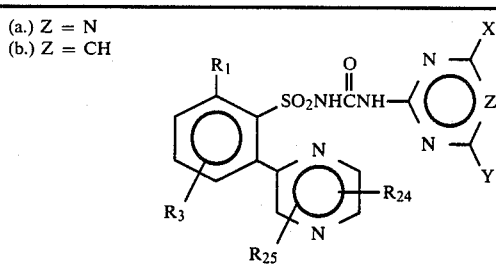

| R1 | R3 | R24 | R25 | X | Y |
|---|---|---|---|---|---|
| SCH3 | H | H | H | CH3 | OCH3 |
| SCH3 | H | H | H | OCH3 | OCH3 |
| SCH3 | H | 3-CH3 | H | CH3 | OCH3 |
| SCH3 | H | 3-CH3 | H | CH3 | CH3 |
| SCH2CH3 | H | H | H | CH3 | OCH3 |
| SCH2CH2CH3 | H | H | H | CH3 | OCH3 |
| S(O)CH3 | H | H | H | CH3 | CH3 |
| S(O)CH3 | H | H | H | CH3 | OCH3 |
| S(O)CH3 | H | 5-CH3 | H | Cl[b] | OCH3 |
| S(O)2CH3 | H | H | H | OCH3 | OCH3 |
| S(O)2CH3 | H | H | H | CH3 | OCH3 |
| S(O)2CH3 | H | 6-CH3 | H | OCH3 | OCH3 |
| CF3 | H | H | H | CH3 | CH3 |
| CF3 | H | H | H | CH3 | OCH3 |
| CF3 | H | 3-CH3 | 5-CH3 | CH3 | OCH3 |
| N(CH3)2 | H | H | H | CH3 | OCH3 |
| N(CH3)2 | H | H | H | OCH3 | OCH3 |
| N(CH3)2 | H | 3-CH3 | 6-CH3 | CH3 | OCH3 |
| N(CH3)CH2CH3 | H | H | H | CH3 | OCH3 |
| N(CH2CH3)2 | H | H | H | OCH3 | OCH3 |
| CO2CH3 | H | H | H | CH3 | OCH3 |
| CO2CH3 | H | H | H | OCH3 | OCH3 |
| CO2CH3 | H | 5-CH3 | 6-CH3 | CH3 | CH3 |
| CO2CH2CH2Cl | H | H | H | CH3 | OCH3 |
| SO2N(CH3)2 | H | H | H | OCH3 | OCH3 |
| SO2N(CH3)2 | H | 3-CH3 | 6-CH3 | CH3 | OCH3 |
| C6H5 | H | H | H | CH3 | CH3 |
| C6H5 | H | H | H | CH3 | OCH3 |
| C6H5 | H | H | H | OCH3 | OCH3 |
| C6H5 | H | 5-CH3 | 6-CH3 | OCH3 | OCH3 |
| 2'-C6H4Cl | H | H | H | CH3 | OCH3 |
| 2'-C6H4CH3 | H | H | H | OCH3 | OCH3 |
| 2'-C6H4OCH3 | H | H | H | OCF2H | OCH3 |
| 3'-C6H4Br | H | H | H | CH3 | OCH3 |
| 4'-C6H4F | H | H | H | Cl[b] | OCH3 |
| CH2CO2CH3 | H | H | H | CH3 | OCH3 |
| CH2CO2CH3 | H | H | H | OCH3 | OCH3 |
| CH2CO2CH3 | H | 3-CH3 | 5-CH3 | Cl[b] | OCH3 |
| CHCO2CH3<br>\|<br>CH3 | H | H | H | OCH3 | OCF2H |
| OSO2CH3 | H | H | H | CH3 | OCH3 |
| OSO2CH3 | H | H | H | OCH3 | OCH3 |
| OSO2CH3 | H | 6-CH3 | H | Cl[b] | OCH3 |
| OSO2CH3 | H | 6-CH3 | H | OCH3 | OCF2H |
| OSO2CF3 | H | H | H | OCH3 | OCH3 |
| CH2OCH3 | H | H | H | CH3 | OCH3 |
| CH2OCH3 | H | H | H | OCH3 | OCH3 |
| CH2OCH3 | H | 5-CH3 | H | OCH3 | OCF2H |
| CH2OCH3 | H | 6-CH3 | H | CH3 | CH3 |
| CH2OCF2H | H | H | H | OCH3 | OCH3 |
| CH2OCF2H | H | H | H | OCH3 | OCF2H |
| CH2OCF2H | H | 5-CH3 | H | Cl[b] | OCH3 |
| CH2OCF2H | H | 6-CH3 | H | CH3 | OCH3 |

TABLE 12

(a.) Z = N
(b.) Z = CH

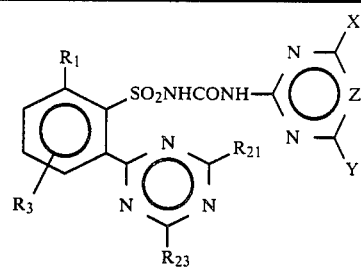

| R1 | R3 | R21 | R23 | X | Y |
|---|---|---|---|---|---|
| SCH3 | H | CH3 | CH3 | CH3 | OCH3 |
| SCH3 | H | H | H | OCH3 | OCH3 |
| SCH3 | H | CH3 | CH3 | CH3 | OCH3 |
| SCH3 | H | CH3 | CH3 | CH3 | CH3 |
| SCH2CH3 | H | CH3 | CH3 | CH3 | OCH3 |
| SCH2CH2CH3 | H | CH3 | CH3 | CH3 | OCH3 |
| S(O)CH3 | H | CH3 | CH3 | CH3 | CH3 |
| S(O)CH3 | H | CH3 | CH3 | CH3 | OCH3 |
| S(O)CH3 | H | CH3 | OCH3 | Cl[b] | OCH3 |
| S(O)2CH3 | H | CH3 | CH3 | OCH3 | OCH3 |
| S(O)2CH3 | H | H | CH3 | CH3 | OCH3 |
| S(O)2CH3 | H | OCH3 | OCH3 | OCH3 | OCH3 |
| CF3 | H | CH3 | CH3 | CH3 | CH3 |
| CF3 | H | CH3 | CH3 | CH3 | OCH3 |
| CF3 | H | OCH3 | CH3 | CH3 | OCH3 |
| N(CH3)2 | H | CH3 | CH3 | CH3 | OCH3 |
| N(CH3)2 | H | CH3 | CH3 | OCH3 | OCH3 |
| N(CH3)2 | H | CH3 | OCH3 | CH3 | OCH3 |
| N(CH3)CH2CH3 | H | CH3 | CH3 | CH3 | OCH3 |
| N(CH2CH3)2 | H | H | H | OCH3 | OCH3 |
| CO2CH3 | H | H | OCH3 | CH3 | OCH3 |
| CO2CH3 | H | CH3 | CH3 | OCH3 | OCH3 |
| CO2CH3 | H | OCH3 | OCH3 | CH3 | CH3 |
| CO2CH2CH2Cl | H | CH3 | CH3 | CH3 | OCH3 |
| SO2N(CH3)2 | H | CH3 | CH3 | OCH3 | OCH3 |
| SO2N(CH3)2 | H | OCH3 | OCH3 | CH3 | OCH3 |
| C6H5 | H | H | OCH3 | CH3 | CH3 |
| C6H5 | H | CH3 | CH3 | CH3 | OCH3 |
| C6H5 | H | CH3 | OCH3 | OCH3 | OCH3 |
| C6H5 | H | CH3 | OCH3 | OCH3 | OCH3 |
| 2'-C6H4Cl | H | CH3 | CH3 | CH3 | OCH3 |
| 2'-C6H4CH3 | H | CH3 | CH3 | OCH3 | OCH3 |
| 2'-C6H4OCH3 | H | H | CH3 | OCF2H | OCH3 |
| 3'-C6H4Br | H | CH3 | CH3 | CH3 | OCH3 |
| 4'-C6H4F | H | CH3 | CH3 | Cl[b] | OCH3 |
| CH2CO2CH3 | H | OCH3 | OCH3 | CH3 | OCH3 |
| CH2CO2CH3 | H | CH3 | CH3 | OCH3 | OCH3 |
| CH2CO2CH3 | H | CH3 | CH3 | Cl | OCH3[b] |
| CHCO2CH3<br>\|<br>CH3 | H | CH3 | CH3 | OCH3 | OCF2H |
| OSO2CH3 | H | CH3 | CH3 | CH3 | OCH3 |
| OSO2CH3 | H | CH3 | CH3 | OCH3 | OCH3 |
| OSO2CH3 | H | OCH3 | H | Cl[b] | OCH3 |
| OSO2CH3 | H | CH3 | CH3 | OCH3 | OCF2H |
| OSO2CF3 | H | CH3 | CH3 | OCH3 | OCH3 |
| CH2OCH3 | H | CH3 | CH3 | CH3 | OCH3 |
| CH2OCH3 | H | CH3 | CH3 | OCH3 | OCH3 |
| CH2OCH3 | H | CH3 | H | OCH3 | OCF2H |
| CH2OCH3 | H | CH3 | CH3 | CH3 | CH3 |
| CH2OCF2H | H | CH3 | CH3 | OCH3 | OCH3 |
| CH2OCF2H | H | CH3 | CH3 | OCH3 | OCF2H |
| CH2OCF2H | H | CH3 | H | Cl[b] | OCH3 |
| CH2OCF2H | H | CH3 | CH3 | CH3 | OCH3 |

TABLE 13

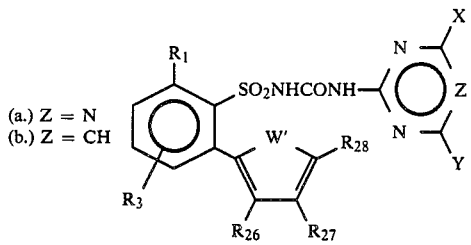

(a.) Z = N
(b.) Z = CH

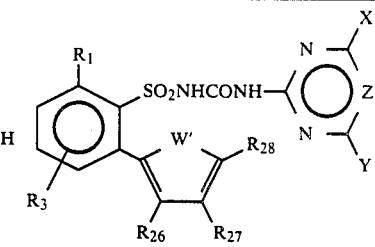

(a.) Z = N
(b.) Z = CH

| R₁ | R₃ | W' | R₂₆ | R₂₇ | R₂₈ | X | Y |
|---|---|---|---|---|---|---|---|
| SCH₃ | H | O | H | H | H | CH₃ | OCH₃ |
| SCH₃ | H | O | H | H | H | OCH₃ | OCH₃ |
| SCH₃ | H | O | CH₃ | H | CH₃ | CH₃ | OCH₃ |
| SCH₃ | H | O | H | CH₃ | H | OCH₃ | OCH₃ |
| SCH₃ | H | O | CH₃ | CH₃ | CH₃ | CH₃ | CH₃ |
| SCH₂CH₃ | H | O | H | H | H | CH₃ | OCH₃ |
| SCH₂CH₂CH₃ | H | O | H | H | H | CH₃ | OCH₃ |
| S(O)CH₃ | H | O | H | H | H | CH₃ | CH₃ |
| S(O)CH₃ | H | O | H | H | H | CH₃ | OCH₃ |
| S(O)CH₃ | H | O | CH₃ | H | CH₃ | Cl[b] | OCH₃ |
| S(O)CH₃ | H | O | H | CH₃ | CH₃ | CH₃ | OCH₃ |
| S(O)₂CH₃ | H | O | H | H | H | OCH₃ | OCH₃ |
| S(O)₂CH₃ | H | O | CH₃ | H | CH₃ | CH₃ | OCH₃ |
| S(O)₂CH₃ | H | O | H | CH₃ | H | OCH₃ | OCH₃ |
| CF₃ | H | O | H | H | H | CH₃ | CH₃ |
| CF₃ | H | O | CH₃ | H | CH₃ | OCH₃ | CH₃ |
| CF₃ | H | O | H | CH₃ | H | OCH₃ | OCH₃ |
| CF₃ | H | O | CH₃ | CH₃ | CH₃ | CH₃ | OCH₃ |
| N(CH₃)₂ | H | O | H | H | H | CH₃ | OCH₃ |
| N(CH₃)₂ | H | O | H | H | H | OCH₃ | OCH₃ |
| N(CH₃)₂ | H | O | CH₃ | H | CH₃ | CH₃ | CH₃ |
| N(CH₃)₂ | H | O | H | CH₃ | H | OCH₃ | OCH₃ |
| N(CH₃)CH₂CH₃ | H | O | H | H | H | CH₃ | OCH₃ |
| N(CH₂CH₃)₂ | H | O | H | H | H | OCH₃ | OCH₃ |
| CO₂CH₃ | H | O | H | H | H | CH₃ | OCH₃ |
| CO₂CH₃ | H | O | CH₃ | H | CH₃ | OCH₃ | OCH₃ |
| CO₂CH₃ | H | O | H | CH₃ | H | CH₃ | CH₃ |
| CO₂CH₂CH₂Cl | H | O | H | H | H | CH₃ | OCH₃ |
| SO₂N(CH₃)₂ | H | O | H | H | H | OCH₃ | OCH₃ |
| SO₂N(CH₃)₂ | H | O | CH₃ | H | CH₃ | CH₃ | OCH₃ |
| C₆H₅ | H | O | H | H | H | CH₃ | CH₃ |
| C₆H₅ | H | O | H | H | H | CH₃ | OCH₃ |
| C₆H₅ | H | O | H | H | H | OCH₃ | OCH₃ |
| C₆H₅ | H | O | CH₃ | H | CH₃ | CH₃ | CH₃ |
| C₆H₅ | H | O | H | CH₃ | H | OCH₃ | OCH₃ |
| 2'-C₆H₄Cl | H | O | H | H | H | CH₃ | OCH₃ |
| 2'-C₆H₄Br | H | O | H | H | H | OCH₃ | OCH₃ |
| 2'-C₆H₄F | H | O | H | H | H | CH₃ | OCH₃ |
| 3'-C₆H₄CH₃ | H | O | H | H | H | OCH₃ | OCH₃ |
| 4'-C₆H₄OCH₃ | H | O | H | H | H | OCH₃ | OCF₂H |
| CH₂CO₂CH₃ | H | O | H | H | H | CH₃ | OCH₃ |
| CH₂CO₂CH₃ | H | O | CH₃ | H | CH₃ | OCH₃ | OCH₃ |
| CH₂CO₂CH₃ | H | O | H | CH₃ | CH₃ | Cl[b] | OCH₃ |
| CHCO₂CH₃<br>\|<br>CH₃ | H | O | H | H | H | OCH₃ | OCF₂H |
| OSO₂CH₃ | H | O | H | H | H | CH₃ | OCH₃ |
| OSO₂CH₃ | H | O | CH₃ | H | CH₃ | OCH₃ | OCH₃ |
| OSO₂CH₃ | H | O | H | CH₃ | H | Cl[b] | OCH₃ |
| OSO₂CH₃ | H | O | CH₃ | CH₃ | CH₃ | OCH₃ | OCF₂H |
| OSO₂CF₃ | H | O | H | H | H | CH₃ | OCH₃ |
| CH₂OCH₃ | H | O | H | H | H | CH₃ | OCH₃ |
| CH₂OCH₃ | H | O | CH₃ | H | CH₃ | OCH₃ | OCH₃ |
| CH₂OCH₃ | H | O | H | CH₃ | H | OCH₃ | OCF₂H |
| CH₂OCH₃ | H | O | CH₃ | CH₃ | CH₃ | CH₃ | CH₃ |
| CH₂OCF₂H | H | O | H | H | H | OCH₃ | OCH₃ |
| CH₂OCF₂H | H | O | CH₃ | H | CH₃ | OCH₃ | OCF₂H |
| CH₂OCF₂H | H | O | H | CH₃ | H | Cl[b] | OCH₃ |
| CH₂OCF₂H | H | O | CH₃ | CH₃ | CH₃ | CH₃ | CH₃ |

| R₁ | R₃ | W' | R₂₆ | R₂₇ | R₂₈ | X | Y |
|---|---|---|---|---|---|---|---|
| SCH₃ | H | S | H | H | H | CH₃ | OCH₃ |
| SCH₃ | H | S | H | H | H | OCH₃ | OCH₃ |
| SCH₃ | H | S | CH₃ | H | CH₃ | CH₃ | OCH₃ |
| SCH₃ | H | S | H | CH₃ | H | OCH₃ | OCH₃ |
| SCH₃ | H | S | CH₃ | CH₃ | CH₃ | CH₃ | CH₃ |
| SCH₂CH₃ | H | S | H | H | H | CH₃ | OCH₃ |
| SCH₂CH₂CH₃ | H | S | H | H | H | CH₃ | OCH₃ |
| S(O)CH₃ | H | S | H | H | H | CH₃ | CH₃ |
| S(O)CH₃ | H | S | H | H | H | CH₃ | OCH₃ |
| S(O)CH₃ | H | S | CH₃ | H | CH₃ | Cl[b] | OCH₃ |
| S(O)CH₃ | H | S | H | CH₃ | CH₃ | CH₃ | OCH₃ |
| S(O)₂CH₃ | H | S | H | H | H | OCH₃ | OCH₃ |
| S(O)₂CH₃ | H | S | CH₃ | H | CH₃ | CH₃ | OCH₃ |
| S(O)₂CH₃ | H | S | H | CH₃ | H | OCH₃ | OCH₃ |
| CF₃ | H | S | H | H | H | CH₃ | CH₃ |
| CF₃ | H | S | CH₃ | H | CH₃ | OCH₃ | CH₃ |
| CF₃ | H | S | H | CH₃ | H | OCH₃ | OCH₃ |
| CF₃ | H | S | CH₃ | CH₃ | CH₃ | CH₃ | OCH₃ |
| N(CH₃)₂ | H | S | H | H | H | CH₃ | OCH₃ |
| N(CH₃)₂ | H | S | H | H | H | OCH₃ | OCH₃ |
| N(CH₃)₂ | H | S | CH₃ | H | CH₃ | CH₃ | CH₃ |
| N(CH₃)₂ | H | S | H | CH₃ | H | OCH₃ | OCH₃ |
| N(CH₃)CH₂CH₃ | H | S | H | H | H | CH₃ | OCH₃ |
| N(CH₂CH₃)₂ | H | S | H | H | H | OCH₃ | OCH₃ |
| CO₂CH₃ | H | S | H | H | H | CH₃ | OCH₃ |
| CO₂CH₃ | H | S | CH₃ | H | CH₃ | OCH₃ | OCH₃ |
| CO₂CH₃ | H | S | H | CH₃ | H | CH₃ | CH₃ |
| CO₂CH₂CH₂Cl | H | S | H | H | H | CH₃ | OCH₃ |
| SO₂N(CH₃)₂ | H | S | H | H | H | OCH₃ | OCH₃ |
| SO₂N(CH₃)₂ | H | S | CH₃ | H | CH₃ | CH₃ | OCH₃ |
| C₆H₅ | H | S | H | H | H | CH₃ | CH₃ |
| C₆H₅ | H | S | H | H | H | CH₃ | OCH₃ |
| C₆H₅ | H | S | H | H | H | OCH₃ | OCH₃ |
| C₆H₅ | H | S | CH₃ | H | CH₃ | CH₃ | CH₃ |
| C₆H₅ | H | S | H | CH₃ | H | OCH₃ | OCH₃ |
| 2'-C₆H₄Cl | H | S | H | H | H | CH₃ | OCH₃ |
| 2'-C₆H₄Br | H | S | H | H | H | OCH₃ | OCH₃ |
| 2'-C₆H₄F | H | S | H | H | H | CH₃ | OCH₃ |
| 3'-C₆H₄CH₃ | H | S | H | H | H | OCH₃ | OCH₃ |
| 4'-C₆H₄OCH₃ | H | S | H | H | H | OCH₃ | OCF₂H |
| CH₂CO₂CH₃ | H | S | H | H | H | CH₃ | OCH₃ |
| CH₂CO₂CH₃ | H | S | CH₃ | H | CH₃ | OCH₃ | OCH₃ |
| CH₂CO₂CH₃ | H | S | H | CH₃ | CH₃ | Cl[b] | OCH₃ |
| CHCO₂CH₃<br>\|<br>CH₃ | H | S | H | H | H | OCH₃ | OCF₂H |
| OSO₂CH₃ | H | S | H | H | H | CH₃ | OCH₃ |
| OSO₂CH₃ | H | S | CH₃ | H | CH₃ | OCH₃ | OCH₃ |
| OSO₂CH₃ | H | S | H | CH₃ | H | Cl[b] | OCH₃ |
| OSO₂CH₃ | H | S | CH₃ | CH₃ | CH₃ | OCH₃ | OCF₂H |
| OSO₂CF₃ | H | S | H | H | H | CH₃ | OCH₃ |
| CH₂OCH₃ | H | S | H | H | H | CH₃ | OCH₃ |
| CH₂OCH₃ | H | S | CH₃ | H | CH₃ | OCH₃ | OCF₂H |
| CH₂OCH₃ | H | S | H | CH₃ | H | CH₃ | CH₃ |
| CH₂OCF₂H | H | S | H | H | H | OCH₃ | OCH₃ |
| CH₂OCF₂H | H | S | CH₃ | H | CH₃ | OCH₃ | OCF₂H |
| CH₂OCF₂H | H | S | H | CH₃ | H | Cl[b] | OCH₃ |
| CH₂OCF₂H | H | S | CH₃ | CH₃ | CH₃ | CH₃ | OCH₃ |

TABLE 14

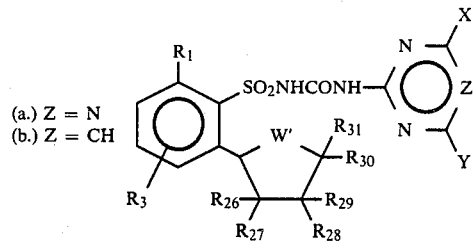

(a.) Z = N
(b.) Z = CH

| R₁ | R₃ | W' | R₂₆ | R₂₇ | R₂₈ | R₂₉ | R₃₀ | R₃₁ | X | Y |
|---|---|---|---|---|---|---|---|---|---|---|
| SCH₃ | H | O | H | H | H | H | H | H | CH₃ | OCH₃ |
| SCH₃ | H | O | H | H | H | H | H | H | OCH₃ | OCH₃ |
| SCH₃ | H | O | CH₃ | H | H | H | H | H | OCH₃ | OCH₃ |
| SCH₃ | H | O | H | H | CH₃ | H | H | H | Cl[b] | OCH₃ |
| SCH₃ | H | O | H | H | H | H | CH₃ | H | CH₃ | CH₃ |
| SCH₂CH₃ | H | O | CH₃ | H | CH₃ | H | CH₃ | H | CH₃ | OCH₃ |
| SCH₂CH₂CH₃ | H | O | H | H | H | H | H | H | OCH₃ | OCH₃ |
| S(O)CH₃ | H | O | CH₃ | H | CH₃ | CH₃ | CH₃ | H | CH₃ | OCH₃ |
| S(O)CH₃ | H | O | CH₃ | H | CH₃ | H | CH₃ | H | OCH₃ | OCH₃ |
| S(O)CH₃ | H | O | H | H | H | H | H | H | Cl[b] | OCH₃ |
| S(O)CH₃ | H | O | H | H | H | H | H | H | CH₃ | OCH₃ |
| S(O)₂CH₃ | H | O | H | H | H | H | H | H | OCH₃ | OCH₃ |
| S(O)₂CH₃ | H | O | CH₃ | CH₃ | H | H | CH₃ | CH₃ | CH₃ | OCH₃ |
| S(O)₂CH₃ | H | O | H | H | CH₃ | CH₃ | H | H | OCH₃ | OCH₃ |
| CF₃ | H | O | H | H | H | H | H | H | CH₃ | OCH₃ |
| CF₃ | H | O | CH₃ | H | H | H | H | H | OCH₃ | OCH₃ |
| CF₃ | H | O | H | H | CH₃ | H | H | H | Cl[b] | OCH₃ |
| CF₃ | H | O | H | H | H | H | CH₃ | H | CH₃ | OCH₃ |
| N(CH₃)₂ | H | O | H | H | H | H | H | H | CH₃ | OCH₃ |
| N(CH₃)₂ | H | O | H | H | H | H | H | H | OCH₃ | OCH₃ |
| N(CH₃)₂ | H | O | H | H | H | H | H | H | Cl[b] | OCH₃ |
| N(CH₃)₂ | H | O | CH₃ | H | H | H | H | CH₃ | OCH₃ | OCH₃ |
| N(CH₃)CH₂CH₃ | H | O | H | H | H | H | H | H | OCH₃ | OCH₃ |
| N(CH₂CH₃)₂ | H | O | H | H | H | H | H | H | OCH₃ | OCH₃ |
| CO₂CH₃ | H | O | H | H | H | H | H | H | CH₃ | OCH₃ |
| CO₂CH₃ | H | O | H | H | CH₃ | H | H | H | OCH₃ | OCH₃ |
| CO₂CH₃ | H | O | H | H | CH₃ | CH₃ | H | H | CH₃ | CH₃ |
| CO₂CH₂CH₂Cl | H | O | H | H | H | H | H | H | CH₃ | OCH₃ |
| SO₂N(CH₃)₂ | H | O | H | H | H | H | H | H | OCH₃ | OCH₃ |
| SO₂N(CH₃)₂ | H | O | H | H | H | H | H | H | CH₃ | OCH₃ |
| C₆H₅ | H | O | H | H | H | H | H | H | CH₃ | CH₃ |
| C₆H₅ | H | O | H | H | H | H | H | H | CH₃ | OCH₃ |
| C₆H₅ | H | O | H | H | H | H | H | H | OCH₃ | OCH₃ |
| C₆H₅ | H | O | CH₃ | H | CH₃ | H | CH₃ | H | CH₃ | OCH₃ |
| C₆H₅ | H | O | CH₃ | H | H | H | CH₃ | H | OCH₃ | OCH₃ |
| 2'-C₆H₄Cl | H | O | H | H | H | H | H | H | CH₃ | OCH₃ |
| 2'-C₆H₄Br | H | O | CH₃ | H | CH₃ | H | H | H | OCH₃ | OCH₃ |
| 2'-C₆H₄F | H | O | H | H | H | H | H | CH₃ | CH₃ | CH₃ |
| 3'-C₆H₄CH₃ | H | O | H | H | H | H | H | H | OCH₃ | OCH₃ |
| 4'-C₆H₄OCH₃ | H | O | H | H | H | H | H | H | OCF₂H | OCH₃ |
| CH₂CO₂CH₃ | H | O | H | H | H | H | H | H | CH₃ | OCH₃ |
| CH₂CO₂CH₃ | H | O | H | H | CH₃ | CH₃ | H | H | OCH₃ | OCH₃ |
| CH₂CO₂CH₃ | H | O | H | H | H | H | H | H | Cl[b] | OCH₃ |
| CHCO₂CH₃<br>\|<br>CH₃ | H | O | H | H | H | H | H | H | OCF₂H | OCH₃ |
| OSO₂CH₃ | H | O | H | H | H | H | H | H | CH₃ | OCH₃ |
| OSO₂CH₃ | H | O | H | H | H | H | H | H | OCH₃ | OCH₃ |
| OSO₂CH₃ | H | O | H | H | H | H | H | H | Cl[b] | OCH₃ |
| OSO₂CH₃ | H | O | H | H | H | H | H | H | OCF₂H | OCH₃ |
| OSO₂CF₃ | H | O | H | H | H | H | H | CH₃ | CH₃ | OCH₃ |
| CH₂OCH₃ | H | O | H | H | H | H | H | H | CH₃ | OCH₃ |
| CH₂OCH₃ | H | O | H | H | H | H | H | H | CH₃ | CH₃ |
| CH₂OCH₃ | H | O | H | H | CH₃ | H | H | H | OCF₂H | OCH₃ |
| CH₂OCH₃ | H | O | H | H | CH₃ | H | CH₃ | H | CH₃ | CH₃ |
| CH₂OCF₂H | H | O | H | H | H | H | H | H | CH₃ | OCH₃ |
| CH₂OCF₂H | H | O | H | H | H | H | H | H | OCH₃ | OCH₃ |
| CH₂OCF₂H | H | O | CH₃ | H | H | H | CH₃ | H | Cl[b] | OCH₃ |
| CH₂OCF₂H | H | O | CH₃ | CH₃ | CH₃ | CH₃ | H | H | CH₃ | OCH₃ |
| SCH₃ | H | S | H | H | H | H | H | H | CH₃ | OCH₃ |
| SCH₃ | H | S | H | H | H | H | H | H | OCH₃ | OCH₃ |
| SCH₃ | H | S | CH₃ | H | H | H | H | H | OCH₃ | OCH₃ |
| SCH₃ | H | S | H | H | CH₃ | H | H | H | Cl[b] | OCH₃ |
| SCH₃ | H | S | H | H | H | H | CH₃ | H | CH₃ | CH₃ |
| SCH₂CH₃ | H | S | CH₃ | H | CH₃ | H | CH₃ | H | CH₃ | OCH₃ |
| SCH₂CH₂CH₃ | H | S | H | H | H | H | H | H | OCH₃ | OCH₃ |

TABLE 14-continued (a.) Z = N
(b.) Z = CH

| R₁ | R₃ | W' | R₂₆ | R₂₇ | R₂₈ | R₂₉ | R₃₀ | R₃₁ | X | Y |
|---|---|---|---|---|---|---|---|---|---|---|
| S(O)CH₃ | H | S | CH₃ | H | CH₃ | CH₃ | CH₃ | H | CH₃ | OCH₃ |
| S(O)CH₃ | H | S | CH₃ | H | CH₃ | H | CH₃ | H | OCH₃ | OCH₃ |
| S(O)CH₃ | H | S | H | H | H | H | H | H | Cl[b] | OCH₃ |
| S(O)CH₃ | H | S | H | H | H | H | H | H | CH₃ | OCH₃ |
| S(O)₂CH₃ | H | S | H | H | H | H | H | H | OCH₃ | OCH₃ |
| S(O)₂CH₃ | H | S | CH₃ | CH₃ | H | H | CH₃ | CH₃ | CH₃ | OCH₃ |
| S(O)₂CH₃ | H | S | H | H | CH₃ | CH₃ | H | H | OCH₃ | OCH₃ |
| CF₃ | H | S | H | H | H | H | H | H | CH₃ | OCH₃ |
| CF₃ | H | S | CH₃ | H | H | H | H | H | OCH₃ | OCH₃ |
| CF₃ | H | S | H | H | CH₃ | H | H | H | Cl[b] | OCH₃ |
| CF₃ | H | S | H | H | H | H | CH₃ | H | CH₃ | OCH₃ |
| N(CH₃)₂ | H | S | H | H | H | H | H | H | CH₃ | OCH₃ |
| N(CH₃)₂ | H | S | H | H | H | H | H | H | OCH₃ | OCH₃ |
| N(CH₃)₂ | H | S | H | H | H | H | H | H | Cl[b] | OCH₃ |
| N(CH₃)₂ | H | S | CH₃ | H | H | H | H | CH₃ | OCH₃ | OCH₃ |
| N(CH₃)CH₂CH₃ | H | S | H | H | H | H | H | H | OCH₃ | OCH₃ |
| N(CH₂CH₃)₂ | H | S | H | H | H | H | H | H | OCH₃ | OCH₃ |
| CO₂CH₃ | H | S | H | H | H | H | H | H | CH₃ | OCH₃ |
| CO₂CH₃ | H | S | H | H | CH₃ | H | H | H | OCH₃ | OCH₃ |
| CO₂CH₃ | H | S | H | H | CH₃ | CH₃ | H | H | CH₃ | CH₃ |
| CO₂CH₂CH₂Cl | H | S | H | H | H | H | H | H | CH₃ | OCH₃ |
| SO₂N(CH₃)₂ | H | S | H | H | H | H | H | H | OCH₃ | OCH₃ |
| SO₂N(CH₃)₂ | H | S | H | H | H | H | H | H | CH₃ | OCH₃ |
| C₆H₅ | H | S | H | H | H | H | H | H | CH₃ | CH₃ |
| C₆H₅ | H | S | H | H | H | H | H | H | CH₃ | OCH₃ |
| C₆H₅ | H | S | H | H | H | H | H | H | OCH₃ | OCH₃ |
| C₆H₅ | H | S | CH₃ | H | CH₃ | H | CH₃ | H | CH₃ | OCH₃ |
| C₆H₅ | H | S | CH₃ | H | H | H | CH₃ | H | OCH₃ | OCH₃ |
| 2'-C₆H₄Cl | H | S | H | H | H | H | H | H | CH₃ | OCH₃ |
| 2'-C₆H₄Br | H | S | CH₃ | H | CH₃ | H | H | H | OCH₃ | OCH₃ |
| 2'-C₆H₄F | H | S | H | H | H | H | H | CH₃ | CH₃ | OCH₃ |
| 3'-C₆H₄CH₃ | H | S | H | H | H | H | H | H | OCH₃ | OCH₃ |
| 4'-C₆H₄OCH₃ | H | S | H | H | H | H | H | H | OCF₂H | OCH₃ |
| CH₂CO₂CH₃ | H | S | H | H | H | H | H | H | CH₃ | OCH₃ |
| CH₂CO₂CH₃ | H | S | H | H | CH₃ | CH₃ | H | H | OCH₃ | OCH₃ |
| CH₂CO₂CH₃ | H | S | H | H | H | H | H | H | Cl[b] | OCH₃ |
| CHCO₂CH₃<br>\|<br>CH₃ | H | S | H | H | H | H | H | H | OCF₂H | OCH₃ |
| OSO₂CH₃ | H | S | H | H | H | H | H | H | CH₃ | OCH₃ |
| OSO₂CH₃ | H | S | H | H | H | H | H | H | OCH₃ | OCH₃ |
| OSO₂CH₃ | H | S | H | H | H | H | H | H | Cl[b] | OCH₃ |
| OSO₂CH₃ | H | S | H | H | H | H | H | H | OCF₂H | OCH₃ |
| OSO₂CF₃ | H | S | H | H | H | H | H | CH₃ | CH₃ | OCH₃ |
| CH₂OCH₃ | H | S | H | H | H | H | H | H | CH₃ | OCH₃ |
| CH₂OCH₃ | H | S | H | H | H | H | H | H | CH₃ | CH₃ |
| CH₂OCH₃ | H | S | H | H | CH₃ | H | H | H | OCF₂H | OCH₃ |
| CH₂OCH₃ | H | S | H | H | CH₃ | H | CH₃ | H | CH₃ | CH₃ |
| CH₂OCF₂H | H | S | H | H | H | H | H | H | CH₃ | OCH₃ |
| CH₂OCF₂H | H | S | H | H | H | H | H | H | OCH₃ | OCH₃ |
| CH₂OCF₂H | H | S | CH₃ | H | H | H | CH₃ | H | Cl[b] | OCH₃ |
| CH₂OCF₂H | H | S | CH₃ | CH₃ | CH₃ | H | CH₃ | H | CH₃ | OCH₃ |

TABLE 15

(a) Z = N
(b) Z = CH

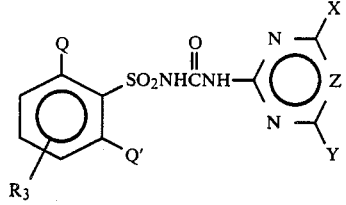

In the following table, $R_{15}$–$R_{31}$ are H.

| Q | Q' | $R_3$ | X | Y |
|---|---|---|---|---|
| Q-1 | Q-1 | H | CH₃ | CH₃ |
| Q-1 | Q-2 | H | CH₃ | OCH₃ |
| Q-1 | Q-3 | H | OCH₃ | OCH₃ |
| Q-1 | Q-4 | H | Cl[b] | OCH₃ |
| Q-1 | Q-5 | H | OCF₂H | OCH₃ |
| Q-1 | Q-6 | H | CH₃ | CH₃ |
| Q-1 | Q-7 | H | CH₃ | OCH₃ |
| Q-1 | Q-8 | H | OCH₃ | OCH₃ |
| Q-1 | Q-9 | H | Cl[b] | OCH₃ |
| Q-1 | Q-10 | H | OCF₂H | OCH₃ |
| Q-1 | Q-11 | H | CH₃ | CH₃ |
| Q-1 | Q-12 | H | CH₃ | OCH₃ |
| Q-1 | Q-13 | H | OCH₃ | OCH₃ |
| Q-1 | Q-14 | H | Cl[b] | OCH₃ |
| Q-1 | Q-15 | H | OCF₂H | OCH₃ |
| Q-1 | Q-16 | H | CH₃ | CH₃ |
| Q-1 | Q-17 | H | CH₃ | OCH₃ |
| Q-1 | Q-18 | H | OCH₃ | OCH₃ |
| Q-1 | Q-19 | H | Cl[b] | OCH₃ |
| Q-1 | Q-20 | H | OCF₂H | OCH₃ |
| Q-2 | Q-2 | H | CH₃ | CH₃ |
| Q-2 | Q-3 | H | CH₃ | OCH₃ |
| Q-2 | Q-4 | H | OCH₃ | OCH₃ |
| Q-2 | Q-5 | H | Cl[b] | OCH₃ |
| Q-2 | Q-6 | H | OCF₂H | OCH₃ |
| Q-2 | Q-7 | H | CH₃ | CH₃ |
| Q-2 | Q-8 | H | CH₃ | OCH₃ |
| Q-2 | Q-9 | H | OCH₃ | OCH₃ |
| Q-2 | Q-10 | H | Cl[b] | OCH₃ |
| Q-2 | Q-11 | H | OCF₂H | OCH₃ |
| Q-2 | Q-12 | H | CH₃ | CH₃ |
| Q-2 | Q-13 | H | CH₃ | OCH₃ |
| Q-2 | Q-14 | H | OCH₃ | OCH₃ |
| Q-2 | Q-15 | H | Cl[b] | OCH₃ |
| Q-2 | Q-16 | H | OCF₂H | OCH₃ |
| Q-2 | Q-17 | H | CH₃ | CH₃ |
| Q-2 | Q-18 | H | CH₃ | OCH₃ |
| Q-2 | Q-19 | H | OCH₃ | OCH₃ |
| Q-2 | Q-20 | H | Cl[b] | OCH₃ |
| Q-3 | Q-3 | H | OCF₂H | OCH₃ |
| Q-3 | Q-4 | H | CH₃ | CH₃ |
| Q-3 | Q-5 | H | CH₃ | OCH₃ |
| Q-3 | Q-6 | H | OCH₃ | OCH₃ |
| Q-3 | Q-7 | H | Cl[b] | OCH₃ |
| Q-3 | Q-8 | H | OCF₂H | OCH₃ |
| Q-3 | Q-9 | H | CH₃ | CH₃ |
| Q-3 | Q-10 | H | CH₃ | OCH₃ |
| Q-3 | Q-11 | H | OCH₃ | OCH₃ |
| Q-3 | Q-12 | H | Cl[b] | OCH₃ |
| Q-3 | Q-13 | H | OCF₂H | OCH₃ |
| Q-3 | Q-14 | H | CH₃ | CH₃ |
| Q-3 | Q-15 | H | CH₃ | OCH₃ |
| Q-3 | Q-16 | H | OCH₃ | OCH₃ |
| Q-3 | Q-17 | H | Cl[b] | OCH₃ |
| Q-3 | Q-18 | H | OCF₂H | OCH₃ |
| Q-3 | Q-19 | H | CH₃ | CH₃ |
| Q-3 | Q-20 | H | CH₃ | OCH₃ |
| Q-4 | Q-4 | H | OCH₃ | OCH₃ |
| Q-4 | Q-5 | H | Cl[b] | OCH₃ |
| Q-4 | Q-6 | H | OCF₂H | OCH₃ |
| Q-4 | Q-7 | H | CH₃ | CH₃ |
| Q-4 | Q-8 | H | CH₃ | OCH₃ |
| Q-4 | Q-9 | H | OCH₃ | OCH₃ |
| Q-4 | Q-10 | H | Cl[b] | OCH₃ |
| Q-4 | Q-11 | H | OCF₂H | OCH₃ |
| Q-4 | Q-12 | H | CH₃ | CH₃ |
| Q-4 | Q-13 | H | CH₃ | OCH₃ |
| Q-4 | Q-14 | H | OCH₃ | OCH₃ |
| Q-4 | Q-15 | H | Cl[b] | OCH₃ |
| Q-4 | Q-16 | H | OCF₂H | OCH₃ |
| Q-4 | Q-17 | H | CH₃ | CH₃ |
| Q-4 | Q-18 | H | CH₃ | OCH₃ |
| Q-4 | Q-19 | H | OCH₃ | OCH₃ |
| Q-4 | Q-20 | H | Cl[b] | OCH₃ |
| Q-5 | Q-5 | H | CH₃ | CH₃ |
| Q-5 | Q-6 | H | CH₃ | OCH₃ |
| Q-5 | Q-7 | H | OCH₃ | OCH₃ |
| Q-5 | Q-8 | H | Cl[b] | OCH₃ |
| Q-5 | Q-9 | H | OCF₂H | OCH₃ |
| Q-5 | Q-10 | H | CH₃ | CH₃ |
| Q-5 | Q-11 | H | CH₃ | OCH₃ |
| Q-5 | Q-12 | H | CH₃ | OCH₃ |
| Q-5 | Q-13 | H | OCH₃ | OCH₃ |
| Q-5 | Q-14 | H | Cl[b] | OCH₃ |
| Q-5 | Q-15 | H | OCF₂H | OCH₃ |
| Q-5 | Q-16 | H | CH₃ | CH₃ |
| Q-5 | Q-17 | H | CH₃ | OCH₃ |
| Q-5 | Q-18 | H | OCH₃ | OCH₃ |
| Q-5 | Q-19 | H | Cl[b] | OCH₃ |
| Q-5 | Q-20 | H | OCF₂H | OCH₃ |
| Q-6 | Q-6 | H | CH₃ | CH₃ |
| Q-6 | Q-7 | H | CH₃ | OCH₃ |
| Q-6 | Q-8 | H | OCH₃ | OCH₃ |
| Q-6 | Q-9 | H | Cl[b] | OCH₃ |
| Q-6 | Q-10 | H | OCF₂H | OCH₃ |
| Q-6 | Q-11 | H | CH₃ | CH₃ |
| Q-6 | Q-12 | H | CH₃ | OCH₃ |
| Q-6 | Q-13 | H | OCH₃ | OCH₃ |
| Q-6 | Q-14 | H | Cl[b] | OCH₃ |
| Q-6 | Q-15 | H | OCF₂H | OCH₃ |
| Q-6 | Q-16 | H | CH₃ | CH₃ |
| Q-6 | Q-17 | H | CH₃ | OCH₃ |
| Q-6 | Q-18 | H | OCH₃ | OCH₃ |
| Q-6 | Q-19 | H | Cl[b] | OCH₃ |
| Q-6 | Q-20 | H | OCF₂H | OCH₃ |
| Q-7 | Q-7 | H | CH₃ | CH₃ |
| Q-7 | Q-8 | H | CH₃ | OCH₃ |
| Q-7 | Q-9 | H | OCH₃ | OCH₃ |
| Q-7 | Q-10 | H | Cl[b] | OCH₃ |
| Q-7 | Q-11 | H | OCF₂H | OCH₃ |
| Q-7 | Q-12 | H | CH₃ | CH₃ |
| Q-7 | Q-13 | H | CH₃ | OCH₃ |
| Q-7 | Q-14 | H | OCH₃ | OCH₃ |
| Q-7 | Q-15 | H | Cl[b] | OCH₃ |
| Q-7 | Q-16 | H | OCF₂H | OCH₃ |
| Q-7 | Q-17 | H | CH₃ | CH₃ |
| Q-7 | Q-18 | H | CH₃ | OCH₃ |
| Q-7 | Q-19 | H | OCH₃ | OCH₃ |
| Q-7 | Q-20 | H | Cl[b] | OCH₃ |
| Q-8 | Q-8 | H | CH₃ | CH₃ |
| Q-8 | Q-9 | H | CH₃ | OCH₃ |
| Q-8 | Q-10 | H | OCH₃ | OCH₃ |
| Q-8 | Q-11 | H | Cl[b] | OCH₃ |
| Q-8 | Q-12 | H | OCF₂H | OCH₃ |
| Q-8 | Q-13 | H | CH₃ | CH₃ |
| Q-8 | Q-14 | H | CH₃ | OCH₃ |
| Q-8 | Q-15 | H | OCH₃ | OCH₃ |
| Q-8 | Q-16 | H | Cl[b] | OCH₃ |
| Q-8 | Q-17 | H | OCF₂H | OCH₃ |
| Q-8 | Q-18 | H | CH₃ | CH₃ |
| Q-8 | Q-19 | H | CH₃ | OCH₃ |
| Q-8 | Q-20 | H | OCH₃ | OCH₃ |
| Q-9 | Q-9 | H | Cl[b] | OCH₃ |
| Q-9 | Q-10 | H | OCF₂H | OCH₃ |
| Q-9 | Q-11 | H | CH₃ | CH₃ |
| Q-9 | Q-12 | H | CH₃ | OCH₃ |
| Q-9 | Q-13 | H | OCH₃ | OCH₃ |
| Q-9 | Q-14 | H | Cl[b] | OCH₃ |

TABLE 15-continued (a) Z = N
(b) Z = CH

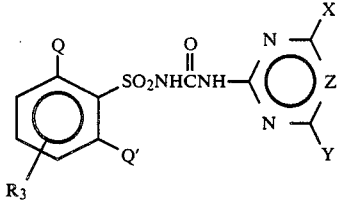

In the following table, $R_{15}-R_{31}$ are H.

| Q | Q' | $R_3$ | X | Y |
|---|---|---|---|---|
| Q-9  | Q-15 | H | $CH_3$ | $CH_3$ |
| Q-9  | Q-16 | H | $CH_3$ | $OCH_3$ |
| Q-9  | Q-17 | H | $OCH_3$ | $OCH_3$ |
| Q-9  | Q-18 | H | $Cl^b$ | $OCH_3$ |
| Q-9  | Q-19 | H | $OCF_2H$ | $OCH_3$ |
| Q-9  | Q-20 | H | $CH_3$ | $CH_3$ |
| Q-10 | Q-10 | H | $CH_3$ | $OCH_3$ |
| Q-10 | Q-11 | H | $OCH_3$ | $OCH_3$ |
| Q-10 | Q-12 | H | $Cl^b$ | $OCH_3$ |
| Q-10 | Q-13 | H | $OCF_2H$ | $OCH_3$ |
| Q-10 | Q-14 | H | $CH_3$ | $CH_3$ |
| Q-10 | Q-15 | H | $CH_3$ | $OCH_3$ |
| Q-10 | Q-16 | H | $OCH_3$ | $OCH_3$ |
| Q-10 | Q-17 | H | $Cl^b$ | $OCH_3$ |
| Q-10 | Q-18 | H | $OCF_2H$ | $OCH_3$ |
| Q-10 | Q-19 | H | $CH_3$ | $CH_3$ |
| Q-10 | Q-20 | H | $CH_3$ | $OCH_3$ |
| Q-11 | Q-11 | H | $OCH_3$ | $OCH_3$ |
| Q-11 | Q-12 | H | $Cl^b$ | $OCH_3$ |
| Q-11 | Q-13 | H | $OCF_2H$ | $OCH_3$ |
| Q-11 | Q-14 | H | $CH_3$ | $CH_3$ |
| Q-11 | Q-15 | H | $CH_3$ | $OCH_3$ |
| Q-11 | Q-15 | H | $OCH_3$ | $OCH_3$ |
| Q-11 | Q-16 | H | $Cl^b$ | $OCH_3$ |
| Q-11 | Q-17 | H | $OCF_2H$ | $OCH_3$ |
| Q-11 | Q-18 | H | $CH_3$ | $CH_3$ |
| Q-11 | Q-19 | H | $CH_3$ | $OCH_3$ |
| Q-11 | Q-20 | H | $OCH_3$ | $OCH_3$ |
| Q-12 | Q-12 | H | $Cl^b$ | $OCH_3$ |
| Q-12 | Q-13 | H | $OCF_2H$ | $OCH_3$ |
| Q-12 | Q-14 | H | $CH_3$ | $CH_3$ |
| Q-12 | Q-15 | H | $CH_3$ | $OCH_3$ |
| Q-12 | Q-16 | H | $OCH_3$ | $OCH_3$ |
| Q-12 | Q-17 | H | $Cl^b$ | $OCH_3$ |
| Q-12 | Q-18 | H | $OCF_2H$ | $OCH_3$ |
| Q-12 | Q-19 | H | $CH_3$ | $CH_3$ |
| Q-12 | Q-20 | H | $CH_3$ | $OCH_3$ |
| Q-13 | Q-13 | H | $OCH_3$ | $OCH_3$ |
| Q-13 | Q-14 | H | $Cl^b$ | $OCH_3$ |
| Q-13 | Q-15 | H | $OCF_2H$ | $OCH_3$ |
| Q-13 | Q-16 | H | $CH_3$ | $CH_3$ |
| Q-13 | Q-17 | H | $CH_3$ | $OCH_3$ |
| Q-13 | Q-18 | H | $OCH_3$ | $OCH_3$ |
| Q-13 | Q-19 | H | $Cl^b$ | $OCH_3$ |
| Q-13 | Q-20 | H | $OCF_2H$ | $OCH_3$ |
| Q-14 | Q-14 | H | $CH_3$ | $CH_3$ |
| Q-14 | Q-15 | H | $CH_3$ | $OCH_3$ |
| Q-14 | Q-16 | H | $OCH_3$ | $OCH_3$ |
| Q-14 | Q-17 | H | $Cl^b$ | $OCH_3$ |
| Q-14 | Q-18 | H | $OCF_2H$ | $OCH_3$ |
| Q-14 | Q-19 | H | $CH_3$ | $CH_3$ |
| Q-14 | Q-20 | H | $CH_3$ | $OCH_3$ |
| Q-15 | Q-15 | H | $CH_3$ | $OCH_3$ |
| Q-15 | Q-16 | H | $OCH_3$ | $OCH_3$ |
| Q-15 | Q-17 | H | $Cl^b$ | $OCH_3$ |
| Q-15 | Q-18 | H | $OCF_2H$ | $OCH_3$ |
| Q-15 | Q-19 | H | $CH_3$ | $CH_3$ |
| Q-15 | Q-20 | H | $CH_3$ | $OCH_3$ |
| Q-16 | Q-16 | H | $OCH_3$ | $OCH_3$ |
| Q-16 | Q-17 | H | $Cl^b$ | $OCH_3$ |
| Q-16 | Q-18 | H | $OCF_2H$ | $OCH_3$ |
| Q-16 | Q-19 | H | $CH_3$ | $CH_3$ |
| Q-16 | Q-20 | H | $CH_3$ | $OCH_3$ |
| Q-17 | Q-17 | H | $OCH_3$ | $OCH_3$ |
| Q-17 | Q-18 | H | $Cl^b$ | $OCH_3$ |
| Q-17 | Q-19 | H | $OCF_2H$ | $OCH_3$ |
| Q-17 | Q-20 | H | $CH_3$ | $CH_3$ |
| Q-18 | Q-18 | H | $CH_3$ | $OCH_3$ |
| Q-18 | Q-19 | H | $OCH_3$ | $OCH_3$ |

TABLE 15-continued (a) Z = N
(b) Z = CH

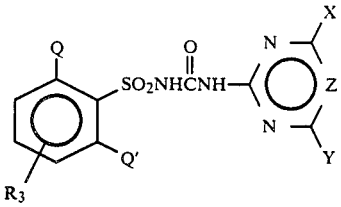

In the following table, $R_{15}-R_{31}$ are H.

| Q | Q' | $R_3$ | X | Y |
|---|---|---|---|---|
| Q-18 | Q-20 | H | $Cl^b$ | $OCH_3$ |
| Q-19 | Q-19 | H | $CH_3$ | $CH_3$ |
| Q-19 | Q-20 | H | $CH_3$ | $OCH_3$ |
| Q-20 | Q-20 | H | $OCH_3$ | $OCH_3$ |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE 16

| | Active Ingredient | Weight Percent* | |
|---|---|---|---|
| | | Diluent(s) | Surfactant(s) |
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering,* Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 10

Wettable Powder

| | |
|---|---|
| N—[(4,6-dimethoxypyrimidin-2-yl)aminocarbonyl]-3-methylsulfonyl-1,1'-biphenyl-2-sulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 11

Wettable Powder

| | |
|---|---|
| N—[(4,6-dimethoxy-1,3,5-triazin-2-yl)aminocarbonyl]-2,6-bis(methylthio)benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 12

Granule

| | |
|---|---|
| Wettable Powder of Example 11 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

EXAMPLE 13

Extruded Pellet

| | |
|---|---|
| N—[(4,6-dimethoxypyrimidin-2-yl)aminocarbonyl]-3-methylsulfonyl-1,1'-biphenyl-2-sulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 14

Low Strength Granule

| | |
|---|---|
| N—[(4,6-dimethoxy-1,3,5-triazin-2-yl)aminocarbonyl]-2,6-bis(methylthio)benzenesulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 15

Aqueous Suspension

| | |
|---|---|
| N—[(4,6-dimethoxy-1,3,5-triazin-2-yl)aminocarbonyl]-2,6-bis(methylthio)benzenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 16

Solution

| | |
|---|---|
| N—[(4,6-dimethoxypyrimidin-2-yl)aminocarbonyl]-3-methylsulfonyl-1,1'-biphenyl-2-sulfonamide, sodium salt | 5% |

| | |
|---|---|
| water | 95% |

The salt is added directly to the water with stirring to produce the solution, which may then be packaged for use.

EXAMPLE 17

Low Strength Granule

| | |
|---|---|
| N—[(4,6-dimethoxy-1,3,5-triazin-2-yl)aminocarbonyl]-2,6-bis(methylthio)benzenesulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 18

Granule

| | |
|---|---|
| N—[(4,6-dimethoxypyrimidin-2-yl)aminocarbonyl]-3-methylsulfonyl-1,1'-biphenyl-2-sulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 19

High Strength Concentrate

| | |
|---|---|
| N—[(4,6-dimethoxy-1,3,5-triazin-2-yl)aminocarbonyl]-2,6-bis(methylthio)benzenesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 20

Wettable Powder

| | |
|---|---|
| N—[(4,6-dimethoxypyrimidin-2-yl)aminocarbonyl]-3-methylsulfonyl-1,1'-biphenyl-2-sulfonamide | 90% |
| dioctyl sodium sulfosuccinate | 0.1% |

| | |
|---|---|
| synthetic fine silica | 9.9% |

The ingredients are blended and ground in a hammer-mill to produce particles essentially all below 100 microns. The material is sifted through a U.S.S. No. 50 screen and then packaged.

EXAMPLE 21

Wettable Powder

| | |
|---|---|
| N—[(4,6-dimethoxy-1,3,5-triazin-2-yl)aminocarbonyl]-2,6-bis(methylthio)benzenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 22

Oil Suspension

| | |
|---|---|
| N—[(4,6-dimethoxy-1,3,5-triazin-2-yl)aminocarbonyl]-2,6-bis(methylthio)benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 23

Dust

| | |
|---|---|
| N—[(4,6-dimethoxypyrimidin-2-yl)aminocarbonyl]-3-methylsulfonyl-1,1'-biphenyl-2-sulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

Utility

Test results indicate that the compounds of the present invention are active herbicides. They should have utility for broad-spectrum pre and/or postemergence weed control in areas where complete control of all vegetation is desired, such as around fuel storage tanks, ammunition depots, industrial storage areas, parking lots, drive-in theaters, around billboards, highway and railroad structures. Alternatively, many of the subject compounds should be useful for the selective pre or postemergence weed control in crops, especially wheat and sugar beets.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.005 to 10 kg/ha, the lower rates being suggested for use on lighter soils and/or those having a low organic matter content, or for situations where only short-term persistence is required.

The compounds of the invention may be used in combination with any other commercial herbicide, examples of which are those of the triazine, triazole, uracil, urea, amide, diphenylether, carbamate and bipyridylium types.

The herbicidal properties of the subject compounds were discovered in a number of greenhouse tests. The test procedures and results follow.

Test A

Seeds of crabgrass (Digitaria sp.), barnyardgrass (Echinochloa crusgalli), wild oats (Avena fatua), sicklepod (Cassia obtusifolia), morningglory (Ipomoes sp.), cocklebur (Xanthium sp.), sorghum, corn, soybean, sugar beet, rice, wheat and purple nutsedge (Cyperus rotundus) tubers were planted and treated preemergence with the test chemicals dissolved in a non-phytotoxic solvent. At the same time, these crop and weed species, along with cotton and bush bean, were treated with a soil/foilage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
E=emergence inhibition;
G=growth retardation;
H=formative effects;
U=unusual pigmentation; and
6Y=abscised buds or flowers.

COMPOUNDS

| | Compounds | | |
|---|---|---|---|
| Compound 1 | 2-$SO_2CH_3$, 6-$C_6H_5$-phenyl-$SO_2NH$-CO-$NH$-[4,6-di-$CH_3$-pyrimidin-2-yl] | | m.p. 228–230° C. (d) |
| Compound 2 | 2-$SO_2CH_3$, 6-$C_6H_5$-phenyl-$SO_2NH$-CO-$NH$-[4-$CH_3$-6-$OCH_3$-pyrimidin-2-yl] | | m.p. 206–208° C. |
| Compound 3 | 2-$SO_2CH_3$, 6-$C_6H_5$-phenyl-$SO_2NH$-CO-$NH$-[4,6-di-$OCH_3$-pyrimidin-2-yl] | | m.p. 212–214° C. |
| Compound 4 | 2,6-di-$SCH_3$-phenyl-$SO_2NH$-CO-$NH$-[4,6-di-$OCH_3$-pyrimidin-2-yl] | | m.p. 220–225° C. |
| Compound 5 | 2,6-di-$SCH_3$-phenyl-$SO_2NH$-CO-$NH$-[4-$CH_3$-6-$OCH_3$-pyrimidin-2-yl] | | m.p. 206–208° C. |
| Compound 6 | 2,6-di-$SCH_3$-phenyl-$SO_2NH$-CO-$NH$-[4,6-di-$CH_3$-pyrimidin-2-yl] | | m.p. 188–194° C. |

-continued
Compounds
Compound 7 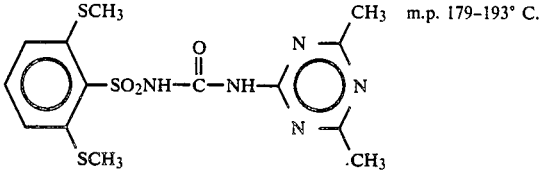 m.p. 179–193° C.
Compound 8 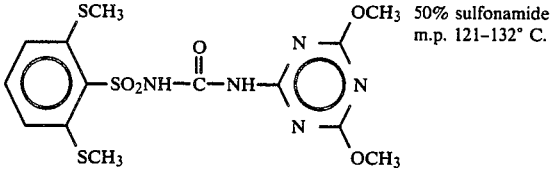 50% sulfonamide
m.p. 121–132° C.
Compound 9 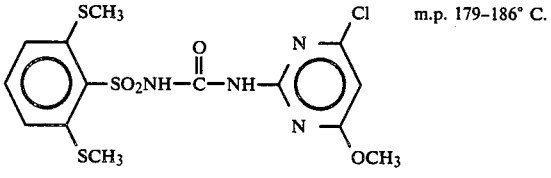 m.p. 179–186° C.
Compound 10 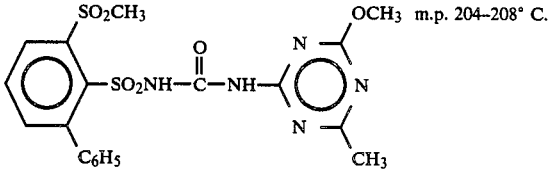 m.p. 204–208° C. (d)
Compound 11 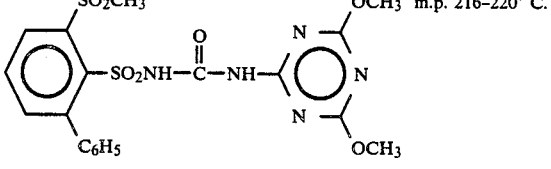 m.p. 216–220° C. (d)
Compound 12 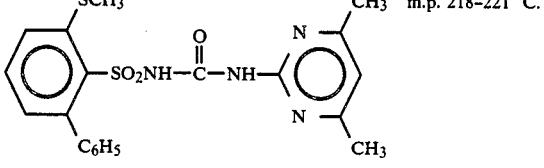 m.p. 218–221° C. (d)
Compound 13 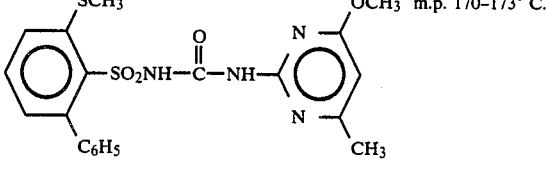 m.p. 170–173° C.
Compound 14 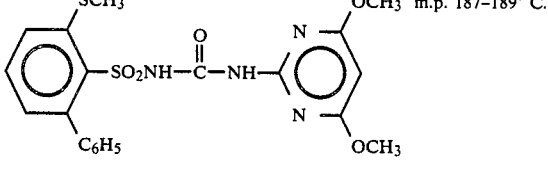 m.p. 187–189° C.

-continued

Compounds

Compound 15: 2-SCH₃, 6-C₆H₅ phenyl-SO₂NH-C(=O)-NH- [pyrimidine with OCH₃, CH₃] m.p. 130-135° C. (d)

TABLE A

| | Cmpd. 1 | Compound 2 | | Cmpd. 3 | Cmpd. 4 | Cmpd. 5 | Cmpd. 6 | Cmpd. 7 |
|---|---|---|---|---|---|---|---|---|
| Rate g/ha | 50 | 50 | 400 | 50 | 50 | 50 | 50 | 50 |
| POSTEMERGENCE | | | | | | | | |
| Bush bean | 3C,3H | 5C,9G,6Y | 6C,9G,6Y | 4C,8H,6Y | 4C,9G,6Y | 2C,7G,6Y | 4C,8H,6Y | 3C,8G,6Y |
| Cotton | 4C,8G | 4C,9G | 4C,9G | 4C,9G | 5C,9G | 4C,9G | 5C,9H | 2C,2H,5G |
| Morningglory | 9C | 4C,9G | 5C,9G | 5C,9G | 5C,9G | 4C,9G | 4C,7G | 2C |
| Cocklebur | 9C | 9C | 9C | 5C,9G | 9C | 9C | 9C | 3C,8H |
| Sicklepod | 4C,3H | 2C,2H | 2C,6G | 4C,9G | 9C | 5C,9G | 5C,9G | 2C,5G |
| Nutsedge | 4C,9G | 8G | 4C,9G | 4C,9G | 9C | 2C,9G | 5C,9G | 1C,5G |
| Crabgrass | 4G | 2C,5G | 2C,8G | 2C,5G | 2C,9G | 2C,8G | 2C,8G | 5G |
| Barnyardgrass | 4C,9H | 2C,7H | 5C,9G | 3C,9H | 9C | 9C | 9C | 3C,9H |
| Wild Oats | 3C,5G | 2C,4G | 4C,9G | 2C | 9C | 9C | 5C,9G | 5G,2C |
| Wheat | 5G | 3G | 9G | 3G | 9C | 10C | 9C | 1C,3G |
| Corn | 2C,6H | 2C,9H | 1U,9G | 2C,8H | 9C | 3U,9G | 2C,9H | 2C,9H |
| Soybean | 5C,9G | 5C,9G | 5C,9G | 5C,9G | 4C,9G | 5C,9G | 5C,9G | 3C,7G |
| Rice | 2C,7G | 2C,4G | 2C,8G | 1C,1H | 5C,9G | 5C,9G | 5C,9G | 4C,9G |
| Sorghum | 3C,8H | 3C,9G | 5C,9G | 2C,9G | 5U,9G | 5C,9G | 4C,9G | 3C,9G |
| Sugar beet | 2C,8G | 2C | 4C,8G | 2C,8G | 9C | 9C | 9C | 2C,8G |
| PREEMERGENCE | | | | | | | | |
| Morningglory | 2C,9G | 2C,8H | 9C | 4C,9G | 9C | 9C | 9G | 8G |
| Cocklebur | 9H | 9H | 9H | 9H | 9H | 9H | 9H | — |
| Sicklepod | 3C,6G | 2C,2G | 2C,9G | 4C,5H | 9C | 4C,9G | 9G | 9G |
| Nutsedge | 2C,6G | 5G | 10E | 4C,6G | 10E | 10E | 10E | 0 |
| Crabgrass | 2G | 2G | 7G | 2G | 4C,9G | 3C,5G | 1C | 2G |
| Barnyardgrass | 5C,6G | 3C,7G | 5C,9H | 5C,6G | 5C,9H | 5C,9H | 5C,9H | 2C,8H |
| Wild Oats | 2C,8G | 3C,8G | 5C,9H | 3C | 5C,9G | 5C,9H | 5C,9G | 2C,8G |
| Wheat | 8G | 2C,8G | 3C,9H | 1C,4G | 10C | 10H | 4C,9H | 7G |
| Corn | 2C,8H | 2C,9H | 4C,9H | 9G | 10E | 9H | 3C,9H | 2C,8G |
| Soybean | 4C,5G | 4C,6H | 9H | 5C,6H | 9H | 8H | 9H | 1C,3G |
| Rice | 4C,6G | 4C,6G | 4C,9H | 3C,3G | 10E | 10E | 10E | 2C,9H |
| Sorghum | 4C,9H | 3C,9H | 10H | 5C,9G | 5C,9H | 10H | 5C,9H | 5C,9H |
| Sugar beet | 3C,9G | 2C,9G | 9G | 8G | 10C | 9C | 5C,9G | 5C,9G |

| | Cmpd. 8 | Cmpd. 9 | Cmpd. 10 | Cmpd. 11 | Cmpd. 12 | Cmpd. 13 | Cmpd. 14 | Cmpd. 15 |
|---|---|---|---|---|---|---|---|---|
| Rate g/ha | 50 | 50 | 50 | 50 | 50 | 50 | 50 | 50 |
| POSTEMERGENCE | | | | | | | | |
| Bush bean | 5C,9G,6Y | 2H | | | | | | |
| Cotton | 4C,9G | 2C | 5C,9G | 5C,9G | 2C,8H | 2C,8G | 2C,8G | 2C,8G |
| Morningglory | 2C,4G | 1C | 10C | 10C | 3C,9G | 3C,8G | 2C,5G | 4C,9G |
| Cocklebur | 3C,9H | 2C,5G | 9C | 9C | 5C,9G | 3C,9G | 2C,7H | 5C,9G |
| Sicklepod | 4C,9G | 5G | 4C,8G | 4C,7G | 3C | 2C | 2C,3G | 3C,6H |
| Nutsedge | 4G | 2G | 6C,9G | 4C,9G | 2C,8G | 3C,9G | 10C | 3C,9G |
| Crabgrass | 2C,5G | 5G | 5C,8G | 0 | 2G | 0 | 3H | 0 |
| Barnyardgrass | 2C,8H | 2C,3G | 10C | 9C | 3C,8H | 3C,8H | 2C,8H | 9C |
| Wild Oats | 2C,8H | 0 | 9C | 9C | 5G | 0 | 0 | 9C |
| Wheat | 6C,9G | 0 | 9C | 3C,9G | 0 | 2G | 0 | 9C |
| Corn | 4C,9H | 2C,3G | 3C,9G | 2U,9G | 0 | 0 | 1H | 3H |
| Soybean | 3C,9G | 2C,5G | 3C,9G | 4C,9G | 2C,9G | 2C,9G | 2C,9G | 3C,9G |
| Rice | 5C,9G | 2C | 3G | 4C,9G | 5G | 4G | 5G | 2C,9G |
| Sorghum | 2C,9G | 9H | 10C | 9C | 2C,8G | 2C,9G | 2C,8H | 3C,9G |
| Sugar beet | 3C,9G | 2C,8G | 10C | 10C | 5G | 5G | 3G | 3C,9G |
| PREEMERGENCE | | | | | | | | |
| Morningglory | 8G | 7G | 9G | 9H | 2C,7H | 9C | 9G | 9C |
| Cocklebur | 9H | 8H | 9H | 9H | 9H | 9H | 9H | 9H |
| Sicklepod | 7G | 6G | 5C,8G | 6G,5C | 2C,7G | 8G | 7G | 3C,7G |
| Nutsedge | 10E | 10E | 2C,5G | 0 | 5G | 2C,9G | 5G | 0 |
| Crabgrass | 0 | 2G | 1C | 0 | 0 | 0 | 0 | 0 |
| Barnyardgrass | 2C,5G | 2C,7G | 1C | 2C | 2C,6H | 3C,8H | 2C,7G | 4G |
| Wild Oats | 2C,7G | 2C,7G | 3C,9G | 5C,9G | 2C,9G | 2C,8G | 2C | 2C,8G |
| Wheat | 2C,7G | 9G | 2C,4G | 8G | 2G | 2C,7G | 3G | 3G |
| Corn | 2C,7G | 2C,5G | 3C,9G | 9G | 5G | 2C,8G | 2C,7H | 2C,9H |
| Soybean | 1C,1H | 1C,1H | 3C,7H | 3C,8H | 2C,3H | 3C,7H | 1C,1H | 3C,5H |
| Rice | 3C,9H | 3C,9H | 3C,4G | 5G | 2C,6G | 2C,6G | 3C,6G | 7G |
| Sorghum | 2C,9H | 5C,9H | 5C,9H | 6C,9H | 2C,9H | 2C,9H | 3C,7H | 2C,9G |
| Sugar beet | 3C,9G | 3C,9G | 9C | 10C | 8G | 2C,9G | 7G | 9G |

To better define the utility of the compounds of this invention, several of the compounds were tested in wheat. The data for several of the compounds tested are summarized in Table B.

TABLE B

| | PREEMERGENCE ON WOODSTOWN SANDY LOAM | | | | | | | | | |
|---|---|---|---|---|---|---|---|---|---|---|
| | Compound 1 | | Compound 2 | | Compound 5 | | Compound 7 | | | |
| Rate g/ha | 16 | 125 | 16 | 125 | 8 | 62 | 4 | 16 | 62 | 250 |
| Crabgrass | 0 | 0 | 0 | 2G | 2G | 7G | 0 | 0 | 0 | 0 |
| Barnyardgrass | 3G | 9G | 2G | 9G | 5G | 9G | 0 | 0 | 0 | 7G |
| Sorghum | 9G | 9G | 7G | 9G | 9G | 9G | — | — | — | — |
| Wild Oats | 2G | 8G | 2G | 7G | 6G | 9G | 0 | 0 | 0 | 5G |
| Johnsongrass | 3G | 9G | 5G | 9G | 8G | 9G | 0 | 0 | 0 | 7G |
| Dallisgrass | 0 | 6G | 3G | 3G | 3G | 8G | — | — | — | — |
| Giant foxtail | 3G | 4G | 4G | 3G | 3G | 8G | 0 | 0 | 0 | 2G |
| Ky. bluegrass | — | — | — | — | 3G | 9G | — | — | — | — |
| Cheatgrass | 6G | 8G | 7G | 9G | 9G | 10C | — | — | — | — |
| Sugar beets | 5G | 10C | 5G | 8G | 6G | 9G | 0 | 3G | 7G | 9G |
| Corn | 2G | 5G,3C | 3G | 9G | 3G,2C | 4G,2C | 0 | 0 | 4G | 8G |
| Rape | 9G | 10C | 9G | 9G | 5G | 9G | — | — | — | — |
| Cocklebur | 6G | 9G | 7G | 9G | 5G | 9G | 0 | 0 | 7G | 9G |
| Nutsedge | 7G | 10C | 4G | 10C | 3G | 8G | 0 | 0 | 3G | 8G |
| Cotton | 9G | 8G | 8G | 6G | 5G | 7G | 0 | 0 | 3G | 7G |
| Morningglory | 6G | 9G | 3G | 7G | 0 | 8G | 0 | 0 | 0 | 5G |
| Sicklepod | 5G | 7G | 2G | 6G | 0 | 8G | 0 | 0 | 4G | 9G |
| Teaweed | 5G | 8G | 2G | 6G | 3G | 8G | 0 | 0 | 3G | 7G |
| Velvetleaf | 5G | 8G | 0 | 8G | 5G | 8G | 0 | 0 | 2G | 9G |
| Jimsonweed | 3G | 9G | 0 | 8G | 7G | 9G | 0 | 0 | 3G | 2G |
| Soybean | 2G | 8G,7H | 0 | 6G,3H | 3G | 8G,7H | 0 | 0 | 2G | 7G |
| Rice | 8G | 9G | 7G | 3G | 8G | 10C | 0 | 3G | 8G | 10G |
| Wheat | 0 | 2G | 0 | 0 | 2G | 7G | 0 | 0 | 0 | 5G |

Tests B–F.

Test B

Two plastic bulb pans were filled with fertilized and limed Woodstown sandy loam soil. One pan was planted with corn, sorghum, Kentucky bluegrass and several grass weeds. The other pan was planted with cotton, soybeans, rapeseed, purple nutsedge (*Cyperus rotundus*), and several broadleaf weeds. The following grass and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), cocklebur (*Xanthium pensylvanicum*), morningglory (*Ipomoea hederacea*), sicklepod (*Cassia obtusifolia*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugar beets. The above four containers were treated preemergence with several test compounds within the scope of the invention.

Twenty-eight days after treatment, the plants were evaluated and visually rated for response to the chemical treatments utilizing the rating system described previously for Test A. Compounds 1–6 each exhibited a broad-spectrum of control at application rates as low as 16 g/ha; compounds 1, 2 and 3 were also safe on wheat at application rates as high as 125 g/ha. Compounds 7–9 showed some activity at 16 g/ha, but exhibited a broader spectrum of activity at rates of 62 g/ha and above. Compounds 7 and 8 also showed some safety on wheat. The data for several of the compounds tested are summarized in Table B.

Test C

The test chemicals, dissolved in a non-phytotoxic solvent, were applied in an overall spray to the foilage and surrounding soil of selected plant species. Approximately fourteen days after treatment, all species were visually compared to untreated controls and rated for response to treatment. The rating system was as described previously for Test A. The data are presented in Table C.

All plant species were seeded in Woodstown sandy loam soil and grown in a greenhouse. The following species were grown in soil contained in plastic pots (25 cm diameter by 13 cm deep): soybeans, cotton, alfalfa, corn, rice, wheat, sorghum, velvetleaf (*Abutilon theophrasti*), sesbania (*Sesbania exaltata*), Sicklepod (*Cassia obtusifolia*), morningglory (*Ipomoea hederacea*), jimsonweed (*Datura stramonium*), cocklebur (*Xanthium pensylvanicum*), crabgrass (Digitaria sp.), nutsedge (*Cyperus rotundus*), branyardgrass (*Echinochloa crusgalli*), giant foxtail (*Sertaria faberii*) and wild oats (*Avena fatua*). The following species were grown in soil in a paper cup (12 cm diameter by 13 cm deep): sunflower, sugar beets, and mustard. All plants were sprayed approximately 14 days after planting. Additional plant species such as johnsongrass and field bindweed are sometimes added to this standard test.

Compounds 1–5 were tested by this procedure, and each exhibited postemergence activity at application rates as low as 4 g/ha. Compounds 2 and 3 were safe on wheat, and Compound 3 was also safe on sugar beets. Data for these compounds are presented in Table C.

TABLE C

| | Over-the-Top Soil/Foliage Treatment | | | | | | | | | | | |
|---|---|---|---|---|---|---|---|---|---|---|---|---|
| | Cmpd. 1 | | Cmpd. 2 | | Cmpd. 3 | | Compound 4 | | | | Compound 5 | | |
| Rate g/ha | 4 | 16 | 4 | 16 | 4 | 16 | 1 | 4 | 16 | 62 | 4 | 16 | 62 |
| Soybeans | 7G | 8G | 3C | 8C | 8C | 9C | 8G | 10C | 10C | 10C | 7G | 10C | 10C |
| Velvetleaf | 3G | 6G | 5G | 7G | 4G | 6G | 2C | 6C | 7C,7G | 7C,8G | 5C,5G | 7C,7G | 6C,7G |
| Sesbania | 5G | 8G | 4G | 7G | 8G | 8G | — | 4G | 9G | 9C | 8G | 9G | 9G |
| Sicklepod | 0 | 5G | 0 | 0 | 2C | 6C | 2C | 0 | 9G | 9G | 4G | 8G | 9G |

TABLE C-continued

| | Over-the-Top Soil/Foliage Treatment | | | | | | | | | | | |
|---|---|---|---|---|---|---|---|---|---|---|---|---|
| | Cmpd. 1 | | Cmpd. 2 | | Cmpd. 3 | | Compound 4 | | | Compound 5 | | |
| Rate g/ha | 4 | 16 | 4 | 16 | 4 | 16 | 1 | 4 | 16 | 62 | 4 | 16 | 62 |
| Cotton | 0 | 5G | 5G | 6G | 4G | 5G | 5G | 4C | 9G | 10C | 7G | 9G | 10C |
| Morningglory | 7G | 9G | 6G | 8G | 2G | 8G | 5G | 8G | 8C,8G | 9G | 7G | 8G | 10C |
| Bush Bean | — | — | — | — | — | — | — | — | 7C,7G | 8C,8G | 4G,4C | 10C | 10C |
| Jimsonweed | 8G | 9G | 5G | 5G | 0 | — | 0 | 0 | 9G | 9G | 5G | 7G | 8G |
| Cocklebur | 3G | 8G | 6G | 8G | 7G | 7G | 2G | — | 8G | 9G | 8G | 8G | 9G |
| Sunflower | — | — | — | — | — | — | — | — | 9C | 10C | 5G | 8G | 10C |
| Mustard | — | — | — | — | — | — | — | — | 8G | 9G | 7G | 10C | 10C |
| Sugar beets | 6G | 6G | 2G | 6G | 0 | 0 | 3G | 7G | 9G | 10C | 8G | 10C | 10C |
| Corn | 0 | 2G | 2G | 4G | 0 | 4H | 3G | 5G | 7G | 7G | 1G | 6G | 6G,6C |
| Crabgrass | 0 | 0 | 0 | 0 | 0 | 0 | 0 | 0 | 8G | 8G | 0 | 1G | 3G |
| Rice | 0 | 0 | 0 | 0 | 2G | 0 | 1C | 5C | 7G | 7G | 2G | 7G,4C | 5C,7G |
| Nutsedge | 0 | 0 | 0 | 0 | 2C | 8G | 2G | 3G | 6G | 8C | 1G | 5G | 8G |
| Barnyardgrass | 0 | 7G | 2G | 0 | 4G | 5G | 2G | 9G | 8G | 9C | 7G | 8G | 8G,6C |
| Wheat | 0 | 3G | 0 | 0 | 0 | 0 | 0 | 5G | 6G | 8G | 4G | 4G | 5G |
| Giant foxtail | 0 | 2G | 0 | 0 | 0 | 0 | 0 | 4G | 7G | 9G | 2G | 5G | 8G |
| Wild Oats | 0 | 2G | 0 | 0 | 0 | 0 | 0 | 4G | 7G | 8G | 5G | 7G | 7G |
| Sorghum | — | — | — | — | — | — | 0 | 5G | 8G | 9C | 8G | 9G | 9G |
| Johnsongrass | 0 | 3G | 1G | 3G | 4G | 7G | 3G | 9C | 10C | 10C | 4G | 7G | 7C,8G |
| Field Bindweed | — | — | — | — | — | — | 0 | 6C | 3G | 5G | 1G | 0 | 0 |

Test D

Two plastic pans lined with polyethylene liners were filled with prepared Woodstown early loam soil. One pan was planted with seeds of wheat (*Triticum aestivum*), barley (*Hordeum vulgare*), wild oats (*Avena fatua*), cheatgrass (*Bromus secalinus*), blackgrass (*Alopecurus myosuroides*), annual bluegrass (*Poa annua*), green foxtail (*Setaria viridis*), Italian ryegrass (*Lolium multiflorum*) and rapeseed (*Brassica napus*). The other pan was planted with seeds of Russian thistle (*Salsola kali*), cleavers (*Galium aparine*), speedwell (*Veronica persica*), kochia (*Kochia scoparia*), shepherdspurse (*Capsella bursa-pastoris*), *Matricaria inodora*, black nightshade (*Solanum nigrum*), wild buckwheat (*Polygonum convolvulus*) and sugar beets (*Beta vulgaris*). The above two pans were treated preemergence. At the same time two pans in which the above plant species were growing were treated postemergence. Plant heights at the time of treatment ranged from 1-20 cm depending on plant species.

The compounds applied were diluted with a non-phytotoxic solvent and sprayed over-the-top of the pans. An untreated control and a solvent alone control were included for comparison. All treatments were maintained in the greenhouse for 19-22 days at which time the treatments were compared to the controls and the effects visually rated. The recorded data are presented in Table D. Each of the tested compounds provides control of certain weeds at rates of application which cause no, or minimum injury to sugar beets.

TABLE D

| | Compound 1 | | | | Compound 2 | | | | Compound 3 | | | |
|---|---|---|---|---|---|---|---|---|---|---|---|---|
| | Preemergence | | Postemergence | | Preemergence | | Postemergence | | Preemergence | | Postemergence | |
| Rate g/ha | 15 | 60 | 15 | 60 | 15 | 60 | 15 | 60 | 15 | 60 | 15 | 60 |
| wheat | 0 | 2G | 0 | 0 | 0 | 0 | 0 | 2G | 1G | 2G,1C | 0 | 0 |
| barley | 2G | 7G | 0 | 0 | 0 | 3G | 0 | 3G | 1G | 1C | 0 | 1G |
| wild oats | 3G | 6G | 0 | 1G | 0 | 4G | 0 | 3G | 1G,2C | 3G | 0 | 0 |
| cheatgrass | 3G | 6G | 0 | 1G | 1C | 1G,4C | 0 | 2G | 0 | 0 | 0 | 0 |
| blackgrass | 9G | 9G | 0 | 1G | 0 | 4G | 0 | 3G | 6G | 7G | 0 | 3G |
| annual bluegrass | 4G | 7G | 0 | 0 | 0 | 0 | 0 | 1G | 2G | 2G | 0 | 2G |
| green foxtail | 2G | 3G | 0 | 0 | 0 | 0 | 0 | 0 | 0 | 3G | 0 | 0 |
| Italian ryegrass | 2G | 3G | 0 | 0 | 0 | 0 | 0 | 2G | 2G | 5G | 0 | 0 |
| rapeseed | 7G | 8G | 3G | 8G | 1C | 10C | 10C | 8G,1C | 8G | 10C | 9G,9C | 10C |
| *Matricaria inodora* | 6G | 9G | 6G,2C | 8G,3C | 8G | 8G | 3G | 6G,4C | 9G | 9G | 5G,2C | 9G,7C |
| Galium aparine | 10C | 10C | 10C | 10C | 10C | 10C | — | 10C | — | 10C | — | 10C |
| Russian thistle | 4G | 10C | 0 | 0 | 0 | 0 | 0 | 1G | 0 | 0 | 5G | 7G |
| shepherdspurse | 4G | 10C | 7G | 9G | 8G | 10C | 7G | 9G | 10C | 10C | 10C | 10C |
| kochia | 0 | 0 | 0 | 0 | 0 | 6G | 0 | 4G | 2G | 2G | 0 | 1G |
| black nightshade | 2G | 8G,3C | 6G | 8G,7C | 7G | 9G,9C | 3G,2C | 8G,8C | 3G | 4G | 3G,4C | 7G,3C |
| speedwell | 0 | 6G | 2G | 8G | 6G | 8G,3C | 2C,4G | 8G,7C | 2G | 7G | 8G,7C | 9G,2C |
| wild buckwheat | 0 | 6G | 2G,1C | 8G,8C | 0 | 5G | 2C | 7G,4C | 5G | 6G | 9G,5C | 8G,3C |
| sugar beets | 0 | 0 | 0 | 0 | 0 | 6G | 0 | 0 | 0 | 2G,1C | 0 | 0 |

Test E

Compounds 2 and 3 were further evaluated for their utility as selective sugar beet herbicides in a test which differed from Test D only in the types of certain weed species. The compounds were applied both pre and postemergence to the species shown in Table E. The relative tolerance of sugar beets is again evident from the data presented in Table E.

TABLE E

| | Compound 2 | | | Compound 3 | |
|---|---|---|---|---|---|
| Rate g/ha | 4 | 15 | 60 | 30 | 125 |
| | PreEmergence | | | | |
| wheat | 0 | 1G | 2G | 0 | 2G |
| barley | 0 | 1G | 2G | 0 | 4G |
| wild oats | 0 | 1G | 2G | 0 | 0 |
| ryegrass | 0 | 2G | 1G | 0 | 2G |
| annual bluegrass | 0 | 0 | 4G | 0 | 3G |
| blackgrass | 0 | 0 | 5G | 0 | 1G |
| green foxtail | 0 | 0 | 0 | 0 | 0 |
| *Matricaria inodora* | 9G | 8G | 9G | 9G,7C | 9G,7C |
| Galium aparine | 0 | 4G,3C | 10C | 0 | 0 |
| kochia | 0 | 3G | 8G | 0 | 1C |

TABLE E-continued

|  | Compound 2 | | | Compound 3 | |
|---|---|---|---|---|---|
| Rate g/ha | 4 | 15 | 60 | 30 | 125 |
| black nightshade | 8G | 9G | 9G,7C | 2G,1C | 7G |
| speedwell | 0 | 2C | 8G,8C | 6G,5C | 8G |
| wild buckwheat | 2G | 4G,3C | 8G,8C | 4G,2C | 8G,3C |
| wild mustard | 7G,1C | 9G,9C | 9G,9C | 7G,2C | 9G,9C |
| wild radish | 1G,1C | 9G | 10C | 7G,4C | 9G,9C |
| sugar beets | 3G | 7G | 8G | 2G,1C | 8G |
| | | PostEmergence | | | |
| wheat | 0 | 0 | 4G | 0 | 0 |
| barley | 0 | 0 | 4G | 0 | 2G |
| wild oats | 0 | 0 | 3G | 0 | 0 |
| ryegrass | 0 | 0 | 2G,4C | 0 | 1G |
| annual bluegrass | 0 | 0 | 5G | 0 | 0 |
| blackgrass | 0 | 0 | 5G | 0 | 0 |
| green foxtail | 0 | 1G | 2G | 0 | 0 |
| Matricaria inodora | 0 | 2C | 2G,4C | 8G,8C | 9G,9C |
| Galium aparine | 1C | 4C | 5G,5C | 7G | 10C |
| kochia | 0 | 0 | 0 | 3G | 2G |
| black nightshade | 6G,2C | 5G,4C | 9G,4C | 6G | 8G,7C |
| speedwell | 0 | 0 | 4G,5C | 8G | 9G,4C |
| wild buckwheat | 0 | 1C | 2G,3C | 0 | 7G,5C |
| wild mustard | 4C | 7G,6C | 8G,7C | 9G,7C | 10C |
| wild radish | 5G,2C | 7G,6C | 10C | 10C | 10C |
| sugar beets | 0 | 3G | 3G,2G | 0 | 2G,3C |

Test F
Postemergence

Two round pans (25 cm diameter by 12.5 cm deep) were filled with Sassafras sandy loam soil. One pan was planted with blackgrass (*Alopecurus myosuroides*), sugarbeets, nutsedge (*Cyperus rotundus*) tubers, crabgrass (*Digitaria sanguinalis*), sicklepod (*Cassia obtusifolia*), teaweed (*Sida spinosa*), jimsonweed (*Datura stramonium*), velvetleaf (*Abutilon theophrasti*), and giant foxtail (*Setaria faberii*). The other pan was planted with wheat, cotton, rice, corn, soybean, wild oats, (*Avena fatua*), cocklebur (*Xanthium pensylvanicum*), morningglory (*Ipomoea hederacea*), johnsongrass (*Sorghum halepense*) and barnyardgrass (*Echinochloa crusgalli*). The plants were grown for approximately fourteen days, then sprayed postemergence with the chemicals dissolved in a non-phytotoxic solvent.

Preemergence

Two round pans (25 cm diameter by 12.5 cm deep) were filled with Sassafras sandy loam soil. One pan was planted with blackgrass (*Alopecurus myosuroides*), sugarbeets, nutsedge, crabgrass, sicklepod, teaweed, jimsonweed, velvetleaf, and giant foxtail. The other pan was planted with wheat, cotton, rice, corn, soybeans, wild oats, cocklebur, morningglory, johnsongrass, and barnyardgrass. The two pans were sprayed preemergence with the chemicals dissolved in a non-phytotoxic solvent.

Treated plants and controls were maintained in the greenhouse for 28 days, then all treated plants were compared to controls and visually rated for plant response utilizing the rating system previously described for Test A.

Response ratings are contained in Table F.

TABLE F

| | Postemergence | | | | | | | | | | | | | | | | | | | | | | | |
|---|---|---|---|---|---|---|---|---|---|---|---|---|---|---|---|---|---|---|---|---|---|---|---|---|
| | Compound 10 | | | | Compound 11 | | | | Compound 12 | | | Compound 13 | | | | Compound 14 | | | | Compound 15 | | | |
| Rate g/ha | 1 | 4 | 16 | 62 | 1 | 4 | 16 | 62 | 4 | 16 | 62 | 4 | 16 | 62 | 250 | 4 | 16 | 62 | 250 | 4 | 16 | 62 | 250 |
| corn | 0 | 3G | 8G | 9G | 0 | 2G | 8G | 10G | 0 | 0 | 0 | 0 | 0 | 2G | 6G | 0 | 0 | 0 | 0 | 0 | 0 | 3G | 6G |
| wheat | 0 | 0 | 0 | 0 | 0 | 0 | 3G | 6G | 0 | 0 | 0 | 0 | 0 | 0 | 0 | 0 | 0 | 0 | 0 | 0 | 0 | 0 | 4G |
| rice | 0 | 0 | 0 | 2G | 0 | 0 | 2G | 3C | 0 | 0 | 0 | 0 | 0 | 0 | 2G | 0 | 0 | 0 | 0 | 0 | 0 | 4G | 10G |
| soybean | 4G | 7G | 9G | 9G | 3G | 6G | 9G | 10G | 2G | 7G | 10G | 2G | 5G | 8G | 9G | 2G | 7G | 9G | 9G | 2G | 6G | 9G | 10G |
| cotton | 0 | 2C | 7G | 8G | 0 | 2G | 8G | 9G | 0 | 0 | 3G | 0 | 0 | 3G | 8G | 0 | 0 | 4G | 8G | 0 | 2G | 7G | 10G |
| sugarbeet | 0 | 5G | 10C | 10C | 0 | 5G | 9G | 10G | 0 | 4G | 8G | 0 | 0 | 4G | 9G | 0 | 0 | 3G | 10C | 3G | 10C | 10C | 10C |
| crabgrass | 0 | 0 | 0 | 3G | 0 | 0 | 3G | 5G | 0 | 0 | 0 | 0 | 0 | 0 | 0 | 0 | 0 | 0 | 0 | 0 | 0 | 0 | 0 |
| johnsongrass | 0 | 3G | 8G | 10G | 0 | 3G | 8C | 10C | 0 | 0 | 0 | 0 | 0 | 0 | 3G | 0 | 0 | 0 | 0 | 0 | 3G | 10C | 10C |
| blackgrass | 0 | 0 | 5G | 9G | 0 | 4G | 8G | 10C | 0 | 0 | 3G | 0 | 0 | 3G | 8G | 0 | 5G | 9C | 9C | 0 | 5G | 10G | 10G |
| barnyardgrass | 0 | 4G | 7G | 10C | 0 | 4G | 6G | 10C | 0 | 0 | 0 | 0 | 0 | 2G | 7G | 0 | 0 | 0 | 6G | 0 | 4G | 10G | 10C |
| nutsedge | 0 | 0 | 3G | 8G | 0 | 0 | 5G | 9C | 0 | 3G | 6G | 0 | 4G | 7G | 9G | 4G | 9C | 10C | 10C | 3G | 7C | 10C | 10C |
| giant foxtail | 0 | 0 | 2G | 4G | 0 | 0 | 0 | 5G | 0 | 0 | 0 | 0 | 0 | 0 | 2G | 0 | 0 | 0 | 0 | 0 | 2G | 6G | 10G |
| wild oats | 0 | 0 | 3G | 5C | 0 | 0 | 4G | 9C | 0 | 0 | 0 | 0 | 0 | 0 | 0 | 0 | 0 | 0 | 0 | 0 | 3G | 7C | 9C |
| cocklebur | 3G | 9G | 9G | 9G | 3G | 5G | 8G | 9G | 4G | 9G | 10G | 3G | 9G | 9G | 10G | 0 | 5G | 7G | 10G | 8G | 9G | 10G | 10G |
| morningglory | 2G | 6G | 7G | 9G | 0 | 3G | 8G | 9G | 3G | 8G | 10G | 0 | 3G | 6G | 10G | 0 | 5G | 8G | 10G | 3G | 8G | 10G | 10G |
| teaweed | 0 | 0 | 0 | 2G | 0 | 0 | 0 | 3G | 0 | 0 | 0 | 0 | 0 | 0 | 3G | 0 | 0 | 0 | 3G | 0 | 0 | 0 | 3G |
| sicklepod | 0 | 0 | 3G | 3G | 0 | 0 | 2G | 5G | 0 | 2G | 4G | 0 | 0 | 0 | 3G | 0 | 0 | 0 | 3G | 0 | 5G | 7G | 10C |
| jimsonweed | 0 | 4G | 8G | 10C | 0 | 0 | 3G | 9G | 2G | 6G | 9G | 0 | 0 | 4G | 10G | 0 | 3G | 7G | 10G | 4G | 9G | 10G | 10G |
| velvetleaf | 0 | 3G | 6G | 5G | 0 | 0 | 3G | 10C | 0 | 0 | 5G | 0 | 2G | 7G | 9G | 0 | 4G | 7G | 10G | 0 | 7C | 9G | 10C |

| | Preemergence | | | | | | | | | | | | | | | | | |
|---|---|---|---|---|---|---|---|---|---|---|---|---|---|---|---|---|---|---|
| | Compound 10 | | | | Compound 11 | | | | Compound 12 | | | Compound 13 | | | Compound 14 | | Compound 15 | | |
| Rate g/ha | 4 | 16 | 62 | 250 | 4 | 16 | 62 | 250 | 16 | 62 | 250 | 16 | 62 | 250 | 62 | 250 | 16 | 62 | 250 |
| corn | 0 | 0 | 2G | 8G | 0 | 0 | 2G | 7G | 0 | 0 | 0 | 0 | 0 | 2G | 0 | 5G | 0 | 4G | 9G |
| wheat | 0 | 0 | 2G | 8G | 0 | 2G | 5G | 9G | 0 | 0 | 0 | 0 | 0 | 2G | 0 | 0 | 0 | 5G | 7G |
| rice | 0 | 2G | 5G | 10B | 0 | 2G | 9G | 9G | 0 | 4G | 8G | 0 | 2G | 6G | 3G | 7G | 3G | 9G | 10G |
| soybean | 2C | 4H | 8G | 9G | 0 | 2C | 5G | 8G | 0 | 2G | 5G | 0 | 3G | 6G | 0 | 6G | 3G | 7G | 9G |
| cotton | 0 | 0 | 2G | 6C | 0 | 0 | 0 | 2C | 0 | 0 | 4G | 0 | 0 | 3G | 0 | 0 | 0 | 2G | 7G |
| sugarbeet | 2G | 5G | 10E | 10B | 5G | 7G | 10B | 10E | 0 | 0 | 4G | 0 | 5G | 7G | 0 | 2G | 2G | 8G | 10G |
| crabgrass | 0 | 0 | 2G | 9G | 0 | 2G | 4G | 7G | 0 | 0 | 0 | 0 | 0 | 0 | 0 | 0 | 0 | 3G | 6G |
| johnsongrass | 2G | 4G | 8G | 9B | 2G | 4G | 6C | 9G | 0 | 3G | 9G | 0 | 3G | 7G | 0 | 0 | 3G | 9G | 10G |
| blackgrass | 2G | 4G | 8E | 10E | 2G | 4G | 8E | 10E | 3G | 5G | 8G | 3G | 7G | 9G | 5G | 10G | 3G | 7G | 10G |
| barnyardgrass | 0 | 2C | 7G | 9G | 0 | 0 | 5G | 8G | 0 | 2G | 6G | 0 | 7G | 10G | 4G | 9G | 3G | 8G | 10G |
| nutsedge | 0 | 3G | 7G | 10E | 0 | 2G | 4G | 9G | 0 | 2G | 6G | 0 | 0 | 2G | 4G | 9G | 0 | 4G | 10E |
| giant foxtail | 0 | 0 | 6G | 10E | 0 | 0 | 6G | 7G | 0 | 2G | 8G | 0 | 4G | 8G | 3G | 7G | 2G | 10G | 10E |
| wild oats | 0 | 0 | 3G | 9G | 0 | 2G | 5G | 8G | 0 | 0 | 0 | 0 | 2G | 5G | 0 | 0 | 0 | 5G | 8G |
| cocklebur | 2G | 6G | 9G | 9G | 0 | 3G | 7G | 9G | 0 | 5G | 9G | 3G | 8G | 9G | 2C | 9G | 2G | 8G | 9G |
| morningglory | 0 | 2C | 6G | 9G | 0 | 2C | 4H | 8H | 0 | 0 | 6G | 0 | 0 | 3G | 0 | 0 | 0 | 4G | 7C |
| teaweed | 0 | 0 | 2C | 8G | 0 | 0 | 3C | 5C | 0 | 0 | 5G | 0 | 3G | 7G | 0 | 0 | 0 | 4G | 5G |
| sicklepod | 0 | 0 | 2C | 7G | 0 | 0 | 4G | 5G | 0 | 0 | 5G | 0 | 0 | 6G | 0 | 0 | 0 | 5G | 7G |
| jimsonweed | 0 | 0 | 3G | 8G | 0 | 0 | 4G | 8C | 0 | 3G | 8G | 4G | 8G | 9G | 3G | 8G | 0 | 3G | 9G |

What is claimed is:
1. A compound of the formula:

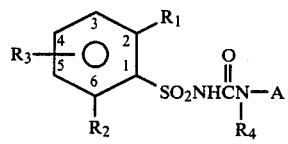

wherein
$R_1$ is $S(O)_nR_5$, $NR_6R_7$, $CO_2R_8$, $SO_2NR_9R_{10}$,

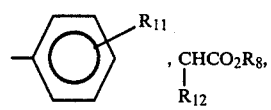

$OSO_2R_{13}$, $CH_2OR_{14}$ or Q;
$R_2$ is $S(O)_mR_5$, $NR_6R_7$, $CO_2R_8$, $SO_2NR_9R_{10}$,

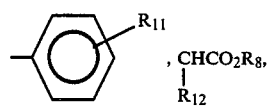

$OSO_2R_{13}$, $CH_2OR_{14}$ or Q;
$R_3$ is H, Cl, F, Br, $CH_3$, $OCH_3$ or $CF_3$;
$R_4$ is H or $CH_3$;
$R_5$ is $C_1$-$C_3$ alkyl;
$R_6$ and $R_7$ are independently $CH_3$ or $CH_2CH_3$;
$R_8$ is $C_1$-$C_3$ alkyl, $CH_2CH=CH_2$, $CH_2CH_2Cl$ or $CH_2CH_2OCH_3$;
$R_9$ is $CH_3$ or $OCH_3$;
$R_{10}$ is $C_1$-$C_3$ alkyl;
$R_{11}$ is H, Cl, Br, F, $CH_3$ or $OCH_3$;
$R_{12}$ is H or $CH_3$;
$R_{13}$ is $C_1$-$C_3$ alkyl or $CF_3$;
$R_{14}$ is $C_1$-$C_3$ alkyl or $CF_2H$;
n is 0, 1 or 2;
m is 0 or 1;

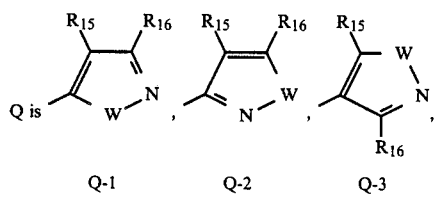

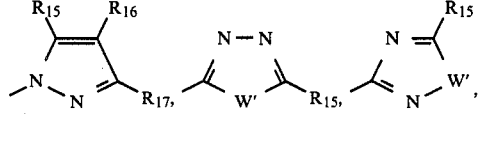

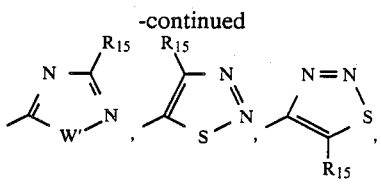

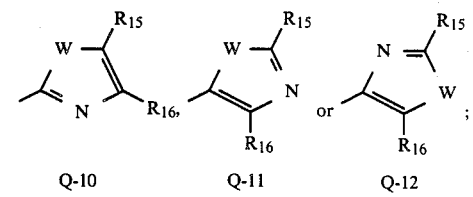

W is O, S, or $NR_{18}$;
W' is O or S;
$R_{15}$, $R_{16}$, $R_{17}$ and $R_{18}$ are independently H or $CH_3$;
Q is also

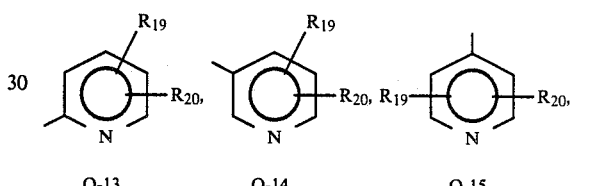

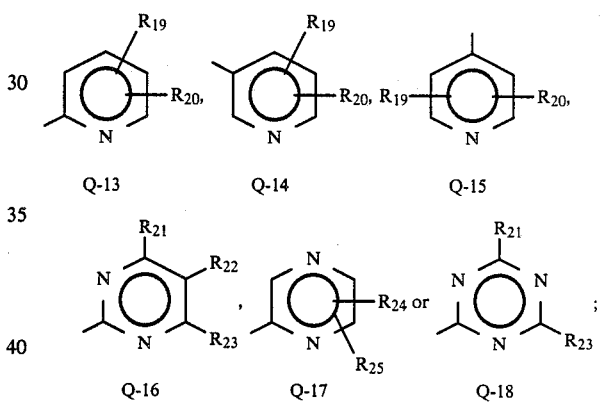

$R_{19}$, $R_{20}$, $R_{22}$, $R_{24}$ and $R_{25}$ are independently H or $CH_3$;
$R_{21}$ and $R_{23}$ are independently H, $CH_3$ or $OCH_3$;
Q is also

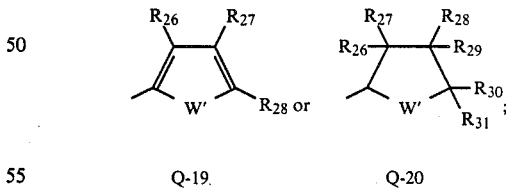

$R_{26}$, $R_{27}$, $R_{28}$ $R_{29}$, $R_{30}$ and $R_{31}$ are independently H or $CH_3$;

A is —$CH_2$—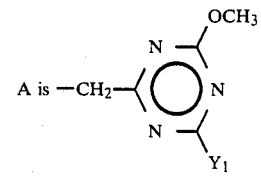

A-5

$Y_1$ is $CH_3$ or $OCH_3$;

and agriculturally suitable salts thereof; provided that
(a) $R_1$ and $R_2$ are not simultaneously $CO_2R_8$;
(b) when either one of $R_1$ or $R_2$ is $SO_2NR_9R_{10}$, then the other must not be $S(O)_nR_5$, $S(O)_mR_5$, $CH_2OR_{14}$ or $NR_6R_7$;
(c) when $R_9$ is $OCH_3$, then $R_{10}$ is $CH_3$;
(d) when either one of $R_1$ or $R_2$ is $CO_2R_8$, then the other must not be $S(O)_nR_5$, $S(O)_mR_5$ or $NR_6R_7$;
(e) the total number of carbon atoms in $R_{26}$ to $R_{31}$ combined, is equal to or less than four.

2. A compound of claim 1 wherein A is A-5, $R_1$ and $R_2$ are not simultaneously Q and $R_4$ is H.

3. A compound of claim 2 wherein $R_3$ is in either the 3- or 5-position.

4. A compound of claim 3 wherein $R_1$ and $R_2$ are not simultaneously $SO_2NR_9R_{10}$ or $NR_6R_7$.

5. A compound of claim 4 wherein $R_3$ is H and at least one of $R_1$ or $R_2$ is $S(O)_nR_5$, $S(O)_mR_5$, $NR_6R_7$, $SO_2NR_9R_{10}$,

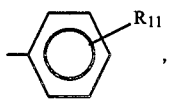

$OSO_2R_{13}$ or $CH_2OR_{14}$.

6. A compound of claim 5 wherein $R_5$ is $CH_3$ or $CH_2CH_3$, $R_6$ and $R_7$ are both $CH_3$, $R_{10}$ is $CH_3$, $R_{11}$ is H, $R_{13}$ is $CH_3$ or $CH_2CH_3$ and $R_{14}$ is $CH_3$.

7. An agriculturally suitable composition for controlling the growth of undesired vegetation comprising an effective amount of a compound of claim 1 and at least one of the following: surfactant, solid or liquid diluent.

8. The composition of claim 7 wherein the compound is of claim 2.

9. The composition of claim 7 wherein the compound is of the claim 4.

10. The composition of claim 7 wherein the compound is of claim 5.

11. The composition of claim 7 wherein the compound is of claim 6.

12. The composition of claim 7 wherein the compound is of claim 7.

13. A method for controlling the growth of undesired vegetation which comprises applying to the locus to be protected postemergence or preemergence an effective amount of a compound of claim 1.

14. A method for controlling the growth of undesired vegetation which comprises applying to the locus to be protected postemergence or preemergence an effective amount of a compound of claim 2.

15. A method for controlling the growth of undesired vegetation which comprises applying to the locus to be protected postemergence or preemergence an effective amount of a compound of claim 3.

16. A method for controlling the growth of undesired vegetation which comprises applying to the locus to be protected postemergence or preemergence an effective amount of a compound of claim 4.

17. A method for controlling the growth of undesired vegetation which comprises applying to the locus to be protected postemergence or preemergence an effective amount of a compound of claim 5.

18. A method for controlling the growth of undesired vegetation which comprises applying to the locus to be protected postemergence or preemergence an effective amount of a compound of claim 6.

* * * * *